United States Patent
Yodfat et al.

(10) Patent No.: US 9,808,574 B2
(45) Date of Patent: Nov. 7, 2017

(54) INSERTION DEVICE

(75) Inventors: Ofer Yodfat, Maccabim-Reut (IL); Avraham Neta, Misgav (IL); Illai Gescheit, Misgav (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 354 days.

(21) Appl. No.: 12/215,255

(22) Filed: Jun. 25, 2008

(65) Prior Publication Data

US 2008/0319414 A1    Dec. 25, 2008

Related U.S. Application Data

(60) Provisional application No. 60/937,155, filed on Jun. 25, 2007, provisional application No. 60/937,214, (Continued)

(51) Int. Cl.
*A61M 5/142* (2006.01)
*A61B 5/00* (2006.01)
(Continued)

(52) U.S. Cl.
CPC ....... *A61M 5/14248* (2013.01); *A61B 5/6849* (2013.01); *A61M 5/158* (2013.01);
(Continued)

(58) Field of Classification Search
CPC ................ A61M 5/14248; A61M 5/24; A61M 2005/14252; A61M 2005/14256;
(Continued)

(56) References Cited

U.S. PATENT DOCUMENTS 3,396,726 A * 8/1968 Sarnoff .......................... 604/138
4,755,173 A    7/1988 Konopka et al. ............. 604/167
(Continued)

FOREIGN PATENT DOCUMENTS

WO    WO 99/33504      7/1999
WO    WO-2005046781 A1   5/2005
(Continued)

OTHER PUBLICATIONS

International Search Report, PCT Application No. PCT/IL2008/000860, date of mailing Oct. 2, 2008.
(Continued)

*Primary Examiner* — Bhisma Mehta
*Assistant Examiner* — Larry R Wilson
(74) *Attorney, Agent, or Firm* — Dinsmore & Shohl, LLP

(57) ABSTRACT

An insertion apparatus and a method for use with a device for delivery of a therapeutic fluid into a body of a patient and/or for sensing of a bodily analyte are disclosed. The apparatus includes a housing adapted for loading therein at least one cannula cartridge unit having a protective member. The protective member accommodates at least one penetrating cartridge having a subcutaneously insertable element and a penetrating member. The apparatus includes a displacement mechanism capable of protracting the penetrating cartridge towards the body of the patient, where protraction of the penetrating cartridge results in insertion of the subcutaneously insertable element into the body of the patient.

21 Claims, 50 Drawing Sheets

Related U.S. Application Data filed on Jun. 25, 2007, provisional application No. 60/937,163, filed on Jun. 25, 2007.

(51) Int. Cl.

| | | |
|---|---|---|
| *A61M 5/158* | (2006.01) | |
| *A61M 5/42* | (2006.01) | |
| *A61B 5/145* | (2006.01) | |
| *A61M 5/14* | (2006.01) | |

(52) U.S. Cl.
CPC .......... *A61M 5/422* (2013.01); *A61B 5/14532* (2013.01); *A61M 5/1413* (2013.01); *A61M 2005/1426* (2013.01); *A61M 2005/14252* (2013.01); *A61M 2005/1581* (2013.01); *A61M 2005/1585* (2013.01); *A61M 2205/362* (2013.01); *A61M 2205/3606* (2013.01); *A61M 2205/3673* (2013.01)

(58) Field of Classification Search
CPC ........... A61M 2005/14284; A61M 2005/2403; A61M 2005/2414; A61M 2005/2433; A61M 2005/2437; A61M 2005/244; A61M 2039/0232; A61M 5/158; A61M 2005/1426; A61M 2005/341; A61B 5/6849
USPC ...... 604/136–138, 156–158, 164.04, 164.06, 604/164.11, 164.12, 180, 272, 506, 513, 604/890.1
See application file for complete search history.

(56) References Cited

U.S. PATENT DOCUMENTS

| | | | | |
|---|---|---|---|---|
| 5,176,662 | A | | 1/1993 | Bartholomew et al. ...... 604/283 |
| 5,196,019 | A | * | 3/1993 | Davis ................. A61B 17/3403 378/81 |
| 5,257,980 | A | | 11/1993 | Van Antwerp et al. ...... 604/282 |
| 5,292,325 | A | * | 3/1994 | Gurmarnik ............ A61M 5/427 128/DIG. 26 |
| 5,390,671 | A | | 2/1995 | Lord et al. ..................... 128/635 |
| 5,568,806 | A | | 10/1996 | Cheney, II et al. ........... 128/635 |
| 5,586,553 | A | | 12/1996 | Halili et al. .................. 128/635 |
| 6,093,172 | A | * | 7/2000 | Funderburk .......... A61M 5/158 604/131 |
| 6,143,164 | A | | 11/2000 | Heller et al. ................ 295/777.5 |
| 6,254,586 | B1 | | 7/2001 | Mann et al. |
| 6,699,218 | B2 | | 3/2004 | Flaherty et al. ............. 604/131 |
| 6,830,562 | B2 | | 12/2004 | Mogensen et al. ...... 604/164.12 |
| 7,110,803 | B2 | | 9/2006 | Shults et al. ................. 600/347 |
| 2003/0100862 | A1 | | 5/2003 | Edwards et al. |
| 2004/0116847 | A1 | * | 6/2004 | Wall ..................... A61K 9/0019 604/93.01 |
| 2004/0133164 | A1 | * | 7/2004 | Funderburk ....... A61B 5/14532 604/134 |
| 2004/0158207 | A1 | * | 8/2004 | Hunn .................... A61M 5/158 604/164.01 |
| 2005/0101932 | A1 | | 5/2005 | Cote et al. |
| 2006/0020189 | A1 | * | 1/2006 | Brister ................. A61B 5/0002 600/345 |
| 2007/0093754 | A1 | * | 4/2007 | Mogensen et al. ...... 604/164.01 |
| 2007/0191702 | A1 | | 8/2007 | Yodfat et al. ................. 600/365 |
| 2008/0097481 | A1 | * | 4/2008 | Schorr ............... A61B 17/0469 606/144 |
| 2008/0214916 | A1 | | 9/2008 | Yodfat et al. ................. 600/347 |
| 2008/0215035 | A1 | | 9/2008 | Yodfat et al. ................. 604/513 |
| 2008/0281290 | A1 | | 11/2008 | Yodfat et al. ................. 604/504 |
| 2008/0319416 | A1 | | 12/2008 | Yodfat et al. ................. 604/513 |
| 2009/0012472 | A1 | * | 1/2009 | Ahm .................. A61M 5/14248 604/138 |
| 2009/0163867 | A1 | * | 6/2009 | Marshall ........... A61M 5/31586 604/136 |
| 2009/0198215 | A1 | * | 8/2009 | Chong ................ A61M 5/1413 604/506 |

FOREIGN PATENT DOCUMENTS

| | | |
|---|---|---|
| WO | WO 2007/093981 | 8/2007 |
| WO | WO 2008/012817 A1 | 1/2008 |
| WO | WO 2008/029403 | 3/2008 |
| WO | WO 2008/038274 | 4/2008 |
| WO | WO 2008/065646 | 6/2008 |
| WO | WO 2008/078318 | 7/2008 |
| WO | WO 2008/078319 | 7/2008 |
| WO | WO 2009/001345 | 12/2008 |
| WO | WO 2009/056981 | 5/2009 |

OTHER PUBLICATIONS

Final Office Action dated Dec. 27, 2010 for U.S. Appl. No. 12/215,219 (8 pgs.).
Response to May 6, 2010 Office Action filed on Oct. 6, 2010 for U.S. Appl. No. 12/215,219 (21 pgs.).
Interview Summary dated Jul. 26, 2010 for U.S. Appl. No. 12/215,219 (4 pgs.).
Non-Final Office Action dated May 6, 2010 for U.S. Appl. No. 12/215,219 (11 pgs.).
Advisory Action dated Mar. 11, 2010 for U.S. Appl. No. 12/215,219 (3 pgs.).
Response Under 37 C.F.R. 1.116 filed on Feb. 23, 2010 for U.S. Appl. No. 12/215,219 (16 pgs.).
Final Office Action dated Nov. 23, 2009 for U.S. Appl. No. 12/215,219 (16 pgs.).
Amendment and Response Under 37 C.F.R. 1.111 filed on Jul. 13, 2009 for U.S. Appl. No. 12/215,219 (11 pgs.).
Non-Final Office Action dated Mar. 13, 2009 for U.S. Appl. No. 12/215,219 (11 pgs.).

* cited by examiner

INSERTION DEVICE

CROSS-REFERENCE TO RELATED APPLICATIONS

The present application claims priority to U.S. Provisional Patent Application No. 60/937,214, entitled "Insertion Device for Inserting a Cannula into a Body", U.S. Provisional Patent Application No. 60/937,155, entitled "Protector for Cannula and Penetrating Member Insertable in the Body of a Patient", and U.S. Provisional Patent Application No. 60/937,163, entitled "Devices and Methods for Pain Reduction", all filed on Jun. 25, 2007, the disclosures of which are incorporated herein by reference in their entireties.

FIELD OF THE INVENTION

The present invention generally relates to medical devices, and particularly to devices that administer medication into the body of a patient and/or sense analyte levels in a bodily fluid. More particularly, some embodiments of the present invention are directed to an insertion device and a method for manual or automatic insertion of a cannula into a human body for delivering a drug using a skin adherable patch unit and/or for continuous sensing of a bodily analyte.

BACKGROUND OF THE INVENTION

Continuous subcutaneous delivery of medication or monitoring of a body analyte is often accomplished using a cannula inserted into a human body that remains in place for several days. Diabetes patients may use such cannula, which is positioned in a subcutaneous compartment for continuous delivery of insulin by pumps or for monitoring interstitial glucose levels by sensors. A combination of a tube connecting the insulin pump to the cannula and a detachable connector is often referred to as an infusion set. Such infusion sets and modes of their insertion are disclosed, for example, in U.S. Pat. Nos. 4,755,173, 5,176,662 and 5,257,980. Subcutaneous cannula insertion modes for continuous glucose monitoring are discussed, for example, in U.S. Pat. Nos. 5,390,671, 5,568,806 and 5,586,553. Usually, transcutaneous ("hypodermic") cannula insertion can be carried out with a sharp metal penetrating member to be withdrawn after skin piercing. This procedure can be carried out manually by the user/patient. The insertion is usually painful and requires considerable skill. Some patients are reluctant or hesitant to pierce their own skin, and thus, encounter difficulties in proper cannula insertion. Such difficulties can be attributed to insufficient manual dexterity or, alternatively, to anxiety associated with anticipated discomfort as the needle pierces the skin. This problem can be especially significant when an insulin pump is used, since misplacement of the cannula can cause kinking, incorrect insertion angle or incorrect cannula insertion depth leading eventually to cannula obstruction. As a result, delivery of insulin could be hampered thereby causing a life-threatening situation.

In an attempt to cope with this problem, automatic infusion set insertion devices ("inserters") were developed to assure correct placement of a cannula into the subcutaneous layer at a correct angle while minimizing pain and hazardous obstructions associated with cannula insertion. U.S. Pat. Nos. 6,093,172 and 6,830,562 disclose inserters having a spring-loaded plunger for an automatic subcutaneous placement of an infusion set. These automatic inserters can be used with "pager like" pumps having long tubing and a cannula altogether constituting an "infusion set". However, these devices cannot be used for insertion of a cannula used with skin adherable pumps that do not employ long tubing. Such device is discussed in U.S. Pat. No. 6,699,218 to Flaherty et al. In Flaherty's skin adherable device, the cannula is rigidly connected to the pump's housing. After adhesion to user's skin, the cannula is fired, thereby emerging from the device's housing and piercing the skin. Consecutively, the penetrating member is retracted back into the pump's housing. This device is relatively bulky, heavy and indiscreet because the spring-loaded mechanism is deployed within the device's housing during the entire period of usage. In addition, the cannula has only a single length size and penetrates the skin only at a certain angle; the patient cannot adjust these parameters based on various insertion sites and other clinical requirements.

Continuous glucose monitors are disclosed in U.S. Pat. Nos. 5,390,671 and 6,143,164, assigned to MiniMed and E. Heller & Company, respectively. These devices monitor glucose levels in the subcutaneous compartment using a sensor, which is inserted manually or automatically in a fashion similar to the insertion of a cannula, as disclosed in U.S. Pat. No. 7,110,803, assigned to DexCom.

Thus, it would be desirable to provide improved systems and methods for inserting a cannula and/or sensor into the body of a patient.

SUMMARY OF THE INVENTION

In some embodiments, the present invention relates to a device and a method for automatic insertion of a sensor, which can be suitable for continuous analyte (e.g., glucose) monitoring and which can be adhered to a patient's skin. The present invention also relates to an automatic insertion of a cannula (e.g., a single cannula or multiple cannulae) that can be used for delivery of medication (e.g., insulin) and can be used for continuous monitoring of body analyte (e.g., glucose). In some embodiments, the present invention relates to an automatic insertion of two cannulae coupled to a single patch, wherein one cannula is used for delivery of medication and the other for continuous monitoring of a bodily analyte. For example, a patch could include one cannula for drug delivery and one sensor for sensing analytes. The present invention further allows insertion of a cannula at any desired depth, i.e., the user can choose the desired cannula length size. Further, the cannula can be inserted at any desired angle.

In some embodiments, the cannula insertion device can fit comfortably in the user's hand. The cannula insertion device can include minimal number of parts, which is easy to assemble, and which is inexpensive. In some embodiments, the cannula insertion device can be either reusable or disposable.

In some embodiments, the present invention relates to an inserter device for a precise placement of a cannula within a body of a user. The device can be used for automatic insertion of a cannula that is employed together with, for example, a fluid dispensing device (which is also referred to herein as a fluid delivery pump). The pump can be configured as a remote-controlled skin adherable patch (also, referred to herein as a dispensing patch unit) allowing programmed fluid delivery. The pump also can include means for continuous analyte level monitoring. In some embodiments, the dispensed fluid is insulin and the monitored analyte is glucose. In some embodiments, the dispensing device includes the following three units:

1. A dispensing patch unit having:
   a. A reusable part containing a driving mechanism, a printed circuit board ("PCB"), and electronics.
   b. A disposable part containing a reservoir, a delivery tube and an outlet port with a connecting lumen.
2. A cradle unit for connecting and reconnecting the dispensing patch unit to the body. The cradle has a tubular passage, referred to as "well", for allowing cannula penetration of the skin. The cradle also has an adhesive layer for attachment to the body.
3. A cannula cartridge unit, which can be a disposable item. The cannula cartridge unit includes a cannula, a penetrating member, and a protector. The cannula is also provided with a hub disposed within the cannula cartridge unit and which contains a rubber septum that can be repeatedly pierced by a connecting lumen provided in the disposable part of the dispensing patch unit.

A method for setting up the above system can include the following steps:
1. fill the reservoir with therapeutic fluid;
2. assemble the dispensing patch unit from two parts (i.e., a disposable part and a reusable part);
3. adhere the cradle unit to the skin of the user (in some embodiments, this step can be performed after connecting the inserter to the cradle unit);
4. insert cannula, where this step includes:
   a. load the cannula cartridge unit into the inserter (in some embodiments, this step can be performed after connecting the inserter to the cradle unit);
   b. connect the inserter to the cradle unit;
   c. advance the cannula, either automatically or manually, through the cradle unit towards the body, thereby piercing the skin and disposing the cannula in the subcutaneous compartment; and,
   d. withdraw the penetrating member, either automatically or manually, from the body into the protector, while the cannula remains in the cradle unit;
5. connect the dispensing patch unit to the cradle unit, such that a connecting lumen emerges from the disposable part's outlet port and pierces the cannula hub's rubber septum to maintain fluid communication between the reservoir, the delivery tube, the cannula and the subcutaneous tissue;
6. using a remote control unit, program fluid delivery.

In some embodiments, the cannula delivering the fluid (e.g., insulin) also includes a sensor for monitoring a bodily analyte (e.g., glucose). Fluid delivery can be adjusted based on sensor inputs (in a semi- or fully-closed-loop system). In some embodiments, the dispensing patch unit can include both the cannula for fluid delivery and a sensor for analyte sensing, which can both be inserted into the body.

In some embodiments, the present invention relates to an automatic insertion of the cannula for delivery of medication to a patient using the fluid delivery skin adherable patch pump.

In some embodiments, the present invention relates to an automatic insertion of a sensor suitable for continuous analyte monitoring and that can be adhered to the skin of the patient.

In some embodiments, the present invention relates to an automatic insertion of a single cannula that can be used for delivery of medication (e.g., insulin) and for continuously monitoring of body analyte (e.g., glucose).

In some embodiments, the present invention relates to an automatic insertion of two cannulae coupled to one patch, where one cannula is used for delivery of medication and the other for continuously monitoring a body analyte. In some embodiments, the patch contains one cannula for drug delivery and one sensor for sensing and monitoring analytes.

In some embodiments, the present invention relates to manual and/or automatic insertion of a cannula that can pass through a "well assembly" and be inserted into a subcutaneous compartment. In some embodiments, the cannula can pass through a "cradle unit" and be inserted into the subcutaneous compartment. The cannula can be inserted at any desired depth, i.e., the user can choose the desired cannula length size and/or any desired angle.

In some embodiments, the cannula can be inserted and the penetrating member can be retracted manually. In some embodiments, insertion of the cannula and retraction of the penetrating member are automatic. In some embodiments, insertion of the cannula is automatic and retraction of the penetrating member is manual.

In some embodiments, a cannula insertion device allows precise alignment of the cannula relative to the "well assembly". Highly accurate alignment is desirable for the following reasons: 1) it avoids tearing of the well's lower gasket, thus, maintaining intact sealing; 2) it permits skin penetration at any desired angle; 3) it provides sealing of the upper opening with the rubber cap; and 4) it allows precise placement of the cannula within the well and maintenance of flow communication. In some embodiments, the cannula insertion device maintains precise alignment of the cannula relative to the "cradle unit" and maintains connection of the cannula to the cradle after insertion. In some embodiments, the cannula insertion device can be connected to the cradle unit before adhesion and used as a means for attaching the cradle unit to the patient's body. In some embodiments, the cannula insertion device can be automatically detached from the cradle unit after the cannula has been inserted, for example, to avoid unintentional detachment of the cradle from the skin.

In some embodiments, the cannula insertion device is spring-loaded. The spring can be loaded by the patient and released upon patient's discretion. The inserter can be configured to prevent unintentional or premature firing. In some embodiments, the cannula insertion device is suitable for use in conjunction with a cannula protector. The cannula protector can be easily manipulated by the user and may be receivable within the inserter and positioned in a single spatial direction. In some embodiments, the cannula insertion device fits comfortably in the user's hand. In some embodiments, the cannula insertion device has relatively few parts, which are easy to assemble and are inexpensive. The cannula insertion device can be reusable. In other embodiments, the cannula insertion device can be disposable.

In some embodiments, the present invention relates to an automatic insertion of the cannula and/or the sensor used in association with the skin adherable infusion pump having analyte sensing and drug dispensing capabilities and in which the fluid dispensing can be adjusted according to analyte sensing (in semi- or fully-closed loop mode). In some embodiments, the inserter can be preloaded with the cannula cartridge unit and the cradle unit. Upon spring loading, the user attaches the cradle unit to the skin and pushes a release button. A spring loaded flywheel forcibly pushes the cannula and the penetrating member through the well into the body. Consecutively, the penetrating member is automatically retracted into the protector while the cannula hub remains connected to the well. Finally, the inserter is detached from the cradle unit and the protector (with penetrating member inside) is unloaded from the inserter and is disposed of. In some embodiments, the inserter can be preloaded with at least one (or more than one) cannula cartridge unit.

In some embodiments, the present invention includes a disposable inserter preloaded with the cannula cartridge unit and after cannula insertion, the used protector (with the penetrating member inside) remains within the inserter's housing, which is then can be discarded.

In some embodiments, the present invention provides an inserter that allows for passing of the cannula through the well assembly and its penetration through the skin. After insertion, the cannula remains in the body, the cannula hub is secured to the well and the penetrating member can be retracted. In some embodiments, the inserter enables alignment of the cannula with the cradle unit. In some embodiments, the inserter enables alignment of the cannula with the outlet port in the dispensing patch unit's housing and the passage of the well assembly. In some embodiments, the inserter includes a drum member suitable for retaining one or more cannula cartridge units. In some embodiments, the inserter contains safety means for preventing inadvertent or premature insertion. The safety means may be an integral part of the inserter or it may be an additional component which is detachable from the inserter before operation. In some embodiments, safety means are provided for disposing of the sharp penetrating member after manual retraction of penetrating member from the body.

BRIEF DESCRIPTION OF THE DRAWINGS

For a better understanding of the present invention, including the various objects and advantages thereof, reference is made to the following description, which is to be taken in conjunction with the accompanying illustrative drawings.

DETAILED DESCRIPTION OF THE INVENTION

Figure 1A:
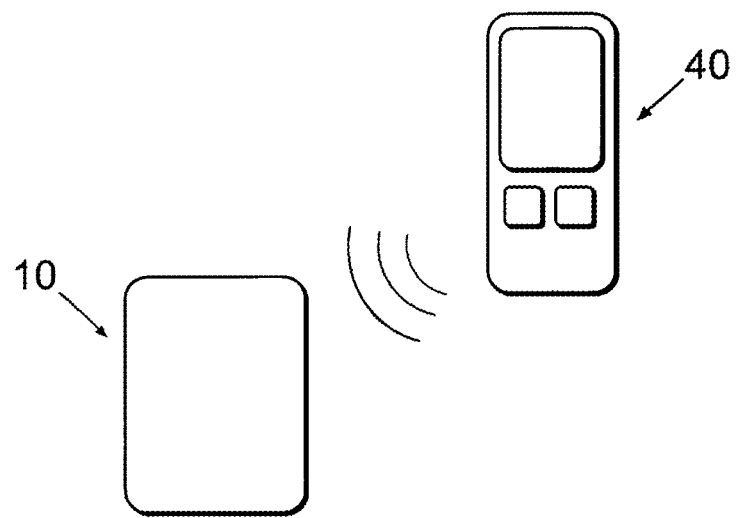
FIGS. 1a-c show exemplary single-part dispensing unit, two-part dispensing unit and remote control unit, according to some embodiments of the present invention.

A skin adherable insulin delivery device was disclosed in a co-owned/co-pending International Patent Application No. PCT/IL07/000932, filed Jul. 24, 2007, claiming priority to U.S. Provisional Patent Application No. 60/833,110, filed Jul. 24, 2006, and U.S. Provisional Patent Application No.

60/837,877, filed Aug. 14, 2006, and also disclosed in a co-owned/co-pending U.S. patent application Ser. No. 12/004,837, and International Patent Application No. PCT/IL07001578, both filed Dec. 20, 2007 and both claiming priority to U.S. Provisional Patent Application No. 60/876,679, filed Dec. 22, 2006. The disclosures of the above applications are incorporated herein by reference in their entirety. The device contains a remote control unit and a skin adherable unit ("dispensing patch unit"). The dispensing patch unit is coupled to a unique cannula apparatus, which does not require an infusion set and long tubing. The cannula apparatus allows the patient to choose the desired depth and angle for cannula insertion. In some embodiments, the device is provided with a "well assembly" connected to an insulin delivery tube. The well assembly has an upper opening and a lower opening sealed by rubber gasket. The insertion apparatus is provided also with a "penetrating cartridge" having a cannula, a penetrating member and a rubber cap. The penetrating cartridge allows for the cannula to penetrate through the well assembly and then through the skin, while keeping the upper opening sealed and maintaining the delivery of insulin. In some embodiments, the device includes a "cradle unit". The cradle unit is configured as a sheet with an adhesive layer that is attached to the skin before cannula insertion, and is used to allow connection and disconnection of the dispensing patch unit to and from the body. The cannula is inserted through the cradle unit into the skin and remains secured at the cradle unit after insertion. The penetrating member, which is configured as a sharp needle, is then retracted and disposed of.

In co-pending, co-owned International Patent Application No. PCT/IL2008/000861 and U.S. patent application Ser. No. 12/215,219, entitled "Portable Infusion Pump with Cannula Inserter and Pain Reduction Mechanism" and "Protector Mechanism," respectively, and claiming priority to U.S. Provisional Patent Application No. 60/937,155, filed on Jun. 25, 2007, a device and a method are disclosed for protecting the user from unintentional pricking by providing a protective cover that shields the penetrating cartridge, further referred to as a "protector." The disclosures of the above applications are incorporated herein by reference in their entireties. The protector is detachably connectable to the cradle unit and consecutively the cannula can be manually or automatically inserted. Upon insertion and piercing of the skin, the penetrating member is retracted into the protector and both items can be disposed of.

Continuous glucose monitors are disclosed in a co-owned/co-pending International Patent Application No. PCT/IL07/001096, filed Sep. 5, 2007, claiming priority to U.S. Provisional Patent Applications No. 60/842,869, filed Sep. 6, 2006, and International Patent Application No. PCT/IL07/001177, filed Sep. 25, 2007, claiming priority to U.S. Provisional Patent Application No. 60/848,511, filed Sep. 29, 2006. The disclosures of the above applications are incorporated herein by reference in their entireties.

The further description of the invention deals mostly with insertion of a cannula. It should be borne in mind however that this description may be equally used for insertion of a sensor for sensing bodily analyte or any other subcutaneously insertable element.

Figure 1B:
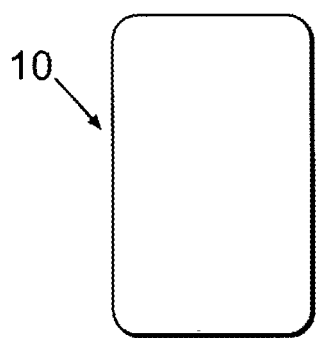
Figure 1C:
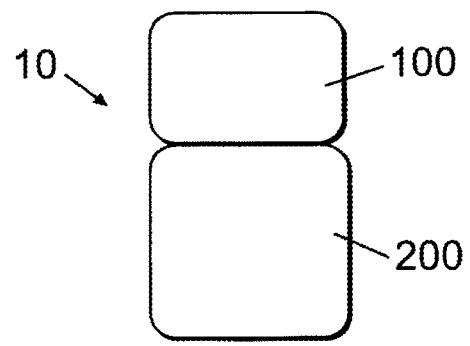

FIG. 1a shows an example of the fluid delivery device in which the inserter of the present invention can be implemented. The delivery device includes a dispensing patch unit (10) and a remote control unit (40). In some embodiments, the dispensing patch unit (10) can include a single part (as shown in FIG. 1b) or two parts (as shown in FIG. 1c), i.e., a reusable part (100) and a disposable part (200). The dispensing unit (10) communicates with the remote control unit (40) that can forward commands, receive and process instructions from the dispensing unit (10), etc. The remote control unit (40) can include a display and a plurality of buttons to control operation of the units (10) and (40). The units (10) and (40) can communicate with a wireless, wired, wire line, RF or any other type communication. The unit (40) can be a personal computer, a laptop, an iPod, a PDA, a cellular telephone, a remote control, or any other suitable device. In some embodiments, fluid delivery can be programmed solely by a remote control unit (40) having a bidirectional communication link with the transceiver provided in the dispensing unit (10).

Figure 2A:
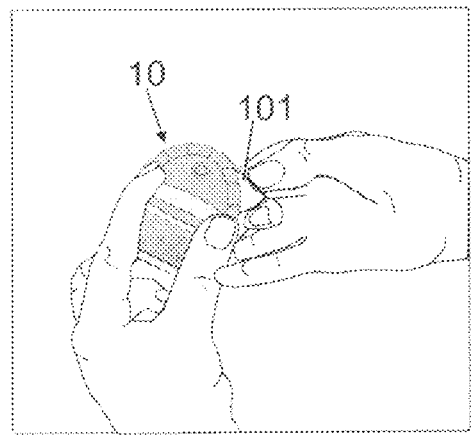
FIGS. 2a-c show an exemplary dispensing unit directly adhered to the skin of a patient, according to some embodiments of the present invention.
Figure 2B:
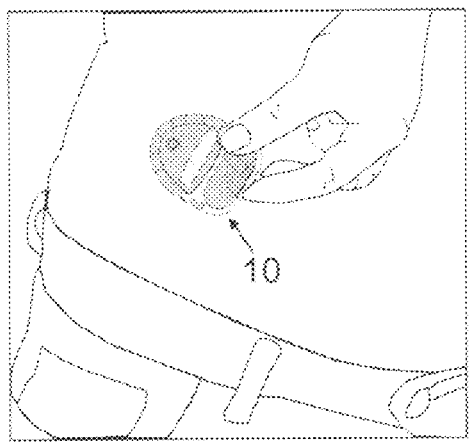
Figure 2C:
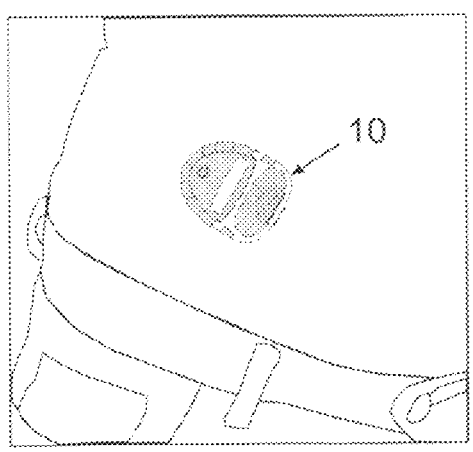

FIGS. 2a-c show an example of a direct adherence of the dispensing patch unit (10) to the skin (5) of the user/patient. FIG. 2a shows peeling of an adhesive protective sheet (101) from the dispensing patch unit (10). FIG. 2b shows adherence of the dispensing patch unit (10) to the skin (5). FIG. 2c shows the dispensing patch unit (10) being adhered to the skin (5) and ready for operation.

Figure 3A:
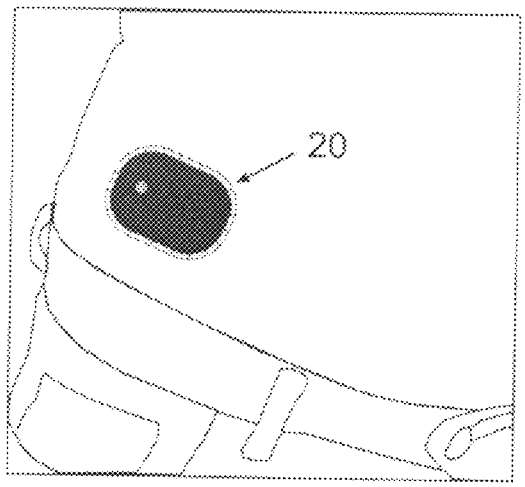
FIGS. 3a-c show an exemplary connection of the dispensing unit to a cradle unit, according to some embodiments of the present invention.
Figure 3B:
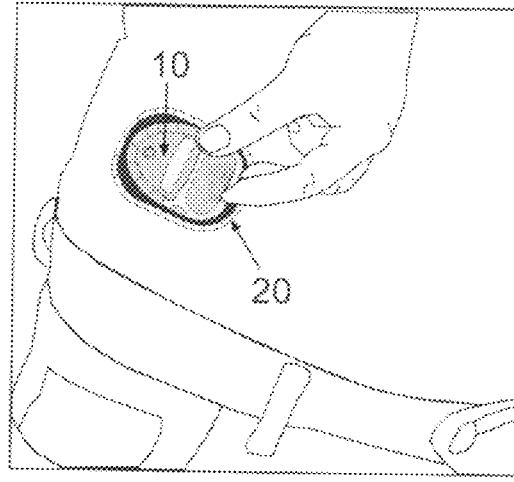
Figure 3C:
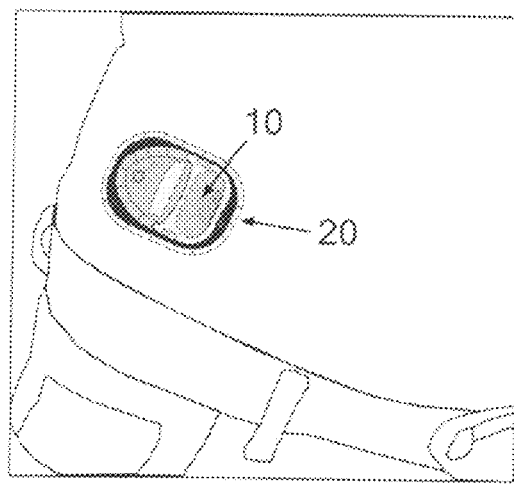

In some embodiments, shown in FIGS. 3a-c, the fluid dispensing device can be provided with a cradle unit (20), which can be adhered first to the skin (5). The dispensing patch unit (10) can then be connected to and disconnected from the cradle unit (20) upon patient's discretion. An example of the device employing a cradle unit is disclosed in a co-pending/co-owned U.S. patent application Ser. No. 12/004,837, and International Patent Application No. PCT/IL07001578, both filed Dec. 20, 2007 and both claiming priority to U.S. Patent Application No. 60/876,679, filed Dec. 22, 2006.

FIG. 3a shows the cradle unit (20) being adhered to the skin (5). FIG. 3b shows connection of the dispensing patch unit (10) to the adhered cradle unit (20). FIG. 3c shows the dispensing patch unit (10) being connected to the cradle unit (20) and ready for operation.

Figure 4A:
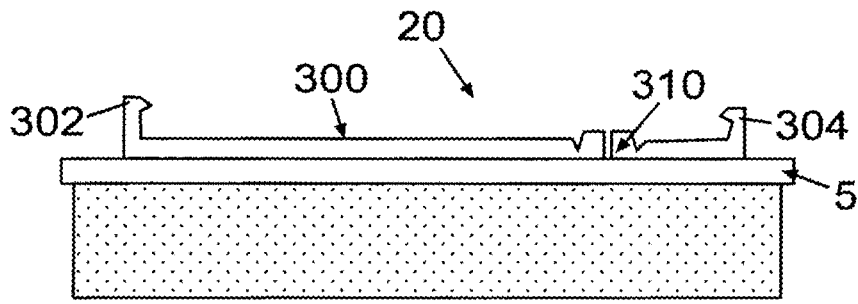
FIGS. 4a-b schematically illustrate an exemplary cradle unit, according to some embodiments of the present invention.
Figure 4B:
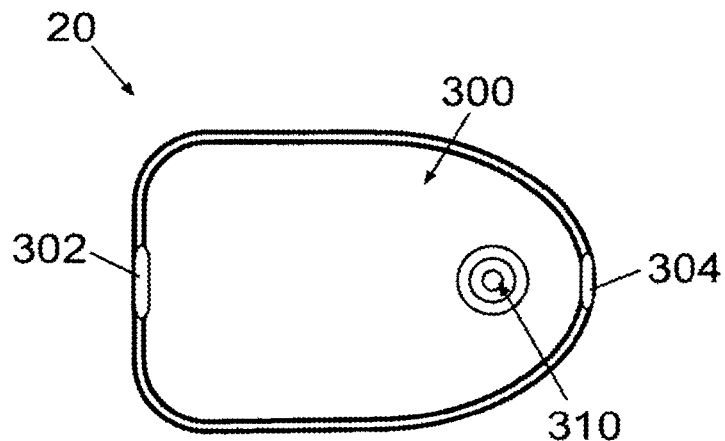

FIGS. 4a-b are side and upper views, respectively, of the cradle unit (20). The cradle unit (20) includes the following elements:
  a cradle base (300) configured as a flat sheet with an adhesive layer facing the skin (5) and provided with anchoring means (302), (304) on its upper side for connection and disconnection of the inserter and of the dispensing patch unit; and
  a well (310) configured as a tubular protrusion emerging upwardly from the cradle base (300) to allow alignment and appropriate connection between the cradle unit (20) and the inserter as well as between the cradle unit (20) and the dispensing patch unit (10) to allow for proper delivery of fluid from the dispensing patch unit (10) to the body.

Figure 4C:
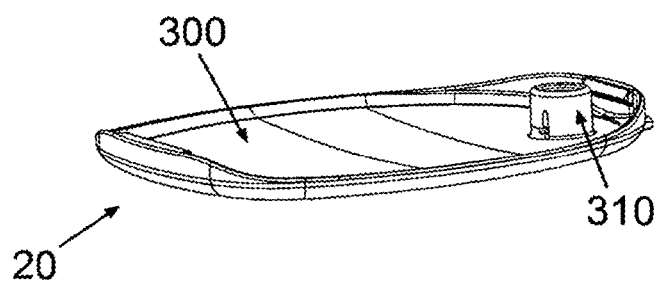
FIG. 4c is a perspective view of the cradle unit, according to some embodiments of the present invention.

FIG. 4c shows an exemplary cradle unit (20) having the cradle base (300) and the well (310).

Figure 5:
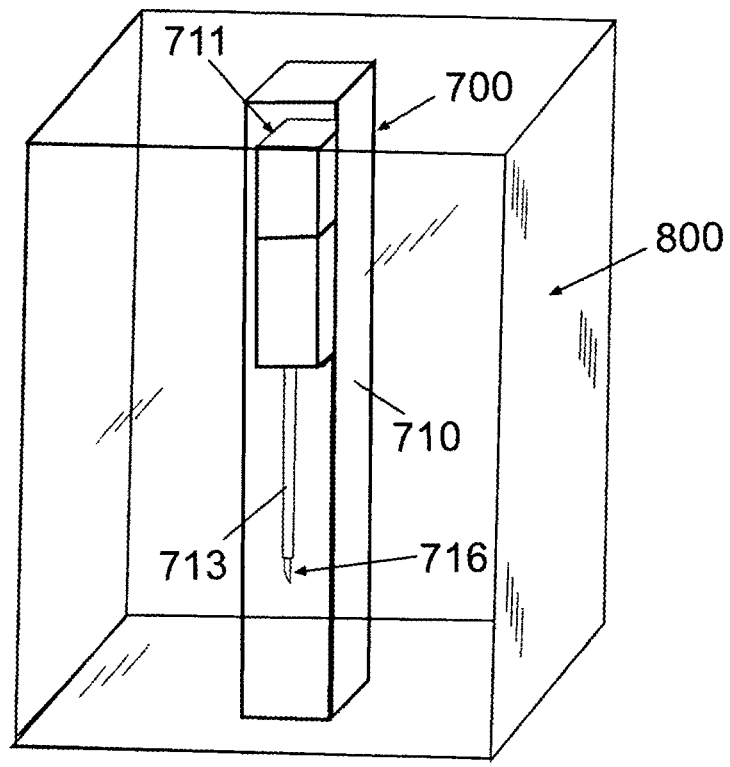
FIG. 5 schematically shows an exemplary inserter loaded with a cannula cartridge unit, according to some embodiments of the present invention.

FIG. 5 schematically shows an exemplary inserter (800) loaded with a cannula cartridge unit (700), according to some embodiments of the present invention. The cannula cartridge unit (700) includes a protector (710) and a penetrating cartridge (711). The penetrating cartridge (711) includes a cannula (713) that allows maintaining of fluid (e.g., insulin) delivery from the dispensing patch unit to the body and/or analyte (i.e., glucose) sensing/monitoring. The penetrating cartridge (711) further includes a penetrating member (716) for piercing the skin (5) and facilitating insertion of the cannula (713). The protector (710) has a protective cover that contains and further guards the cannula (713) and the penetrating member (716). One of the purposes of the protective cover is to prevent the user from unintentional skin piercing. As can be understood by one skilled in the art, the protector (710) can have any shape or size and can store a plurality of cannulae.

The inserter (800) allows either automatic or manual protraction of the cannula (713) and the penetrating member (716) from the protector (710) into the body of the (i.e., a hypodermic cannula insertion), as will be described in detail below. Once the cannula and the penetrating member are protracted from the protector (710), the penetrating member (716) pierces the skin (5), thereby allowing insertion of the cannula (713). After insertion, the cannula (713) continues to remain in the body and the penetrating member (716) can be retracted back into the protector (710). The insertion process terminates with the unloading of the protector (710) (with the penetrating member (716) disposed inside) from the inserter (800) and disposal of the protector (710).

It will be noted that in embodiments where the protector (710) is not used, the penetrating cartridge (711) alone is disposed within the inserter (800). Thus, the insertion process can be carried out as disclosed in co-owned, co-pending International Patent Application No. PCT/IL07/001454, filed Nov. 26, 2007, claiming priority to U.S. Provisional Patent Application No. 60/861,345, filed Nov. 28, 2006, and U.S. patent application Ser. No. 12/004,837, and International Patent Application No. PCT/IL07001578, both filed Dec. 20, 2007 and both claiming priority to U.S. Provisional Patent Application No. 60/876,679, filed Dec. 22, 2006, the disclosures of which are incorporated herein by reference in their entireties.

Figure 6A:
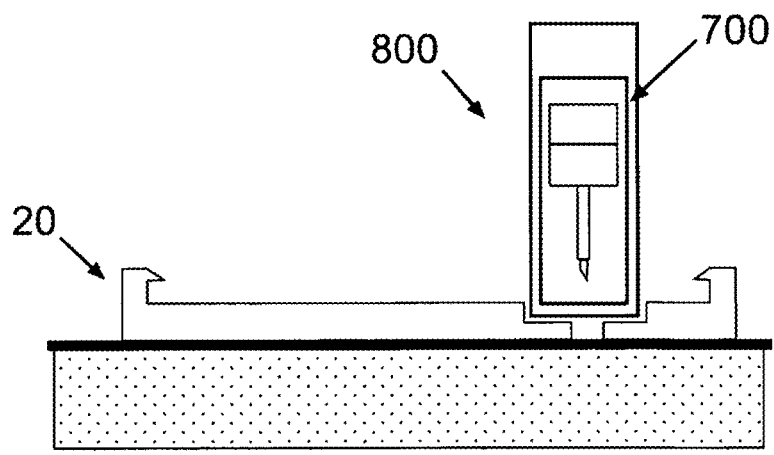
FIGS. 6a-c show an exemplary inserter connected to the cradle unit (as illustrated in FIG. 6a), a well assembly (as illustrated in FIG. 6b), or an infusion set (as illustrated in FIG. 6c), according to some embodiments of the present invention.
Figure 6B:
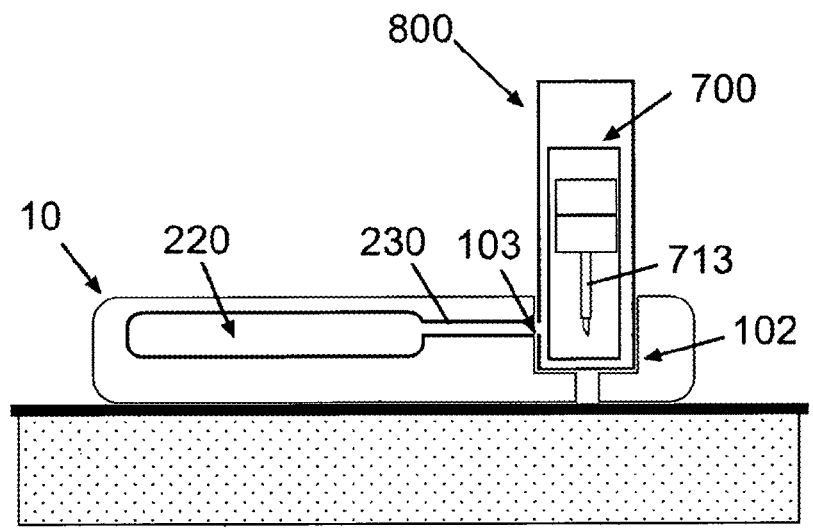
Figure 6C:
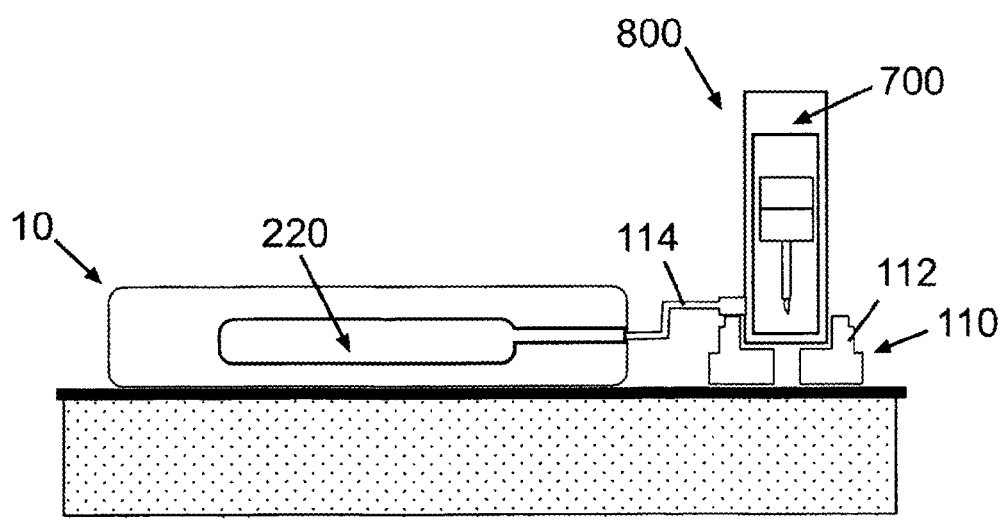

As illustrated in FIGS. 6a-c, the inserter can be connected to the cradle unit (20), or to a skin-adherable dispensing patch unit using either a well assembly or an infusion set. The inserter can also be connected to an infusion set used with a non-adherable dispensing device (e.g., "pager-like"). Referring to FIG. 6a, the inserter (800) is loaded with the cannula cartridge unit (700) and connected to the cradle unit (20). After cannula insertion process is completed, the inserter (800) can be disconnected from the cradle unit (20), and the dispensing patch unit can be connected to the cradle unit (20). FIG. 6b shows the inserter (800) loaded with the cannula cartridge unit (700) and connected to a well assembly (102) located in the dispensing patch unit (10). As can be understood by one skilled in the art, the dispensing patch unit can be either a single part unit or a two-part unit, as discussed above. The well assembly (102) includes an inlet port (103) on its side to allow passage of dispensed fluid from a reservoir (220) (disposed inside the dispensing unit (10)) via the delivery tube (230) to the cannula (713). In some embodiments, the cannula (713) includes a lateral opening through which fluid passes via the cannula into the body of the user. FIG. 6c shows the inserter (800) loaded with the cannula cartridge unit (700) and connected to an infusion set (110). The infusion set (110) includes a hub (112) and a short connecting tube (114) extending from the dispensing patch unit (10) to a proximate insertion site. The connecting tube (114) allows for fluid communication between the reservoir (220) of the unit (10) and the cannula (713).

Figure 7A:
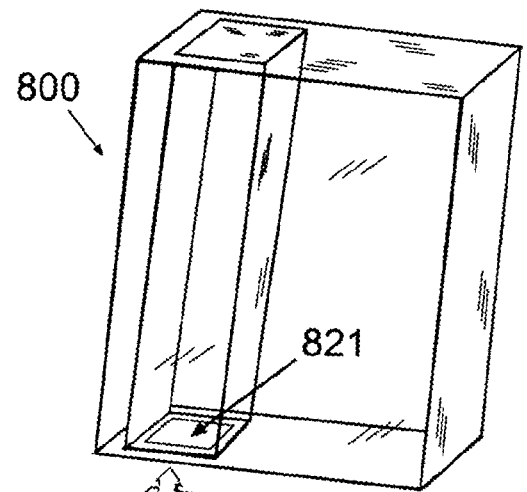
FIGS. 7a-c show various exemplary ways of loading an exemplary cannula cartridge unit into the inserter, according to some embodiments of the present invention.
Figure 7A:
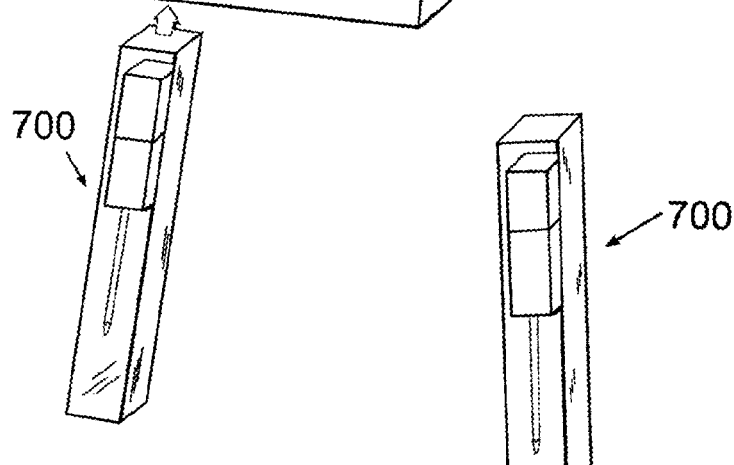
Figure 7B:
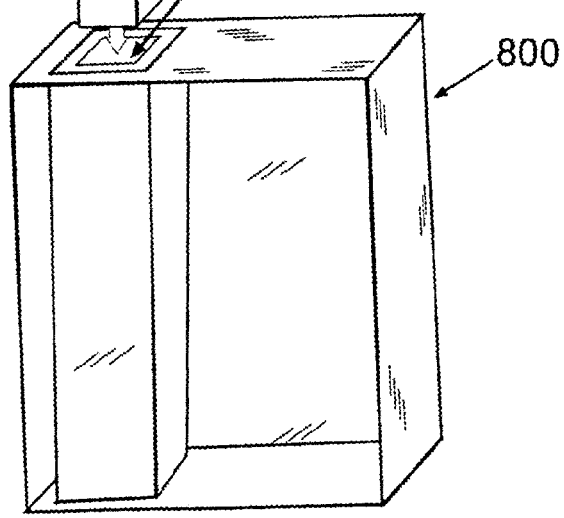
Figure 7C:
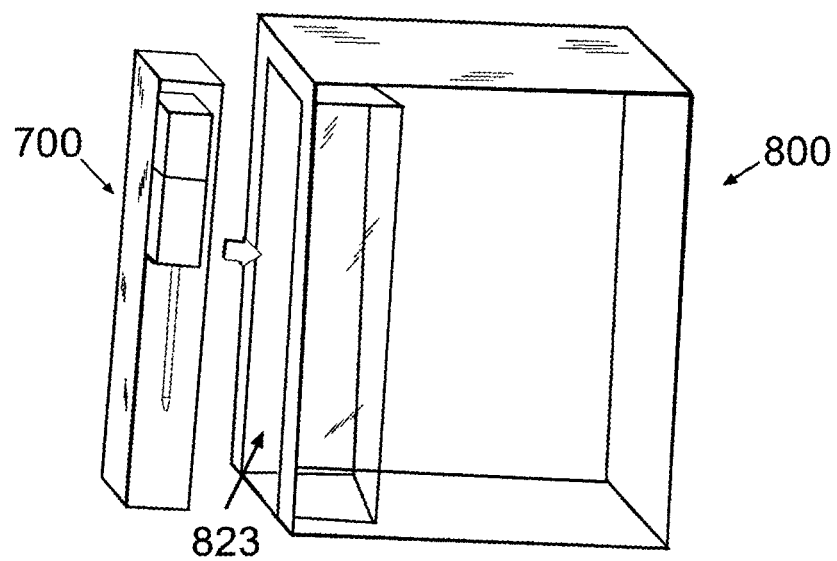

FIGS. 7a-c show various ways of loading the cannula cartridge unit (700) into the inserter (800). The cannula cartridge unit (700) can be loaded into the inserter (800) through a bottom opening (821) in the inserter (800) (as shown in FIG. 7a), an upper opening (822) in the inserter (800) (as shown in FIG. 7b), or a lateral opening (823) in the inserter (800) (as shown in FIG. 7c). As can be understood by one skilled in the art, the unit (700) can be placed into the inserter (800) in any other fashion and such placement is not limited to the embodiments shown in FIGS. 7a-c.

Figure 8A:
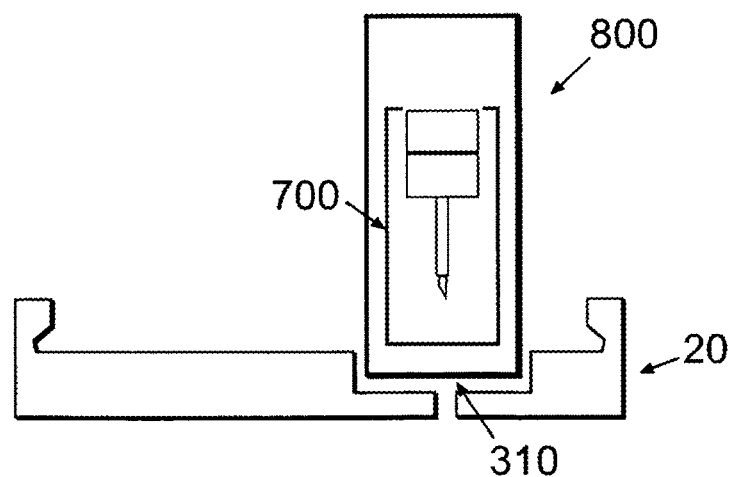
FIGS. 8a-b show exemplary inserters loaded with the cannula cartridge unit, according to some embodiments of the present invention.
Figure 8B:
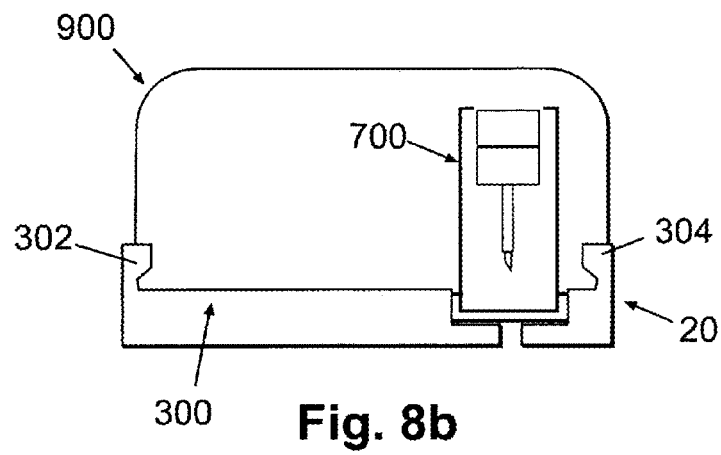

Various types of inserters can be loaded with the cannula cartridge unit (700). FIG. 8a schematically shows an inserter configured as a pen (800) (hereinafter, referred to as "pen-like") coupled to a cradle unit (20) via the well (310). FIG. 8b schematically shows an inserter configured as a "computer mouse" (900) (hereinafter, referred to as "mouse-like") coupled to the cradle unit (20) using anchoring means (302), (304) provided on the upper face of the cradle base (300). The anchoring means (302), (304) can be latches, snap-fit mechanisms, VELCRO® devices, etc. As can be understood by one skilled in the art, the examples shown in FIGS. 8a-b are provided here for illustrative, non-limiting purposes only and the present invention can be used with any types of inserters into which the cannula cartridge unit (700) can be loaded. Other inserter configurations are fully contemplated as being within the scope of embodiments of the present invention.

Figure 9A:
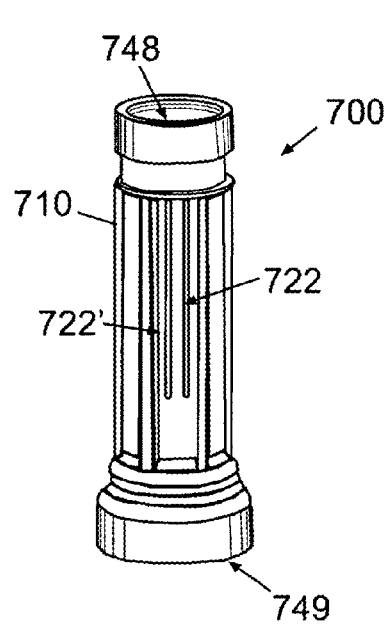
FIGS. 9a-b are perspective and cross-sectional views, respectively, of the cannula cartridge unit, according to some embodiments of the present invention.

FIG. 9a is a perspective view of the exemplary cannula cartridge unit (700), according to some embodiments of the present invention. The unit (700) includes the protector (710). The protector (710) includes a bottom opening (749) and an upper opening (748). The bottom opening (749) is configured and dimensioned to fit either over a well assembly (not shown in FIG. 9a) or over an infusion set hub (not shown in FIG. 9a) or over a well which is a part of the cradle unit (not shown in FIG. 9a). Insertion of the cannula (713) is carried out by protracting the penetrating automatically. The protraction can be done using a dedicated rod inserted through the protector's upper opening (748) or using dedicated engagement hooks provided in the inserter and configured to penetrate the protector (710) through at least one longitudinal slit (722), (722') provided in the main body portion of the protector, as will be described in detail below. As can be understood by one skilled in the art, a single protector can accommodate placement of cannulae and/or sensors having various shapes and/or sizes (length, width, height, etc.). An example of such protector is disclosed in co-pending, co-owned International Patent Application No. PCT/IL2008/000861 and U.S. patent application Ser. No. 12/215,219, entitled "Portable Infusion Pump with Cannula Inserter and Pain Reduction Mechanism" and "Protector Mechanism," respectively, and claiming priority to U.S. Provisional Patent Application No. 60/937,155, filed on Jun. 25, 2007, the disclosures of which are incorporated herein by reference in their entireties. Thus, the same inserter can be used for inserting into the body cannulae and/or sensors with variable shapes and/or sizes.

Figure 9B:
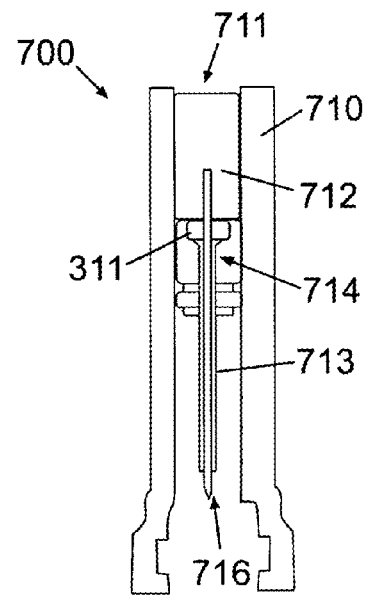

FIG. 9b is a cross-sectional view of the exemplary cannula cartridge unit (700) having the protector (710) and the penetrating cartridge (711), according to some embodiments of the present invention. In some embodiments, the penetrating cartridge (711) has the following elements: the penetrating member (716) having a grip portion (712) located at the blunt end of the penetrating member (716), the cannula (713) and a cannula hub (714) attached to the cannula (713) and containing a rubber septum (311) for maintaining the upper opening of the cannula (713) sealed upon insertion of the cannula into the body. The septum (311) can be pierced repeatedly by a connecting lumen (not shown in FIG. 9b) provided in the disposable part of the dispensing patch unit. The connecting lumen maintains fluid communication between the reservoir (not shown in FIG. 9b) and the cannula (713).

The cannula insertion process can be carried out either manually (i.e., both the cannula insertion and the penetrating member retraction are performed manually), semi-automatically (i.e., the cannula insertion is automatic while the penetrating member retraction is manual or vice versa), or fully automatic (i.e., both the cannula insertion and the penetrating member retraction are performed automatically). The following figures illustrate in detail various types of insertion processes.

Figure 10A:
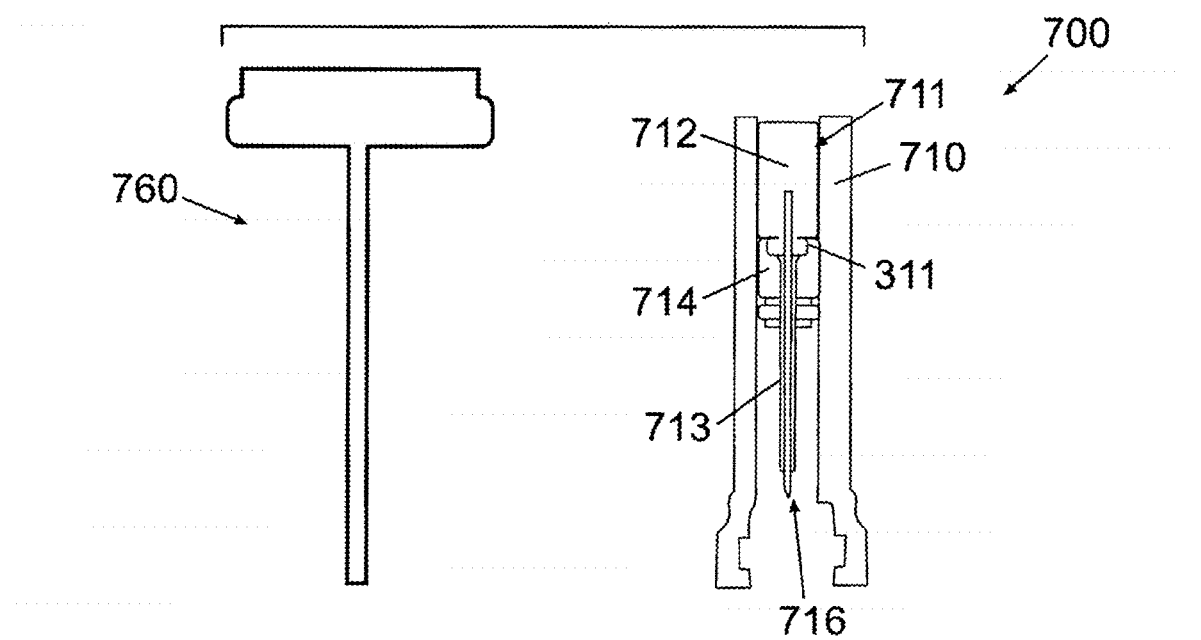
FIGS. 10a-i are cross-sectional views of the cannula cartridge unit during manual cannula insertion process, according to some embodiments of the present invention.
Figure 10B:
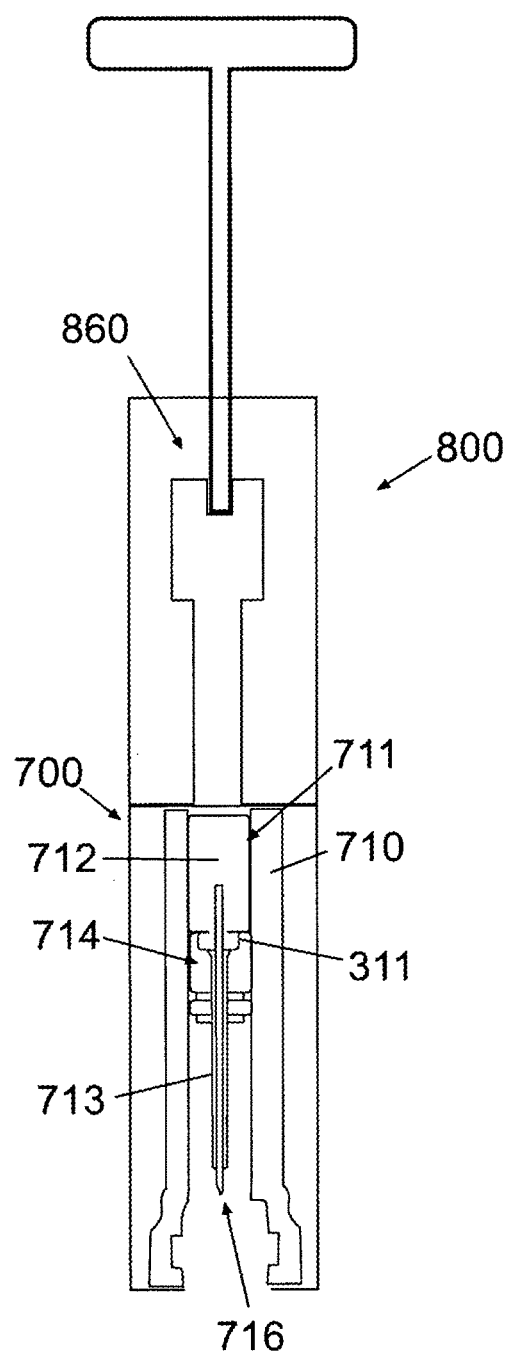

FIGS. 10a-i are cross-sectional views of the inserter (800) being loaded with the cannula cartridge unit during a manual insertion process, according to some embodiments of the present invention. Manual insertion can be carried out either using the cannula cartridge unit (700) as a stand-alone item with the aid of a rod (760), as shown in FIG. 10a. In some embodiments, the manual insertion process can be carried out using the inserter (800) preloaded with the cannula cartridge unit (700) and using a rod (860), as shown in FIG. 10b. The insertion process in both embodiments is similar.

Figure 10C:
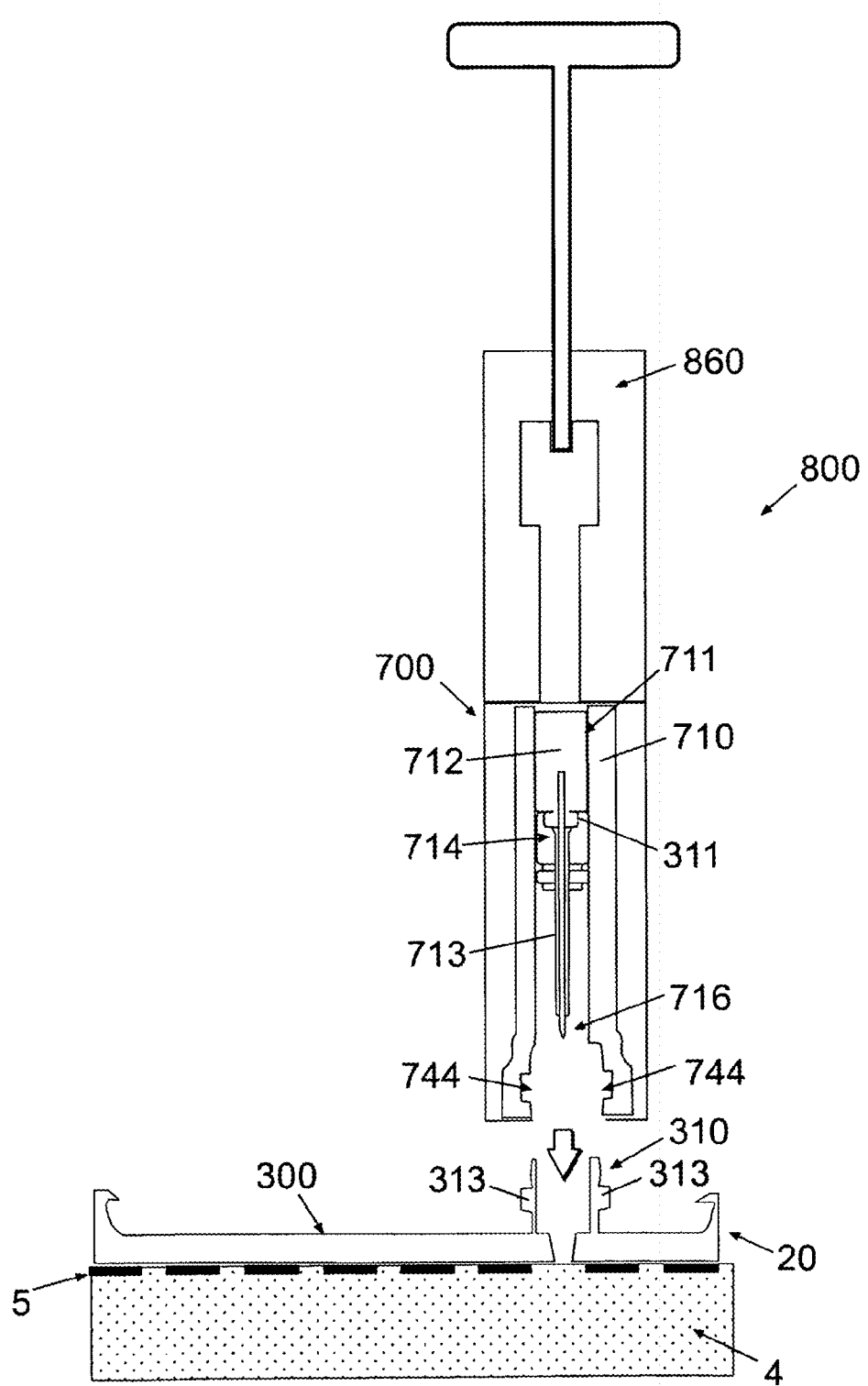
Figure 10D:
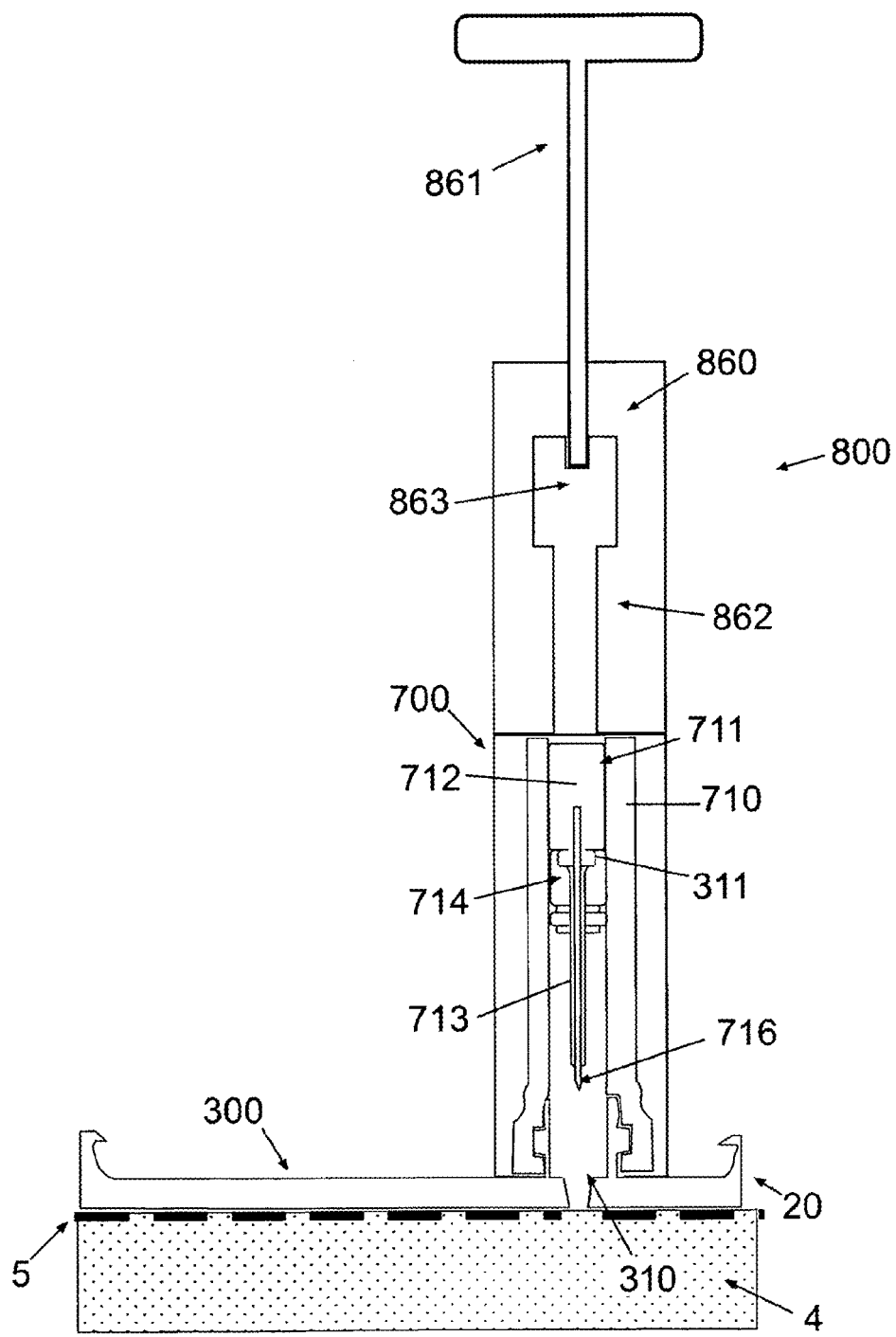

FIGS. 10c-i illustrate an exemplary insertion process using the inserter (800) connectable to the skin adherable cradle unit (20). FIG. 10c shows the inserter (800) loaded with the cannula cartridge unit (700) and the cradle unit (20) prior to its connection to the inserter (800) and the cannula cartridge unit (700). The cradle unit (20) includes the well (310) disposed in the base (300) and having a snapping engagement mechanism with at least one resistance loaded latch (313). The cannula cartridge unit (700) includes at least one notch or recess (744) that corresponds and is configured to accommodate insertion of the latch (313). As discussed above, the cannula cartridge unit (700) is placed over the well (310), thereby snapping the notch (744) over the latch (313) and therefore locking the unit (700) to the well (310). As can be understood by one skilled in the art, other ways of securing the unit (700) to the well (310) are possible. In some embodiments, the cannula cartridge unit (700) can be only placed over a well (310) without being connected to the well (310). The connection between the cannula cartridge unit (700) and the well (310) when the unit (700) is brought toward the well (310) is as illustrated by the arrow in FIG. 10c. In some embodiments the connection is established between the inserter (800) and the cradle unit (300). The cannula cartridge unit (700) can be placed over the well, or it may not come in contact with the cradle unit (300) at all. FIG. 10d shows the inserter (800) connected to a cradle unit (20) and ready for operation. The dedicated rod (860) is disposed outside the top end of the inserter (800).

The rod (860) can include a handle (861) and a push rod portion (862) that can be located opposite the handle (861). The cannula cartridge unit (700) includes the penetrating cartridge (711) having the grip portion (712) that interacts with the push rod portion (862) of the rod (860). The push rod portion (862) can include a recessed portion (863) at its top that accommodates placement of the handle (861). The recessed portion (863) secures the handle (861) and prevents wobbling of the handle (861) when the latter is being pushed down the cannula cartridge unit (700). In another embodiment, the handle and the push rod portion are configured to constitute a single item.

Figure 10E:
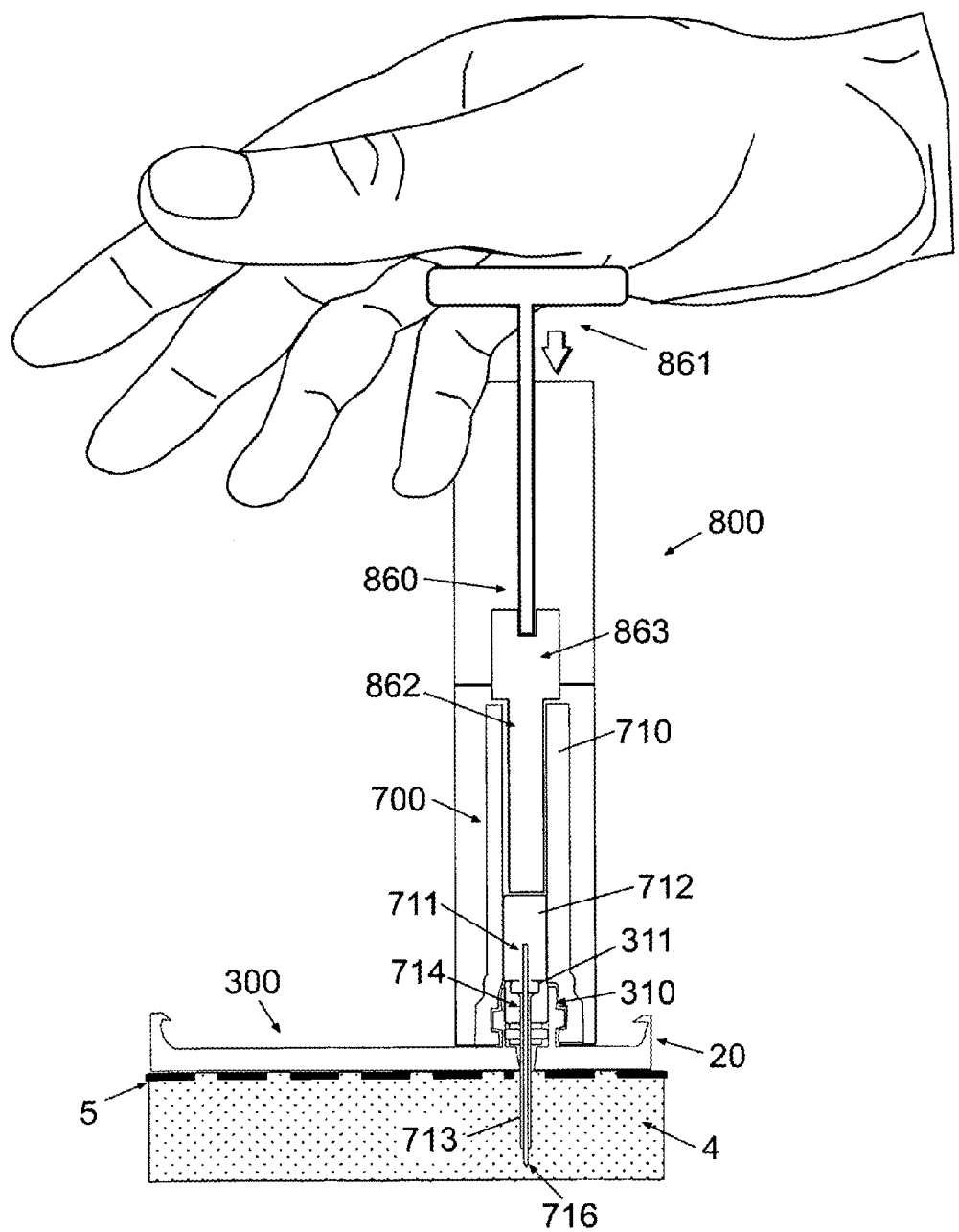

FIG. 10e shows the penetrating cartridge (711) being pushed down by the dedicated rod (860) through the well (310) and into the subcutaneous tissue (4) of the user. The user pushes on the handle (861) of the rod (860) to thrust the rod (860) in a downward direction toward the well (310). The force that the user applies to the handle (861) of the rod (860) is transferred to the push rod portion (862), which pushes the penetrating cartridge (711) down toward the skin (5) of the user. As the penetrating cartridge (711) is pushed down, the penetrating member (716) contained within the penetrating cartridge (711) pierces the skin (5) of the user and enters the subcutaneous tissue (4). Along with the entry of the penetrating member (716), the cannula (713) is also inserted into the subcutaneous compartment (4). Once the cannula (713) is inserted, the penetrating member (716) can be removed.

Figure 10F:
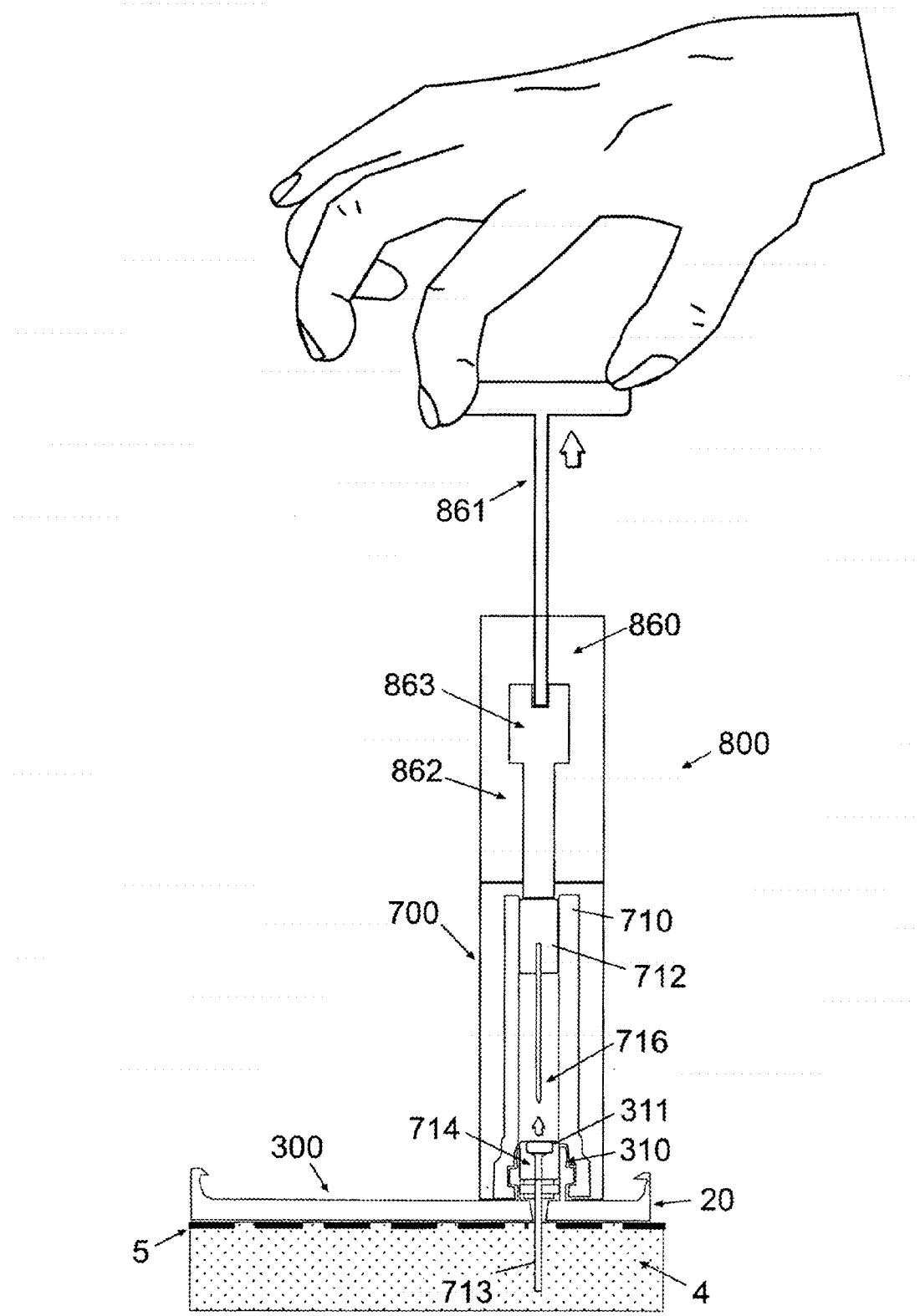

FIG. 10f shows the penetrating member's (716) retraction back into the protector (710) using of the rod (860). Once the cannula (713) is inserted into the subcutaneous tissue (4), the cannula hub (714) remains rigidly connected to the well (310). To remove the penetrating member (716), the user pulls on the handle (861) of the rod (860) in an upward direction (or direction opposite to the direction of insertion). Since the handle (861) of the rod (860) is secured to the recessed portion (863) of the push rod portion (862) and the push rod portion (862) is secured to the grip portion (712) that is able to slide back and forth inside the protector (710) and the inserter (800), upon pulling of the handle, the push rod portion (862) of the rod (860) and the grip portion (712) are pulled along with the handle (861), thereby removing the penetrating member (716) from the subcutaneous compartment (4) and from the cannula hub (714). In some embodiments, the inserter (800) and/or the protector (710) can include stoppers at its top end to prevent accidental removal of the push rod portion (862) and the grip portion (712). Additionally, the inserter's and/or protector's interior portions can include interior stoppers to prevent excessive insertion of the penetrating member (716) and accidental slip out of the penetrating member (716) along with the grip portion (712) from the bottom end of the protector (710) once it is disengaged from the well (310). In some embodiments, the well (310) can serve as a stopper to prevent excessive insertion of the penetrating member (716). Once the penetrating member (716) is removed, the inserter (800), including the protector (710) with the penetrating member (716) disposed within can be disengaged from the well (310).

Figure 10G:
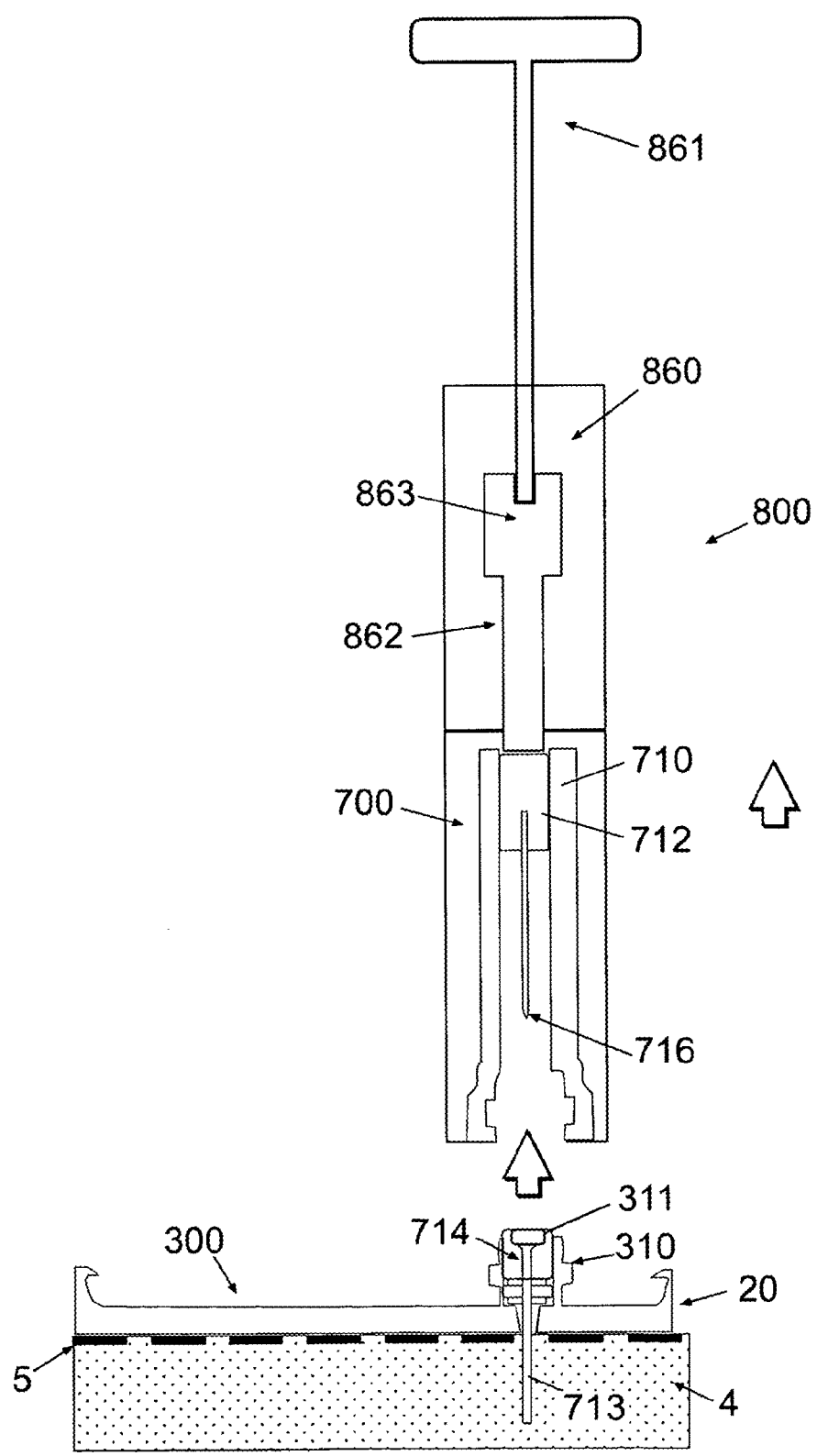

FIG. 10g shows disconnection of the inserter (800) from the cradle unit (20). The inserter (800) is removed by disengaging the notches (744) from the latches (313). This can be done by pulling the notches (744) away from the latches (313) or by pushing a button that pulls the notches (744) out, or using any other means. Upon being removed from the cradle unit (300), the inserter (800) continues to conceal the penetrating member (716) inside the protector (710) along with the penetrating member's grip portion (712). In some embodiments, the handle (861) can be disengaged from the recessed portion (863) and the inserter (800) along with its contents can then be disposed. The handle (861) can be reused for future cannula insertions. In other embodiments, upon the inserter's removal from the cradle unit (300), the protector (710) with the penetrating member (716) disposed within can be unloaded from the inserter (800) and disposed. The inserter (800) can be reused for future cannula insertions. As can be understood by one skilled in the art, the inserter (800) can be disconnected from the cradle unit (20) after inserting the cannula (713) while the penetrating member (716) remains inside the body. In this case, the user can manually remove the penetrating member (716) from the body by holding the grip portion (712) of the penetrating member (716) with his/her fingers and pulling it in an upward direction (or direction that is opposite to the direction of insertion).

Figure 10H:
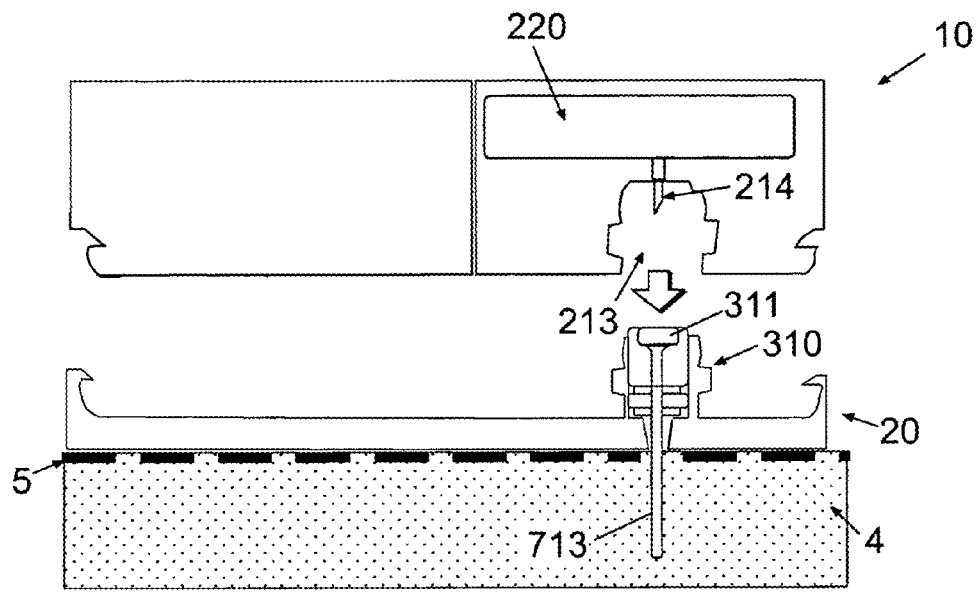

FIG. 10h shows a two-part dispensing patch unit (10) prior to its connection to the cradle unit (20). The dispensing patch unit (10) contains, inter alia, a fluid reservoir (220), an outlet port (213) and connecting lumen (214) that maintains fluid communication between the reservoir (220) and the outlet port (213). Upon connection of the dispensing patch unit (10) to the cradle unit (20), the connecting lumen (214) pierces a septum (311) which seals the upper opening of the cannula (713), thus allowing fluid delivery via the cannula (713) to the subcutaneous tissue (4). The outlet port (213) allows repetitive connection and disconnection of the dispensing patch unit (10) to and from the cradle unit (20).

Figure 10I:
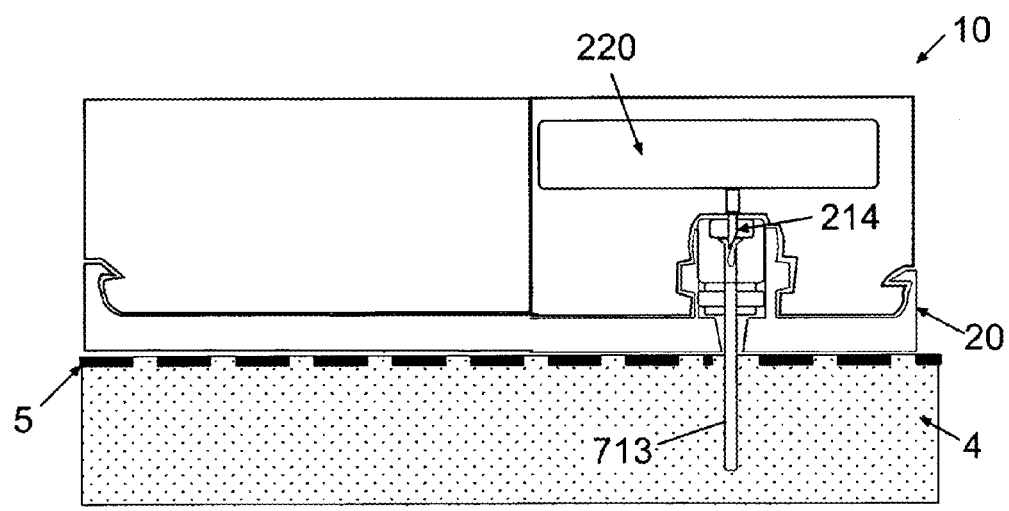

FIG. 10i shows a two-part dispensing patch unit (10) after it has been connected to the cradle unit (20). In some embodiments, the fluid (e.g., insulin) delivery cannula (713) may contain also a sensor for monitoring a body analyte (e.g. glucose). Fluid delivery can be adjusted according to sensor inputs (in semi or fully closed-loop mode). In another embodiment, the dispensing patch unit (10) can include both a cannula (713) for drug delivery and a sensor for analyte sensing, as described in co-owned, co-pending International Patent Application No. PCT/IL07/000163 and U.S. patent application Ser. No. 11/706,606, U.S. patent application Ser. No. 11/963,481 and International Patent Application No. PCT/IL07/001579, and U.S. patent application Ser. No. 12/116,546 and International Patent Application No. PCT/US08/62928, filed May 7, 2008, claiming priority to U.S. provisional patent application No. 60/928,054, filed May 7, 2007, and entitled "A Reciprocating System for Monitoring Analyte Concentrations and\or Dispensing Fluids into a Body", the disclosures of which are incorporated herein by reference in their entireties.

Figure 11A:
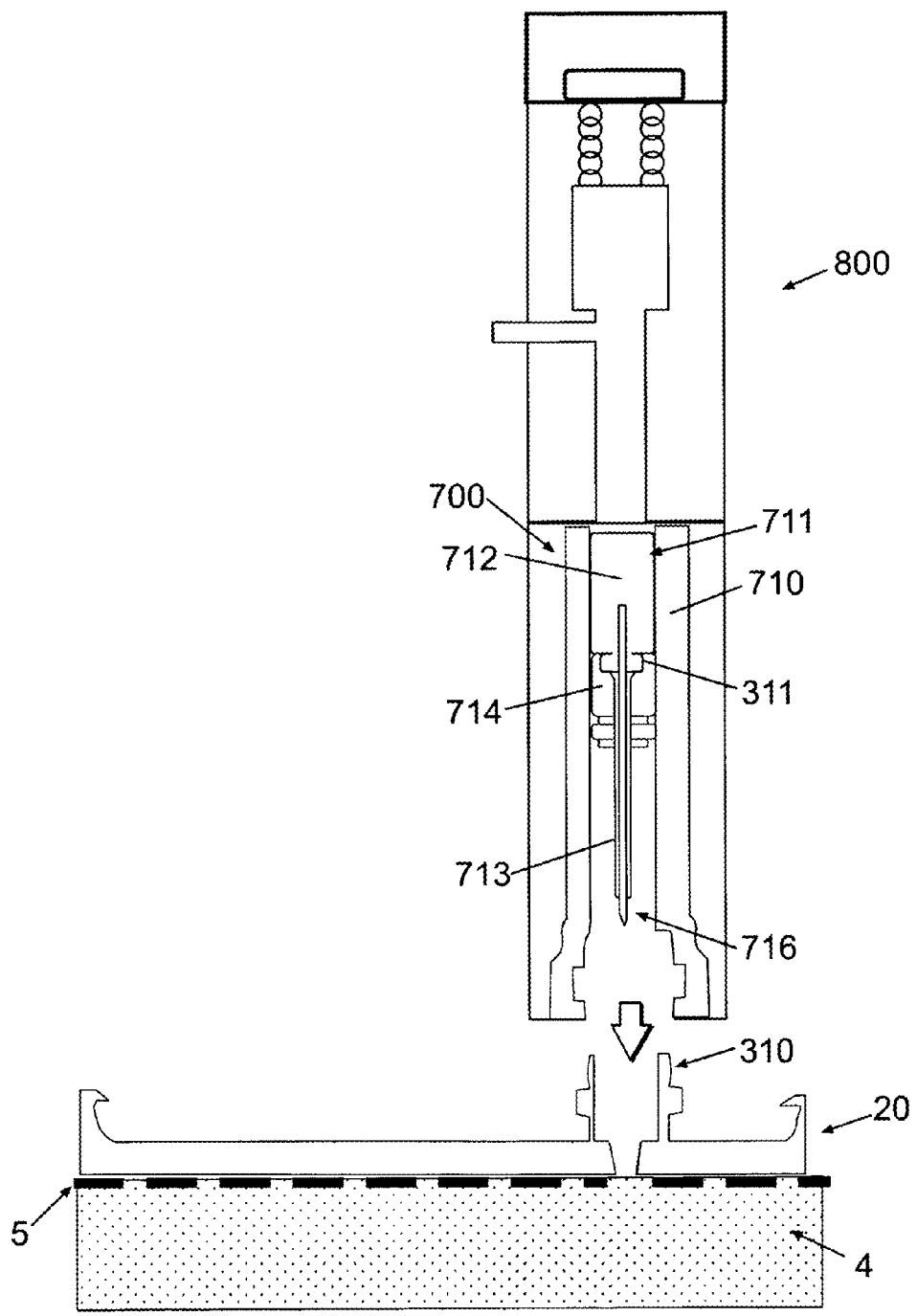
FIGS. 11a-e are cross-sectional views of the cannula cartridge unit during a semi-automatic cannula insertion process, according to some embodiments of the present invention.

FIGS. 11a-e are cross-sectional views of the inserter (800) being loaded with the cannula cartridge unit (700) during a semi-automatic insertion process, according to some embodiments of the present invention. FIG. 11a shows the inserter (800) loaded with the cannula cartridge unit (700), and the cradle unit (20) prior to connection. The connection between the cannula cartridge unit (700) and the cradle unit (20) is established as discussed above with reference to FIG. 10c. In some embodiments, the inserter (800) can include a spring-loaded mechanism that is couplable to the grip portion (712) and upon release of the spring, pushes on the grip portion (712) to force insertion of the penetrating member (716) along with the cannula (716) into the subcutaneous tissue (4), as will be discussed below.

Figure 11B:
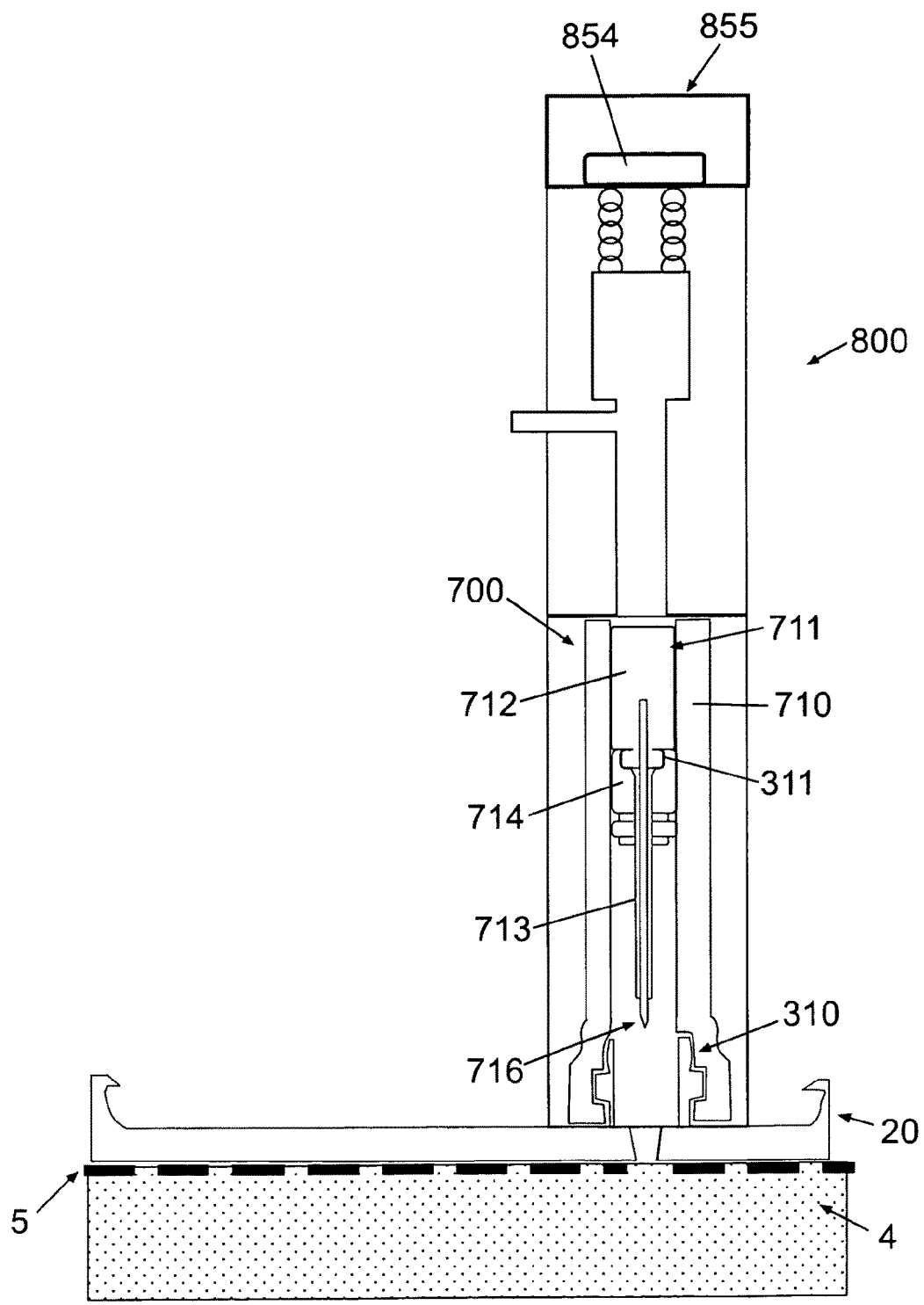

FIG. 11b shows an inserter (800) loaded with a cannula cartridge unit (700) connected to a cradle unit (20) and ready for operation. In some embodiments, the inserter (800) includes means for preventing inadvertent or premature release/firing of the cannula (713). Such means could be, for example, a safety cap (855) which shields the release button (854) and is removable from the inserter (800) upon connection of the inserter to the cradle unit (20) and prior to insertion initiation.

Figure 11C:
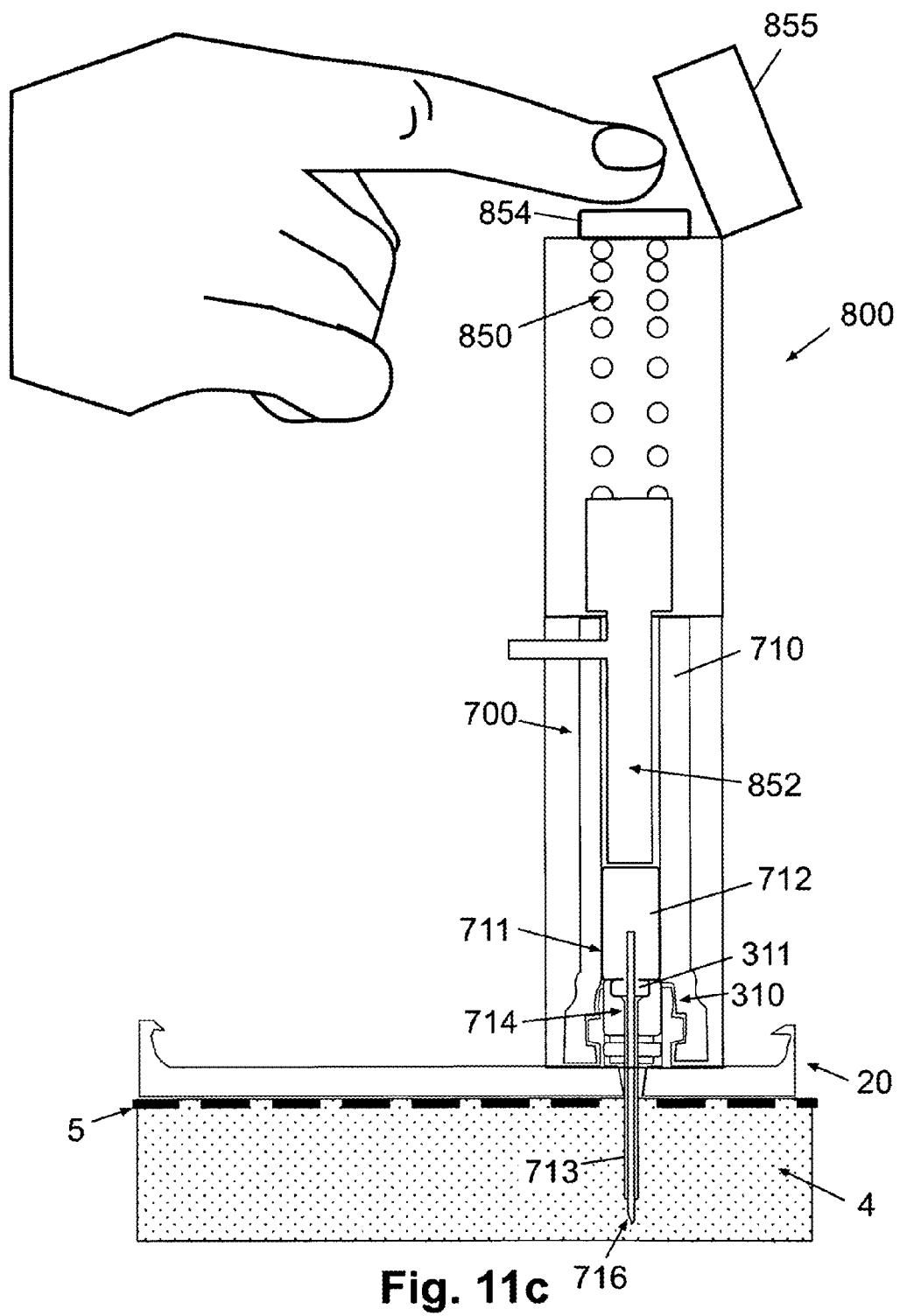

FIG. 11c shows how the user is lifting the safety cap (855) and pressing the release button (854). The inserter (800) can be connected to the well (310) in a fashion similar to the connection of the cannula cartridge unit (700) to the well (310) (e.g., using the latch-notch connection). The penetrating cartridge (711) is consequently pushed down automatically towards the well (310), for example by a rod (852), which is displaceable by biased spring (850). A stated above, the inserter (800) includes a spring-loaded mechanism having a spring (850) coupled to an advancing rod (852) and a spring release button (854). The spring (850) is initially in a compressed state, whereby the advancing rod (852) is disposed in a pre-firing position substantially near the top end of the inserter (800). The spring release button (854) is configured to cause release of the spring (850) in a downward direction (or direction toward the skin (5)). Once the button (854) is pressed, the spring (850) is released, as illustrated in FIG. 11c. Release of the spring (850), causes the advancing rod (852) to apply pressure on the penetrating cartridge (711) thrusting it in a downward direction (or toward the skin (5)). Movement of the cartridge (711) causes movement of the penetrating member (716) and the cannula (713) toward the skin (5) through the well (310), thereby forcing piercing of the skin (5) and insertion of the penetrating member (716) and the cannula (713) into the subcutaneous compartment (4). After insertion of the cannula (713), the penetrating member (716) can be retracted or removed from the subcutaneous compartment (4).

Figure 11D:
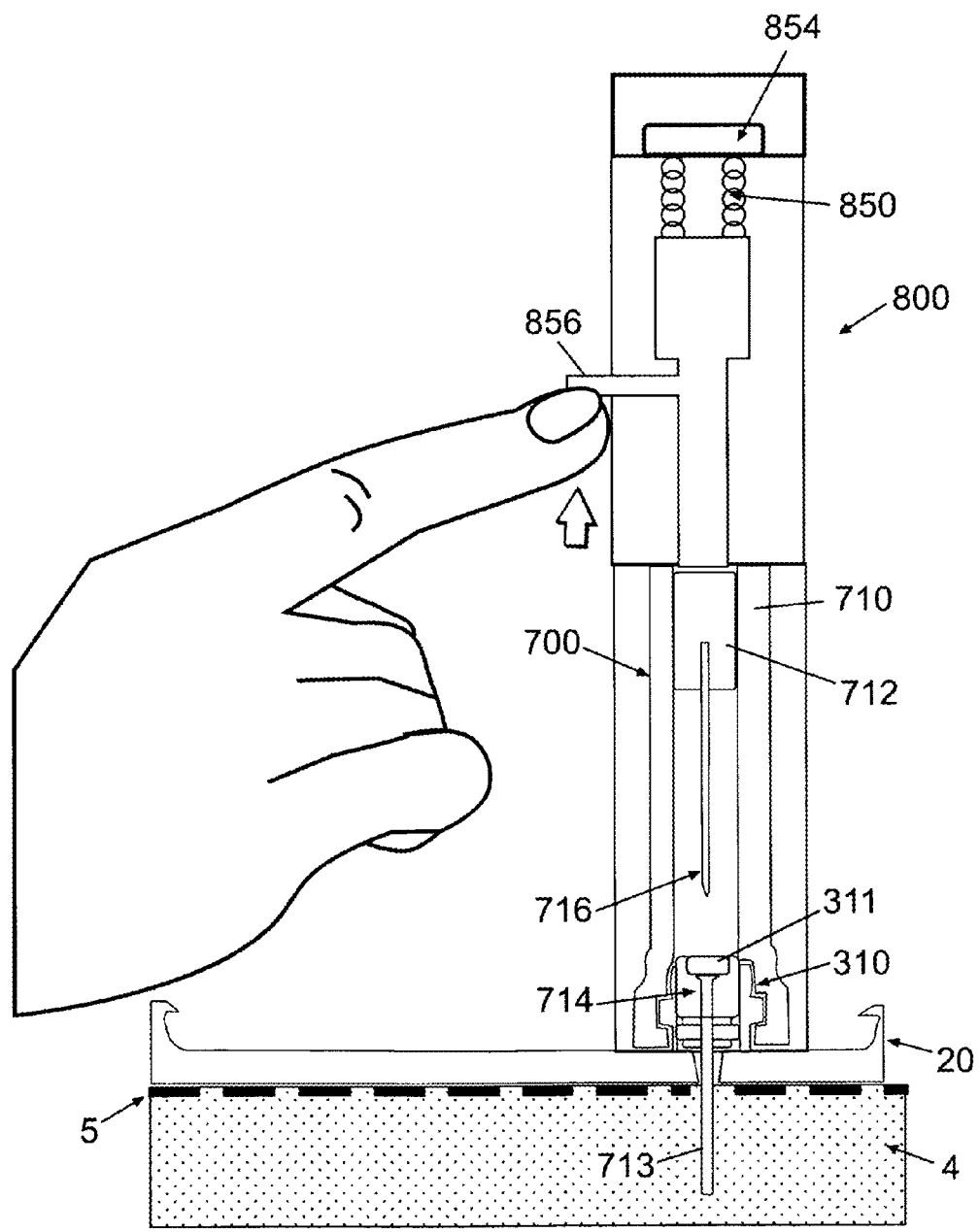

FIG. 11d shows the penetrating member's (716) manual retraction into the protector (710) by means of a lateral protrusion (856), for example. The lateral protrusion (856) is configured to move with the advancing rod (852) as it is forced downward during insertion process. To retract the rod (852) into its original position, and thus, retract the penetrating member (716) from subcutaneous compartment (4), the user can pull on the protrusion (856) in an upward direction (or direction opposite to direction of insertion) and secure the advancing rod (852) in the pre-firing position. Upon removal of the penetrating member (716), the cannula hub (714) remains secured at the well (310), and the cannula (713) remains within the subcutaneous tissue (4). Upon removal of the penetrating member (716), the inserter (800) and the protector (710) can be disconnected from the well (310).

Figure 11E:
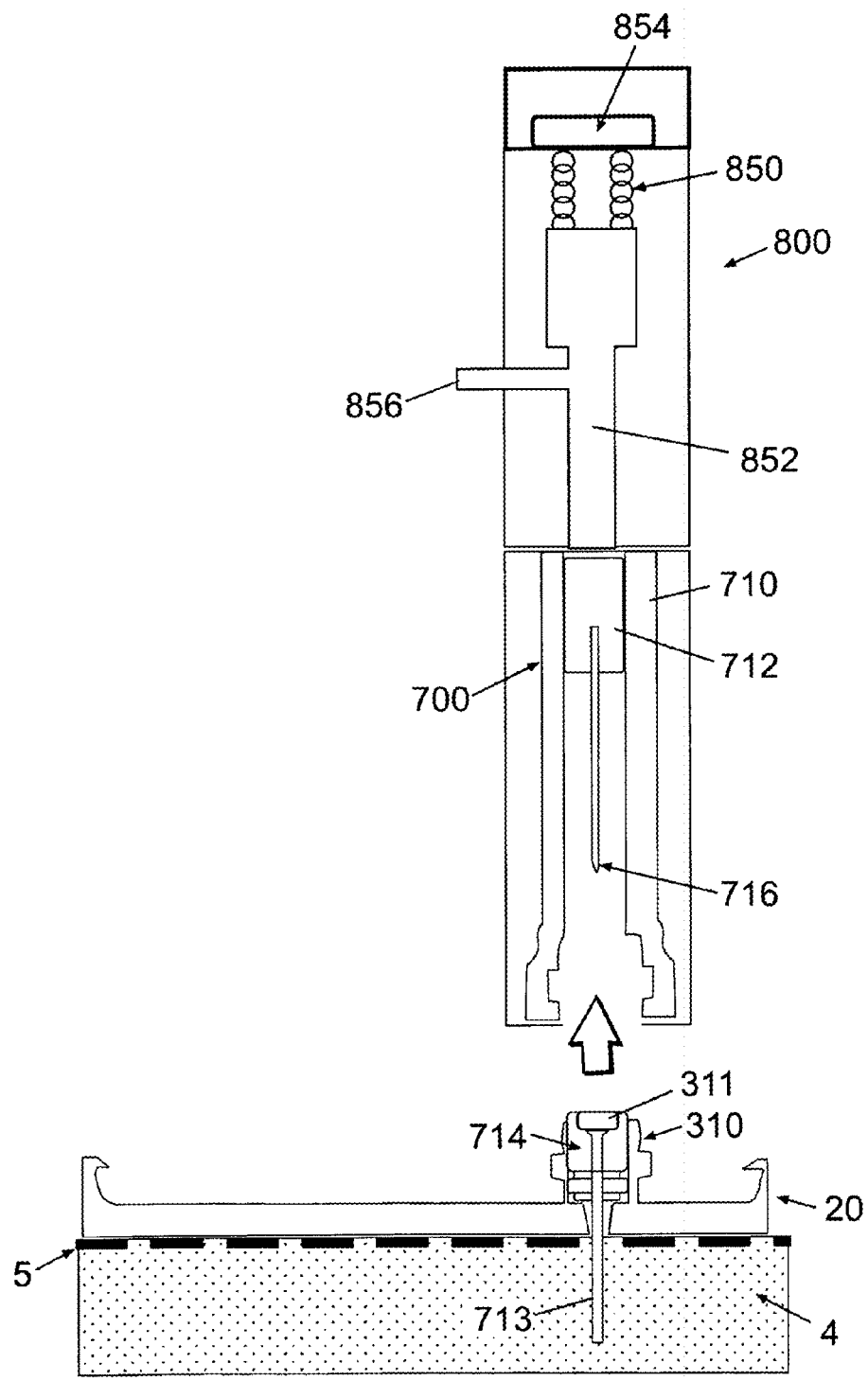

FIG. 11e shows disconnection of the inserter (800) from the cradle unit (20). Upon disconnection the protector (710), now containing only the penetrating member (716) and grip portion (712), is unloaded from the inserter (800) and then disposed of. As can be understood by one skilled in the art, the inserter (800) can otherwise be disconnected from the cradle unit (20) after the cannula (713) has been inserted while the penetrating member (716) remaining inside the body. In this case, the user manually removes the penetrating member (716) from the body by holding the grip portion (712) with his fingers and pulling it upwards together with the penetrating member (716). After disconnection of the inserter (800) from the cradle unit (20), a dispensing patch unit can be connected to the cradle unit, as previously described with reference to FIGS. 10h-i.

Figure 12A:
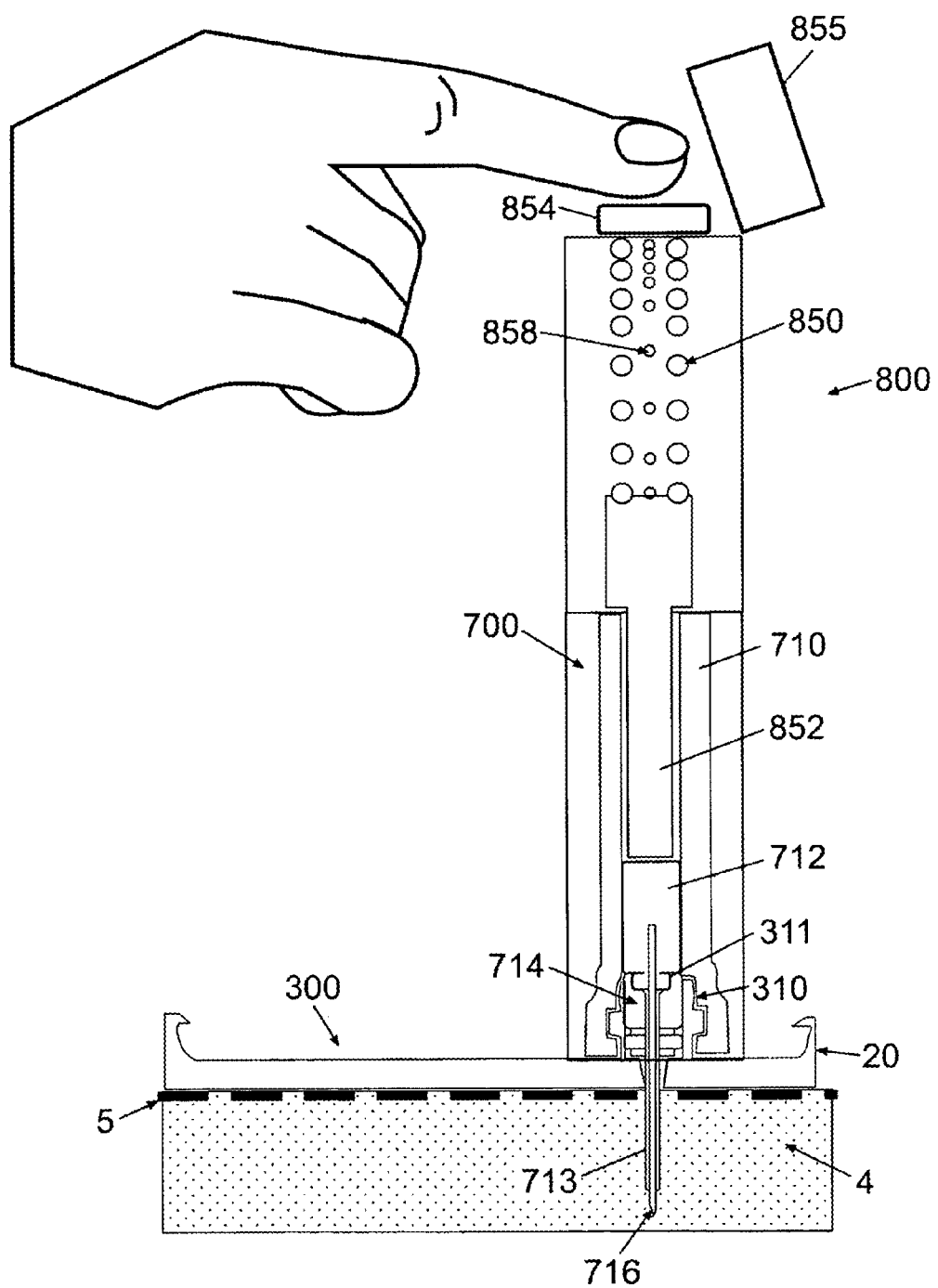
FIGS. 12a-c are cross-sectional views of the cannula cartridge unit during an automatic cannula insertion process, according to some embodiments of the present invention.
Figure 12B:
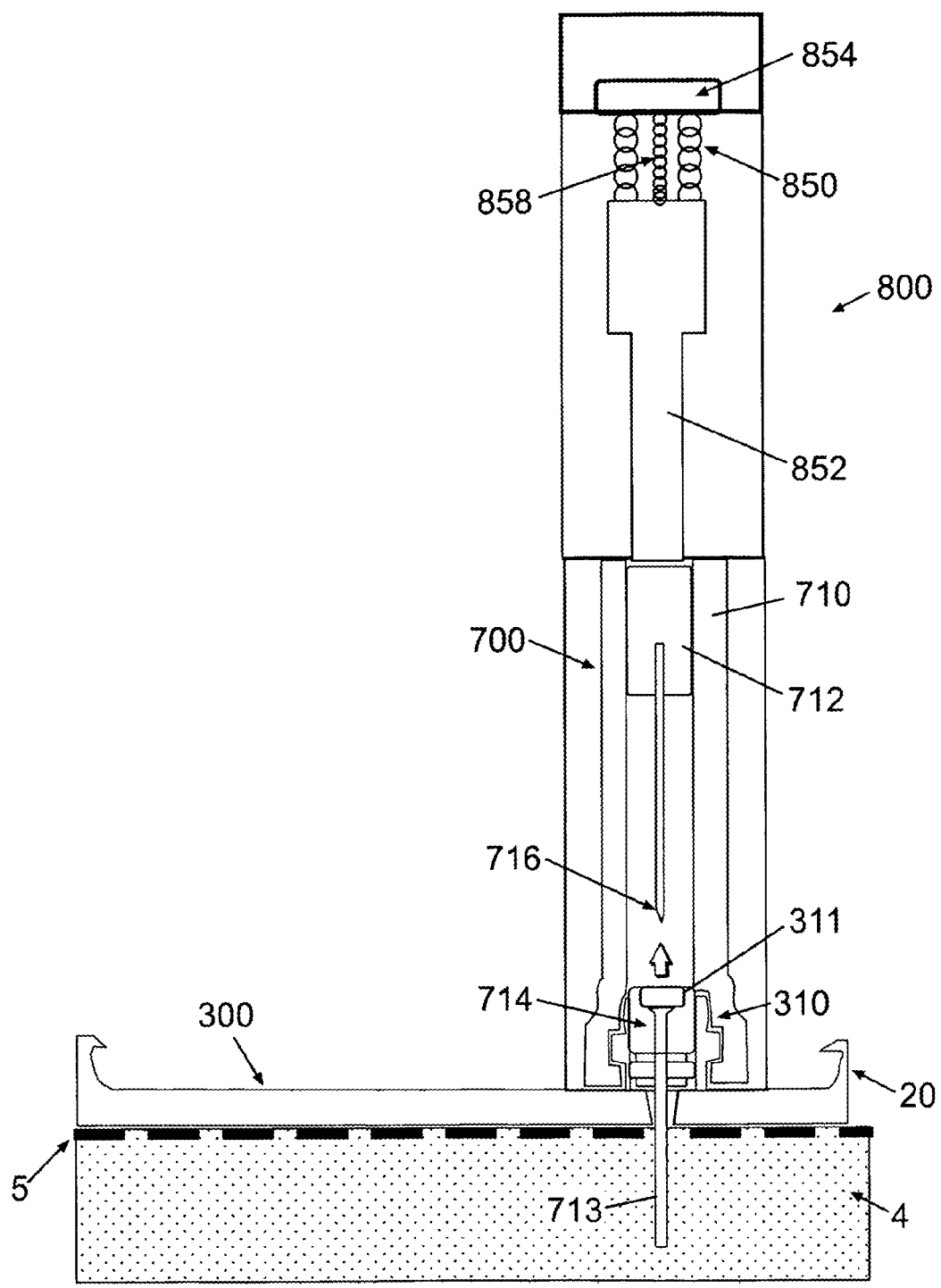
Figure 12C:
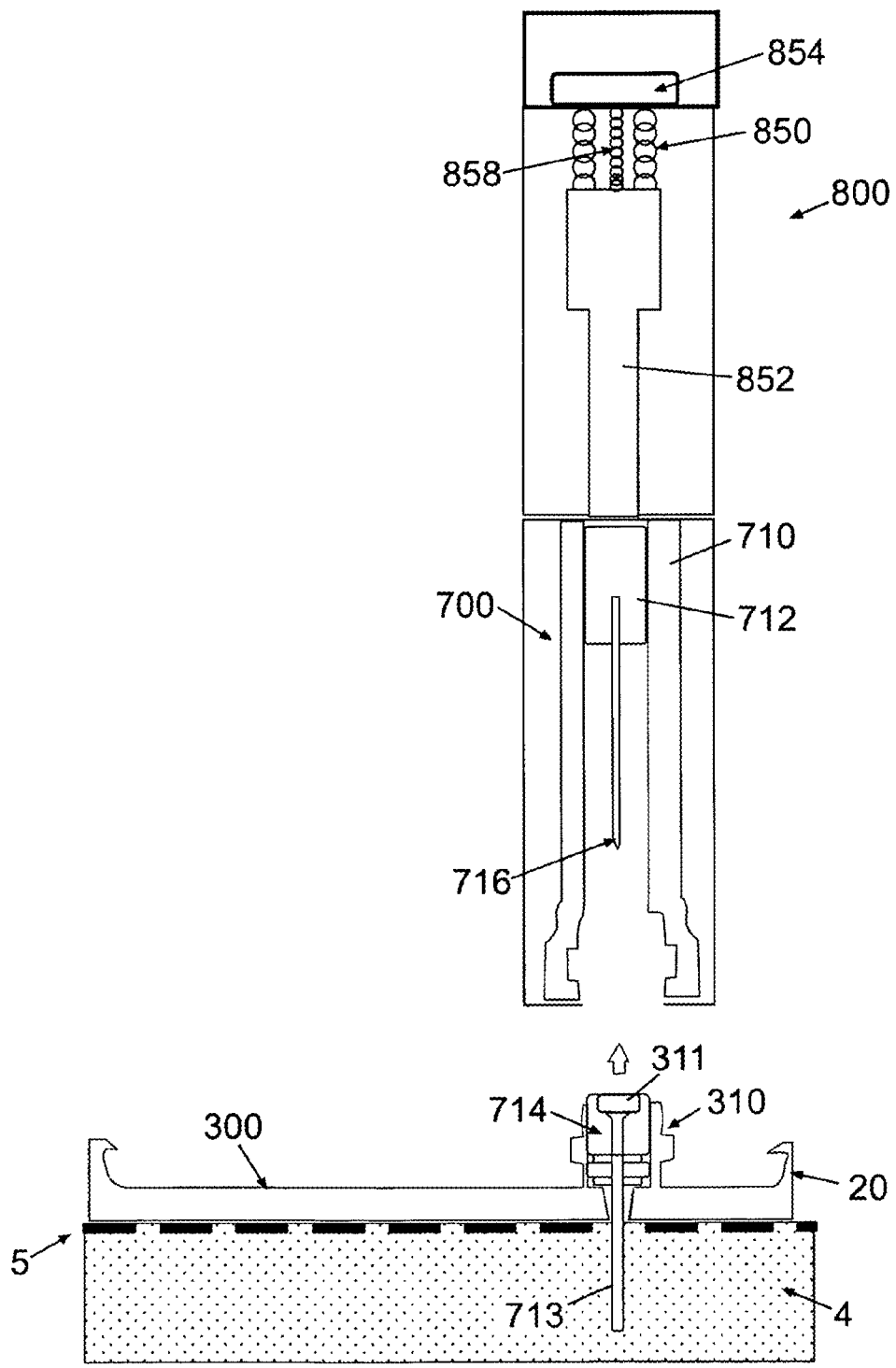

FIGS. 12a-c are cross-sectional views of the inserter loaded with the cannula cartridge unit (700) during an automatic insertion process. The connection of the inserter (800) to the cradle unit (20) and the insertion of the cannula (713) and penetrating member (716) into the subcutaneous tissue (4) are performed similarly to the connection discussed above with regard to FIGS. 11a-c. However, in this embodiment, the inserter (800) is provided with means for automatically retracting the penetrating member (716). In some embodiments, the inserter (800) includes a retraction spring (858) that can stretch during cannula insertion process, as shown in FIG. 12a. The retraction spring (858) can be configured to automatically compress once the penetrating member (716) and the cannula (713) are inserted into the subcutaneous compartment (4) and the cannula hub (714) is secured at the well (310). In some embodiments, the retraction spring (858) can compress upon pressing of the release button (854) or of a separate dedicated button (not shown in FIG. 12a). FIG. 12b shows the penetrating member (716) being retracted into the protector (710) by the retraction spring (858), while the cannula hub (714) remains connected to the well (310), and the cannula (713) remains in the subcutaneous tissue (4). FIG. 12c shows the disconnection of the inserter (800) from the cradle unit (20). The protector (710), now containing only the penetrating member (716), is then unloaded from the inserter (800) and disposed of. After disconnecting of the inserter (800) from the cradle unit (20), the dispensing patch unit can be connected to the cradle unit, as it has been previously discussed with regard to FIGS. 10h-i.

Figure 13A:
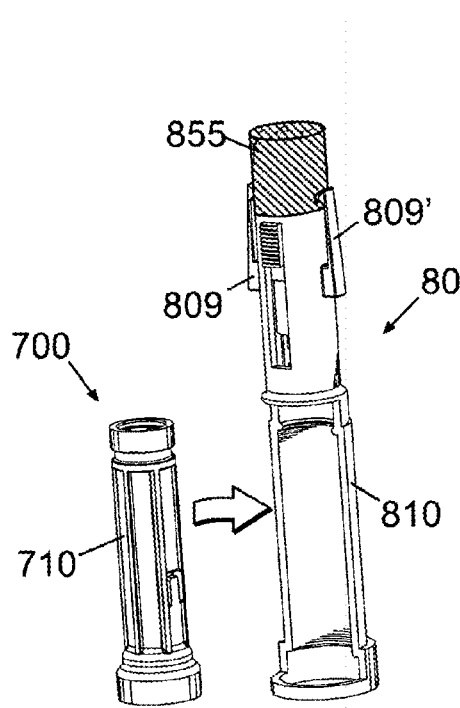
FIGS. 13a-c show an exemplary pen-like inserter and loading of the cannula cartridge unit into the pen-like inserter, according to some embodiments of the present invention.

FIG. 13a shows an example of a pen-like inserter (80) designed to contain within it a cannula cartridge unit (700). The inserter (80) is provided with a main body portion to accommodate placement of the cannula cartridge unit (700). The main body portion can be provided with an arcuate cross section to allow loading of the cannula cartridge unit (700) from the side. The main body portion can otherwise be configured, for example, as a tube to allow loading of the cannula cartridge unit (700) through the bottom opening of the inserter. In some embodiments, the inserter (80) includes means for preventing inadvertent or premature firing of the cannula. Such means could be, for example, a safety cap (855) which prevents contact between the two lateral triggers (809), (809') and the displacement mechanism (not shown in FIG. 13a) within the inserter (80). The safety cap (855) is removable from the inserter (80) upon connection thereof to the cradle unit (20) and prior to the insertion initiation. The body portion (810) includes a bottom open end (849) to allow insertion of the body portion (810) over the well (310), and a semi-annular protrusion (812) disposed on the inwardly facing wall and near the top end of the body portion (810). The inserter (80) further includes a displacement mechanism coupled to the body portion (810) for inserting the penetrating member and the cannula into the subcutaneous compartment (4), as will be discussed below.

Figure 13B:
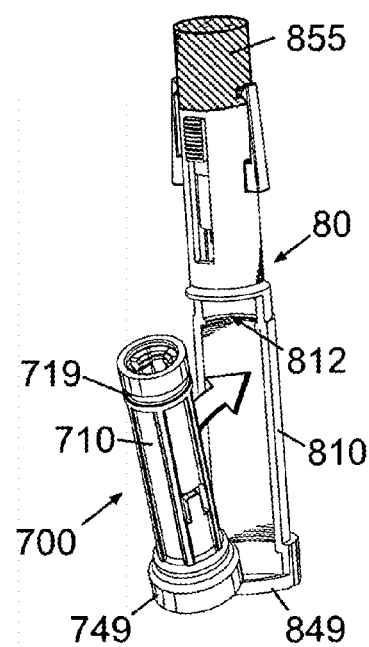

FIG. 13b shows how the cannula cartridge unit (700) is loaded into the pen-like inserter (80). As stated above, the unit (700) includes the protector (710) having the opened bottom end (749). The bottom end (749) of the protector (710) is placed inside the bottom part of the inserter having a corresponding ring-shaped section (849). The body of the protector (710) is then pushed into the inserter (80) until a semi-annular protrusion (812) protruding from the interior of the inserter (80) engages with a corresponding annular depression (719) disposed on the exterior of the protector (710). The protector (710) interlocks with the body portion (810), thereby securing the cannula cartridge unit (700) within the inserter (800).

Figure 13C:
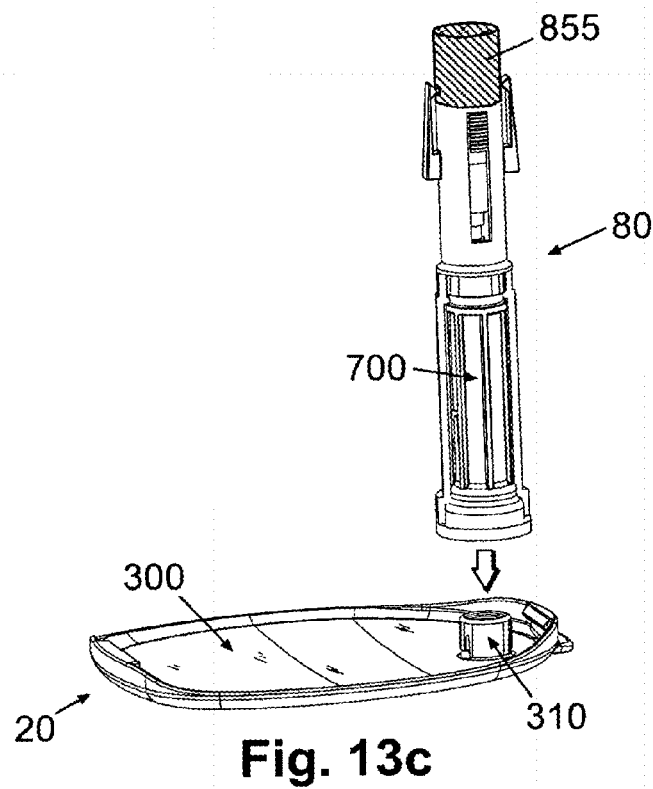

FIG. 13c shows the inserter (80) after it has been loaded with the cannula cartridge unit (700), and before its connection to cradle unit (20). In some embodiments, the inserter (80) includes means for preventing inadvertent or premature firing of the cannula.

Figure 14A:
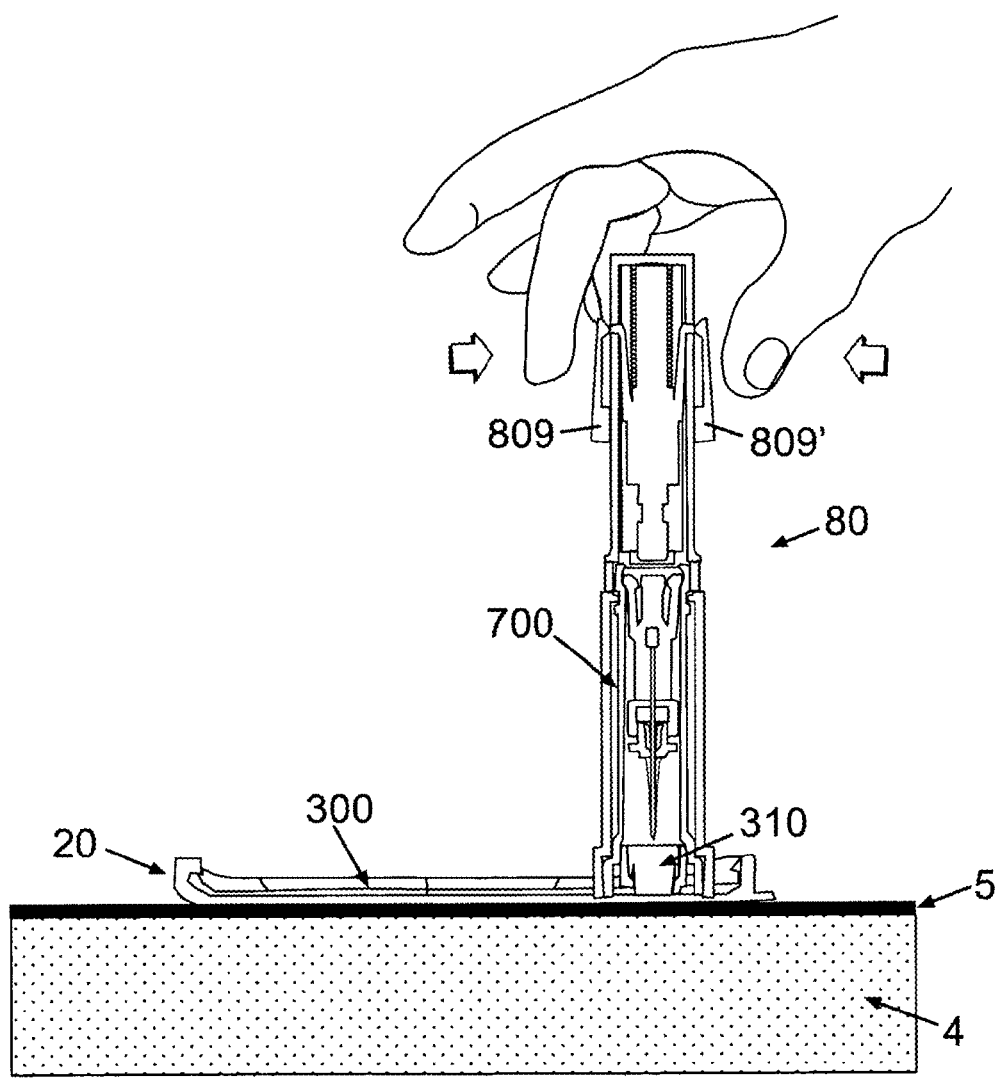
FIGS. 14a-f are cross-sectional views of the pen-like inserter during a cannula insertion process, according to some embodiments of the present invention.

FIGS. 14a-f are cross-sectional views of the inserter (80) loaded with a cannula cartridge unit (700) during cannula insertion process carried out with the pen-like inserter (80) shown in FIGS. 13a-c. FIG. 14a shows the inserter (80) after it has been loaded with the cannula cartridge unit (700) and connected to the cradle unit (20) (i.e., placed over the well (310) of the cradle unit (20), as discussed above with regard to FIG. 10c). After removing the safety cap from the inserter (80), the user initiates the cannula insertion process by pressing simultaneously two lateral triggers (809), (809') disposed on the exterior of the inserter (80), as shown in FIG. 14a. In some embodiments, the triggers (809) and (809') are used consecutively to insert the cannula. In some embodiments, there can be a single trigger (809) or more than two triggers (809).

Figure 14B:
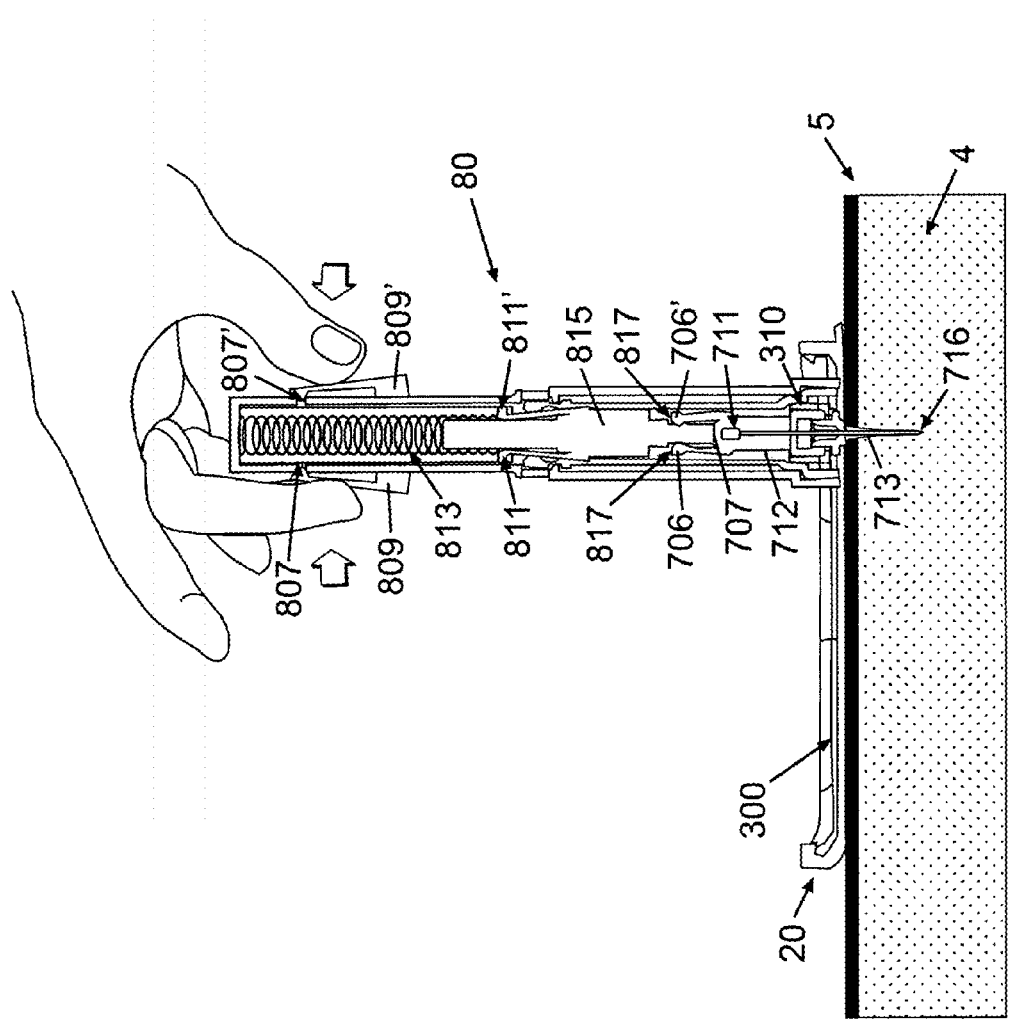

In addition to triggers (809), (809'), the inserter (80) includes a spring (813) disposed inside the inserter (80), rod (815) having an annular depression (817) and being coupled to the spring (813), and spring latches (811), (811') suspended on respective recesses (807), (807') (which are disposed near the top portion of the inserter (80)), as shown in FIG. 14b. FIG. 14b shows automatic insertion of the cannula (713) into the subcutaneous tissue (4). Upon pressing (whether simultaneously or not) the lateral triggers (809), (809'), the spring latch protrusions (811), (811') are pushed inwardly, thus, releasing them from their respective recesses (807), (807'). The spring (813), which is initially in a compressed loaded state, is released and stretches in a downward direction (or direction toward the skin (5)). The spring (813) pushes on the dedicated rod (815) and forces it to move in a downward direction (or direction toward the skin (5)). When the rod (815) reaches the bottom (707) of the crown-like section of the grip portion (712), the spring holding arms that constitute a crown-like section (only two arms (706), (706') are shown in FIG. 14b), are captured by the annular depression (817) provided in the rod (815). As a result, the penetrating cartridge (711) is forced to move in a downward direction toward the well (310). The penetrating member (716) and cannula (713) pass through the well (310) and are inserted into the subcutaneous compartment (4).

Figure 14D:
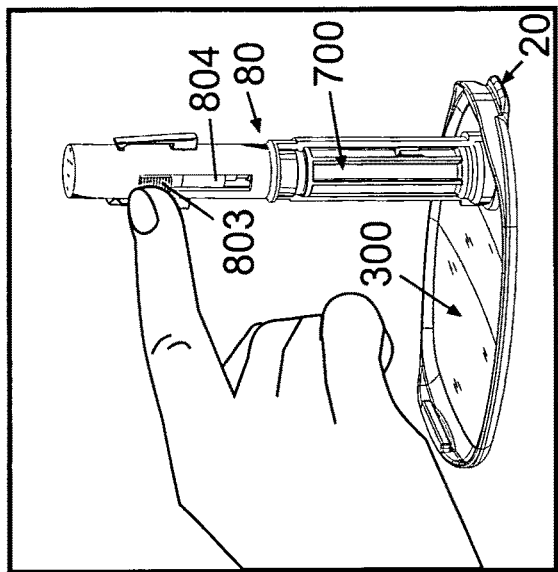
Figure 14C:
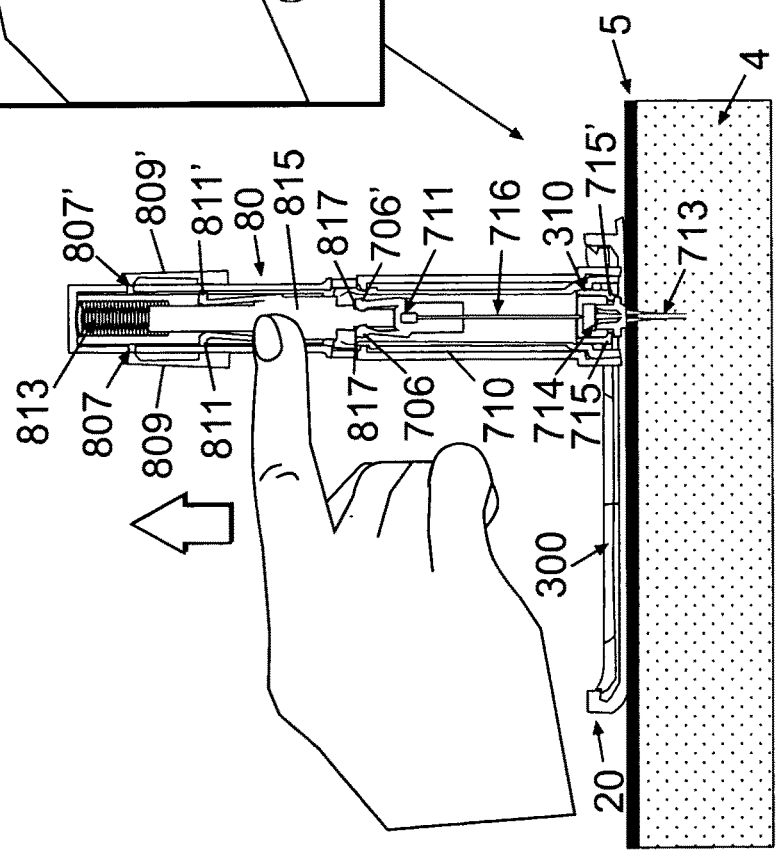

FIG. 14c shows how the penetrating member (716) is retracted. In some embodiments, the retraction is carried out manually by the user. After the cannula (713) has been inserted into the subcutaneous tissue (4), the user pushes a lever (803) in an upward direction, where the lever is connected to the rod (815) and is accessible to the user through a window (804) in the inserter's main body portion, as can be seen in FIG. 14d. This causes the rod (815) with the penetrating member (716) to retract, and the spring (813) to compress into its pre-firing state. When the spring holding arms (706) reach the top section of the protector (710) having a larger diameter than the body of the protector (710), the arms (706) are released from the annular depression (817) provided in the rod (815) and assume their original position within the protector (710).

The retraction process ends when the spring (813) is returned to its loaded state, and the spring latch protrusions (811), (811') become suspended in their respective recesses (807), (807'). As the penetrating member (716) is retracted, the cannula hub (714) remains within the well (310). In some embodiments, the well (310) includes spring protrusions (715), (715') to help retain the cannula hub (714) within the well (310).

As can be understood by one skilled in the art, the retraction of the penetrating member (716) can otherwise be carried out automatically, e.g., by employing a second retraction spring.

Figure 14E:
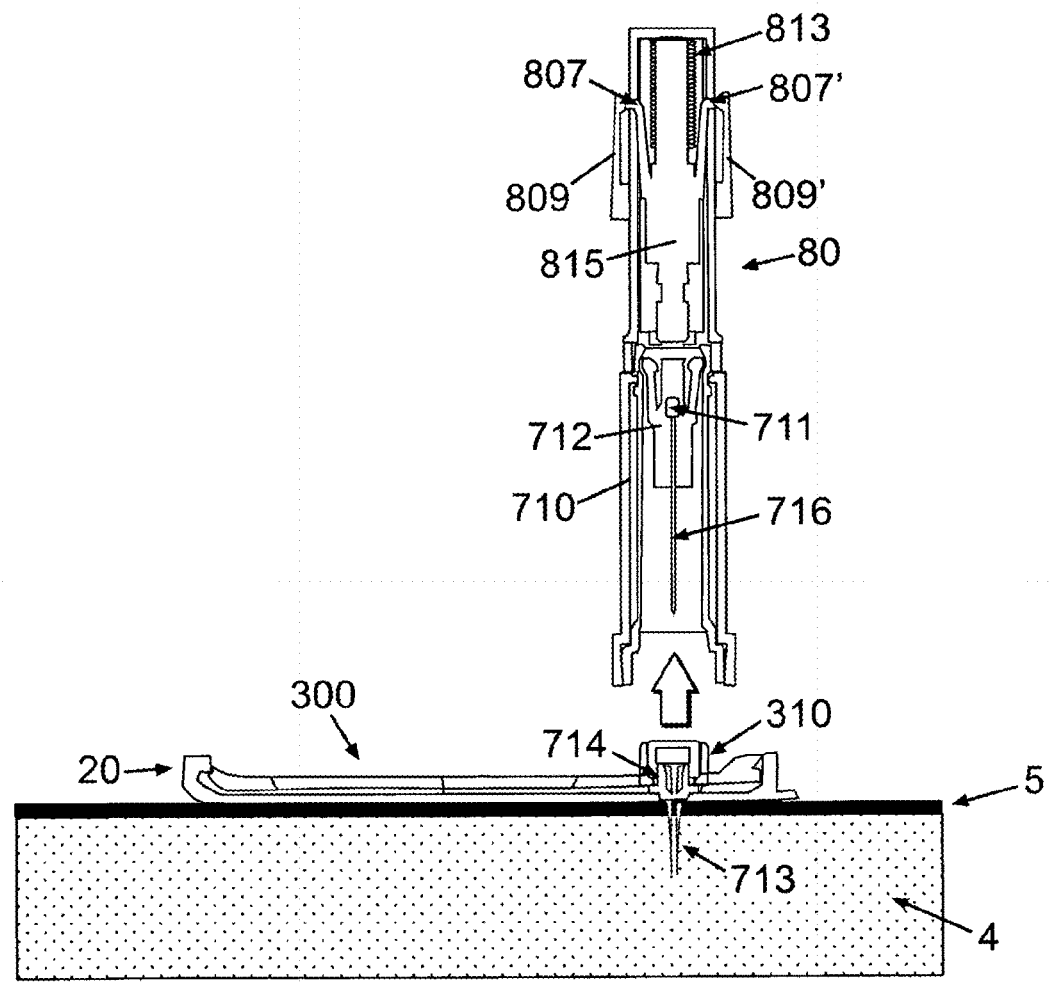

FIG. 14e shows the disconnection of the inserter (80) from the cradle unit (20) after the manual retraction process has been completed. At this stage, the spring (813) returns to its initial loaded state, and the rod (815) is disconnected from the grip portion (712). After disconnecting the inserter (80) from the cradle unit (20), the user can connect a dispensing patch unit to the cradle unit (20).

Figure 14F:
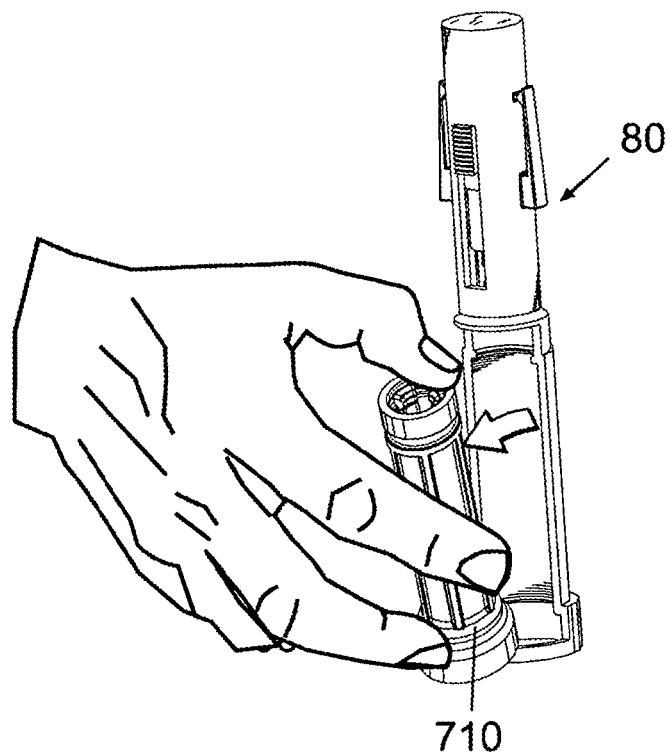

The protector (710) can then be unloaded from the inserter (80), as illustrated in FIG. 14f. After unloading is completed, the protector (710) containing the penetrating member inside can be disposed.

Figure 15A:
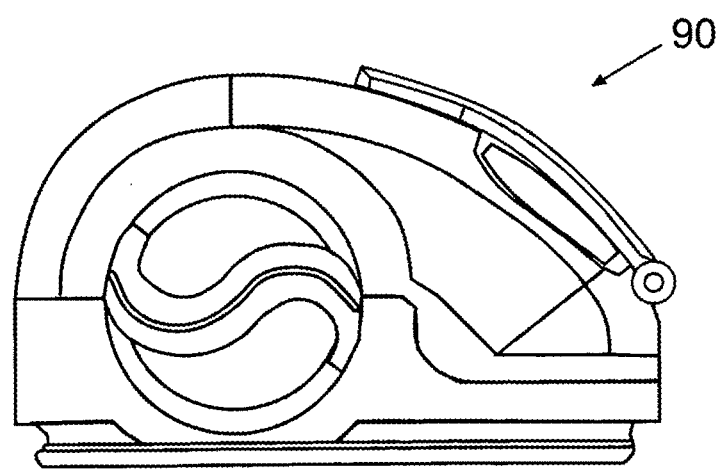
FIGS. 15a-b are side and perspective views of an exemplary mouse-like inserter, according to some embodiments of the present invention.
Figure 15B:
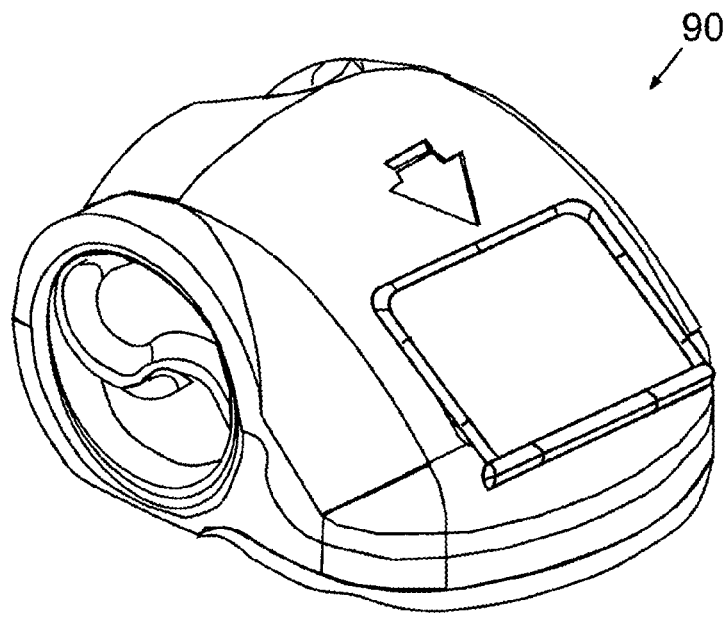

FIGS. 15a-b are side and perspective views of another exemplary inserter (90), according to some embodiments of the present invention. FIGS. 15a-b show a mouse-like inserter (90) pre-loaded with the cradle unit (not shown) and the cannula cartridge unit (not shown). The inserter (90) can be used for both facilitating adherence of the cradle unit to the patient's body and for convenient insertion of the cannula into the subcutaneous tissue. The inserter (90) can include a release button that allows the user to insert the penetrating member and the cannula (not shown in FIGS. 15a-b) into the subcutaneous compartment. The inserter (90) can also include a compartment for insertion of the cannula cartridge unit (700), as will be discussed below. As can be understood by one skilled in the art, the inserter (90) can have any desired shape and is not limited to the inserter (90) shown in FIGS. 15a-b. The inserter (90) shown in these figures is provided for exemplary, non-limiting purposes.

Figure 15C:
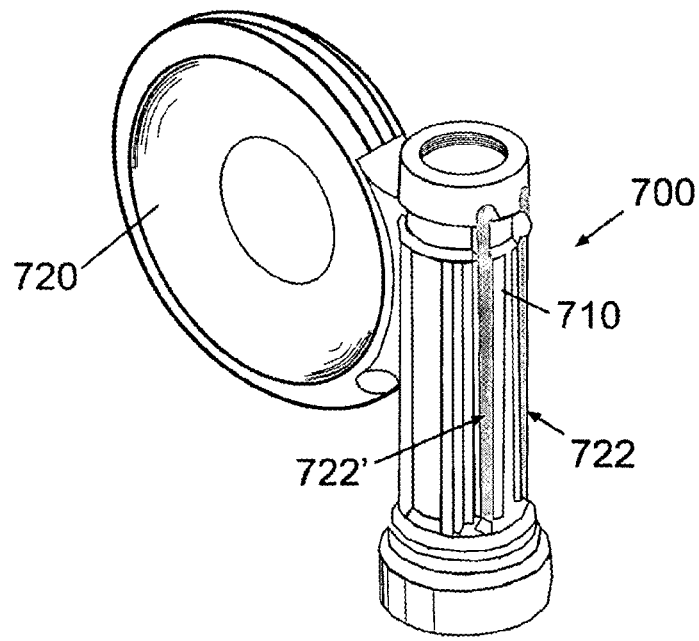
FIG. 15c shows an exemplary cannula cartridge unit provided with a handle, according to some embodiments of the present invention.

In the above embodiment, the cannula cartridge unit (700) can include a handle (720), as illustrated in FIG. 15c, to enable more convenient gripping of the cannula cartridge unit (700) and proper placement of the cannula cartridge unit (700) within the inserter (90). The handle (720) is not limited to any specific shape or size. Additionally, the protector (710) includes at least one slit (722), (722') disposed opposite to the handle (720). The slits (722), (722') allow pushing of the penetrating cartridge down towards the body of the patient.

Figure 16:
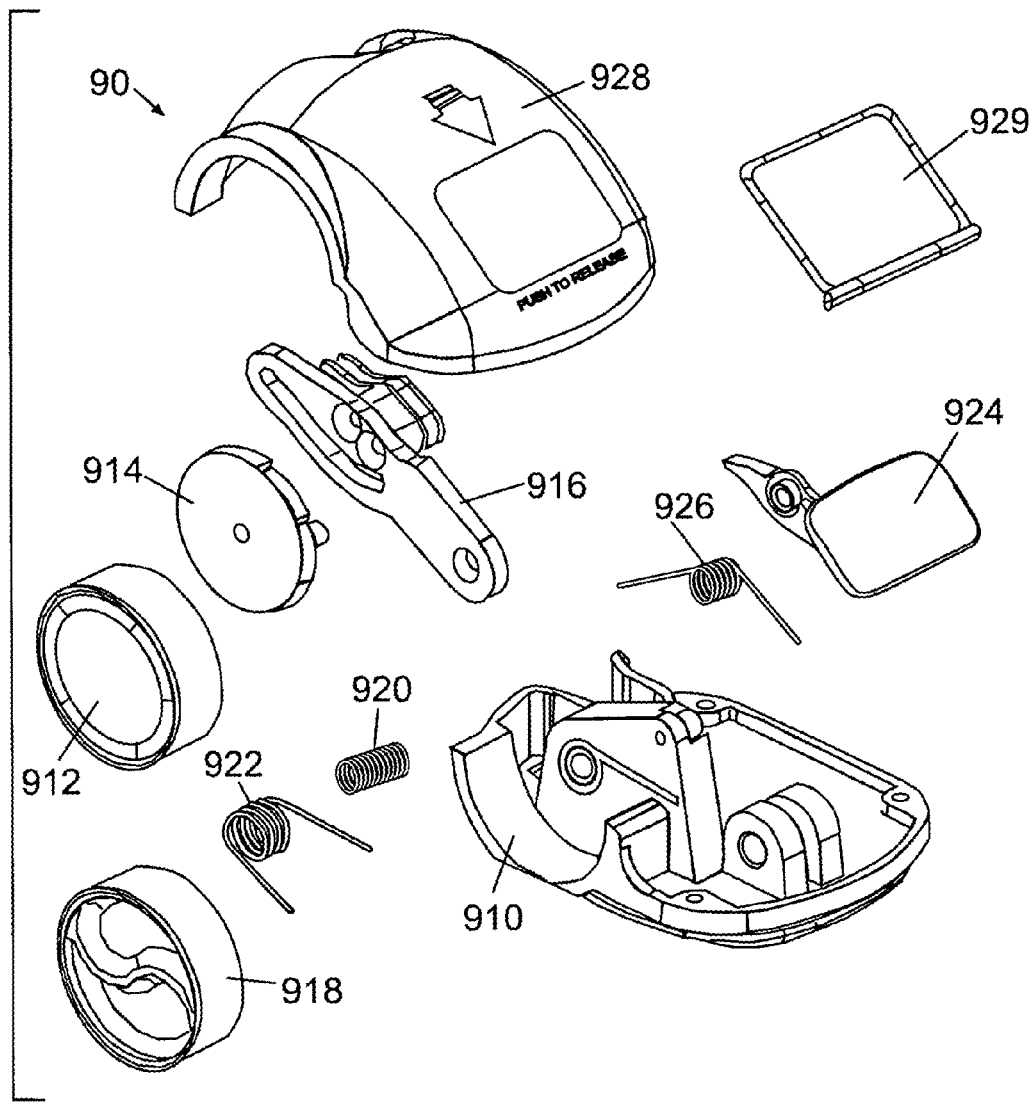
FIG. 16 is an exploded view of the mouse-like inserter, according to some embodiments of the present invention.

FIG. 16 is an exploded view of the mouse-like inserter (90), according to some embodiments of the present invention. The inserter (90) includes an inserter base (910), a ratchet flywheel (912), a ratchet crank (914), an insertion lever (916), a loading button (918), a loading spring (920), a flywheel torsion spring (922), a release button (924), a release torsion spring (926), and a housing (928) to secure the above components, and a safety cap (929). Functions of these components will be explained below in more detail.

Figure 17A:
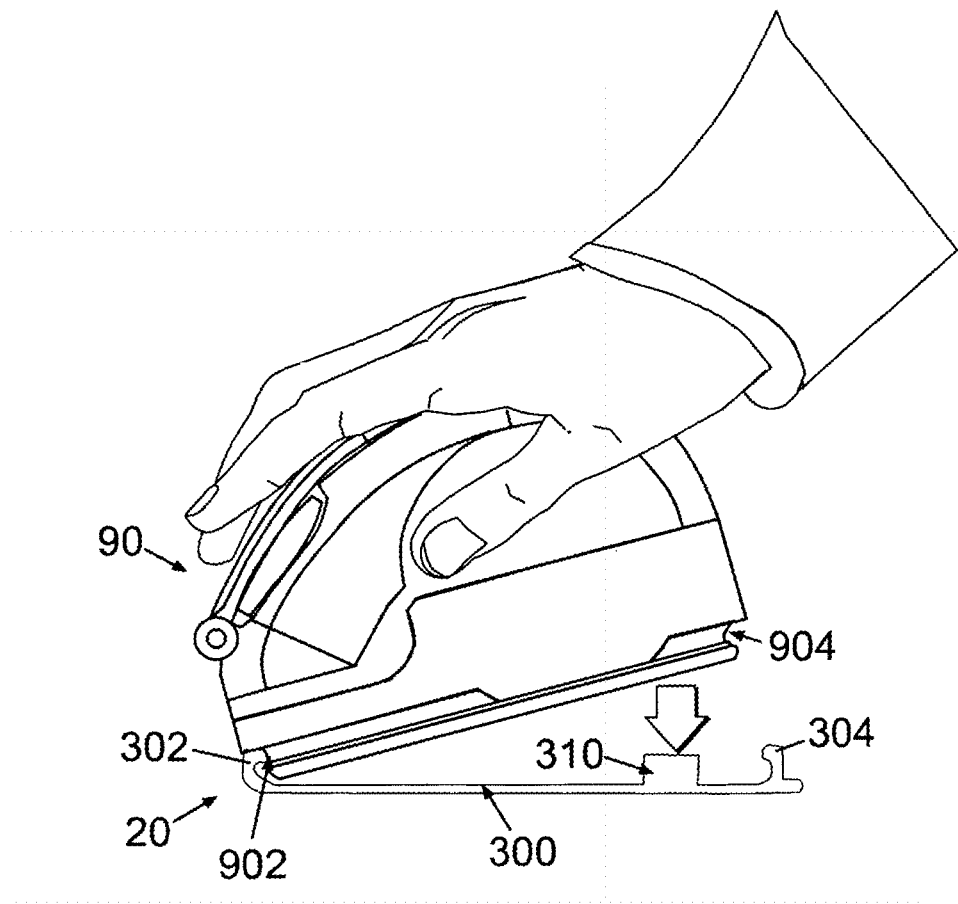
FIGS. 17a-b shows an exemplary connection of the mouse-like inserter to the cradle unit, according to some embodiments of the present invention.
Figure 17B:
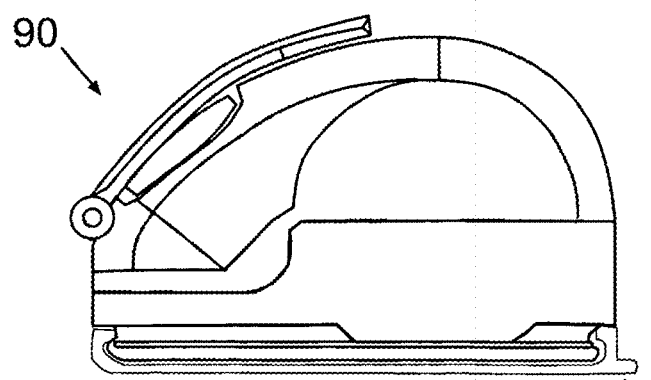

FIGS. 17a-b show connection of the inserter (90) to the cradle unit (20), according to some embodiments of the present invention. FIG. 17a shows engagement of a dedicated recess (902) provided in the inserter (90) with a corresponding protrusion (302) provided in the front end of the cradle base (300). The rear end of the inserter (90) is then pushed down towards the cradle unit (20) and the two units become connected due to a snapping engagement of a latch (304) provided in the rear of the cradle base (300) with a corresponding notch (904) provided in the inserter (90). FIG. 17b shows the inserter (90) being connected to the cradle unit (20).

Figure 18:
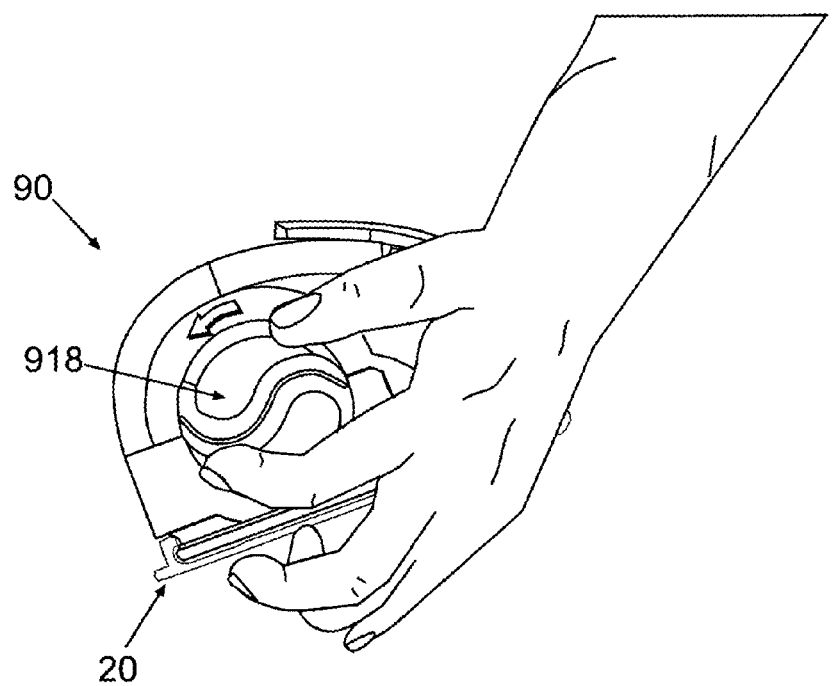
FIG. 18 shows an exemplary loading of the flywheel torsion spring of the mouse-like inserter, according to some embodiments of the present invention.

The inserter (90) includes a displacement mechanism that uses a spring-loaded flywheel. Thus, prior to loading the cannula cartridge unit (not shown) into the inserter (90), the user loads the flywheel torsion spring (922), as illustrated in FIG. 18. To load the flywheel torsion spring, the user first inwardly pushes the loading button (918) (provided on the exterior of the inserter (90)), and thus, couples the loading button (918) with the ratchet flywheel (not shown in FIG. 18), and then turns the loading button (918) (as shown in FIG. 18, in a counterclockwise direction, however in some embodiments loading of the loading button can be carried by turning it in a clockwise direction). This rotational movement tensions, and thus, loads the flywheel torsion spring (922).

Figure 19A:
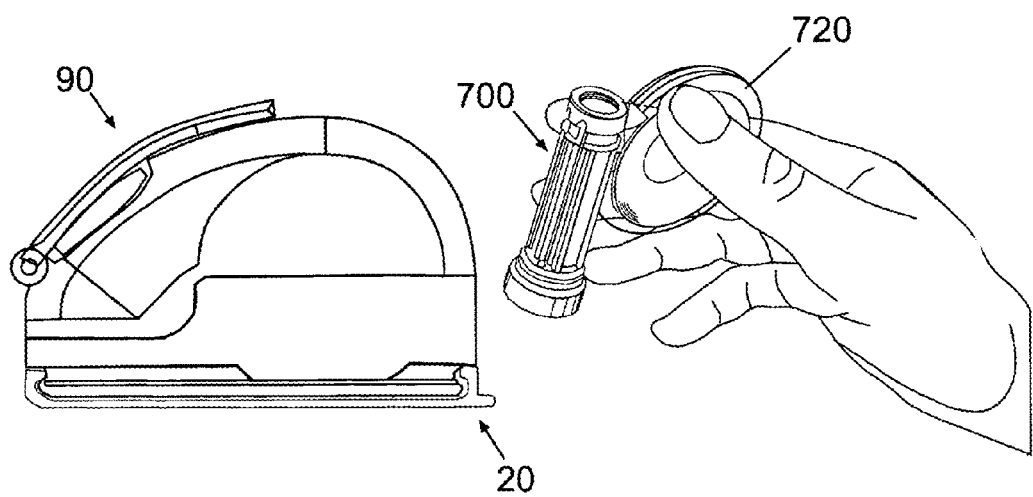
FIGS. 19a-d show an exemplary loading of the cannula cartridge unit into the mouse-like inserter, according to some embodiments of the present invention.
Figure 19B:
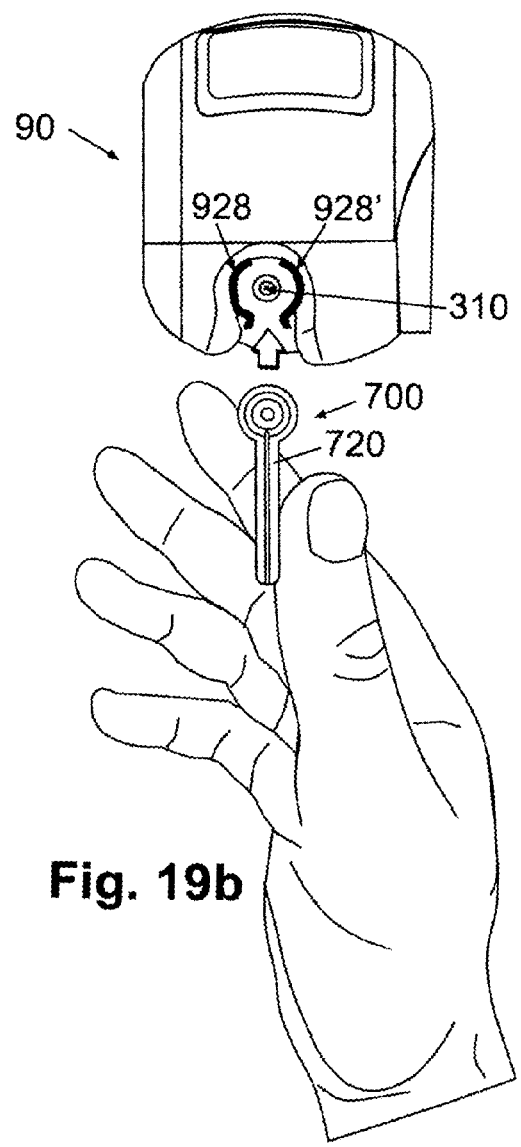
Figure 19C:
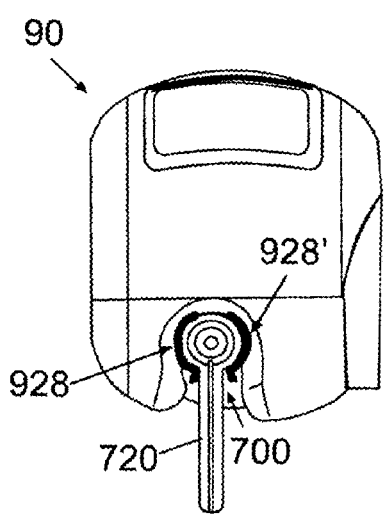

FIGS. 19a-b show loading of the cannula cartridge unit (700) into the inserter (90). In some embodiments, loading of the cannula cartridge unit (700) into the inserter (90) takes place after connecting the inserter (90) to the cradle unit (20) and after loading the flywheel torsion spring (922). In some embodiments, the cannula cartridge unit (700) includes the handle (720), as discussed above with regard to FIG. 15c. To accommodate insertion, in some embodiments the inserter includes at least one spring holder (928), (928') disposed around the opening created in the inserter (90) for receiving the cannula cartridge unit. To insert the unit (700) into the inserter (90), the user grips the cannula cartridge unit (700) by its handle (720), places it over the well (310), and then pushes the unit (700) into the inserter (90) until it is captured by the spring holders (928), (928'), as shown in FIG. 19c. This ensures that the cannula cartridge unit (700) is properly positioned as required for the cannula insertion process. As can be understood by one skilled in the art, other ways of securing the unit (700) to the inserter (90) are possible.

Figure 19D:
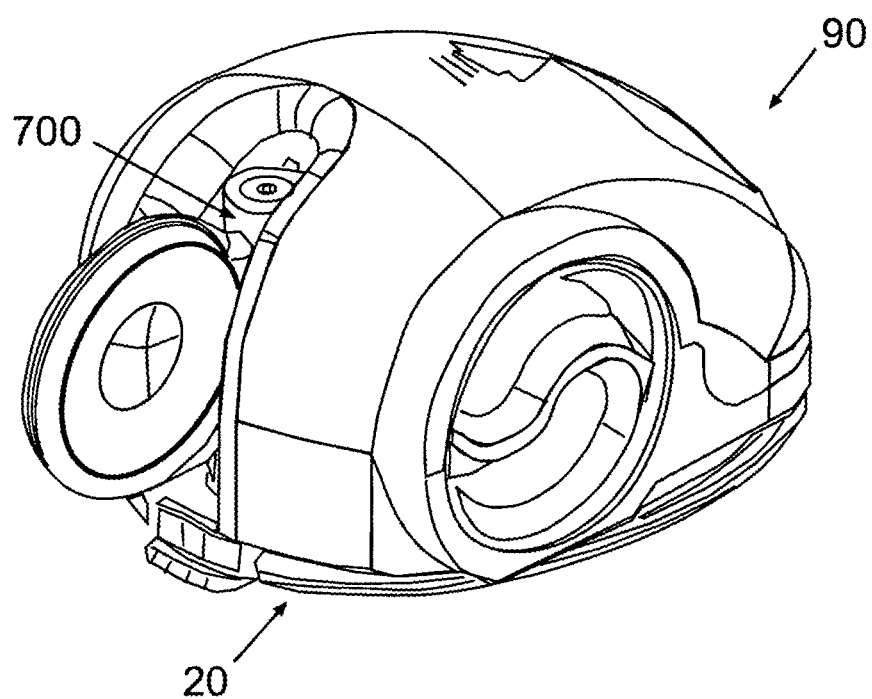

FIG. 19d is a perspective view of the inserter (90) after it has been connected to the cradle unit (20) and loaded with the cannula cartridge unit (700). As illustrated in FIG. 19d, the inserter is connected to the cradle unit (20) using the latch-recess connection shown in FIGS. 17a-b. The unit (700) is loaded into the opening created in the inserter (90) with the handle (720) protruding away from the unit (700).

Figure 20A:
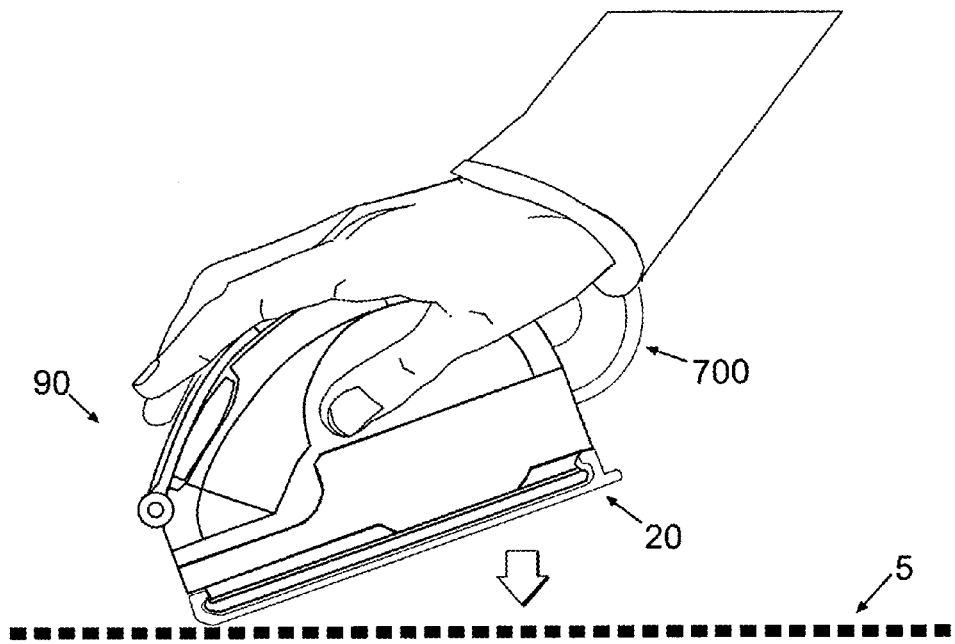
FIGS. 20a-b show the cradle unit being adhered to the user's skin, according to some embodiments of the present invention.
Figure 20B:
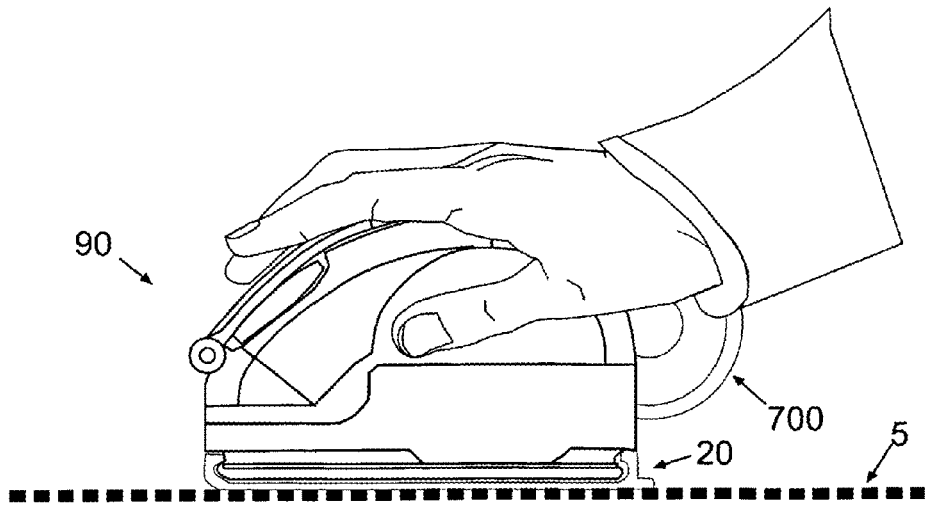

FIGS. 20a-b shows how the cradle unit (20) is adhered to the user's skin (5). The inserter (90) can be ergonomically configured to allow easy and comfortable holding. The user can attach the cradle unit (20) to the skin (5) by a single movement down, or gradually by first placing the front (or rear) end of the cradle unit (20) on the skin (5) and then pressing the cradle unit (20) to the skin (5).

Figure 21A:
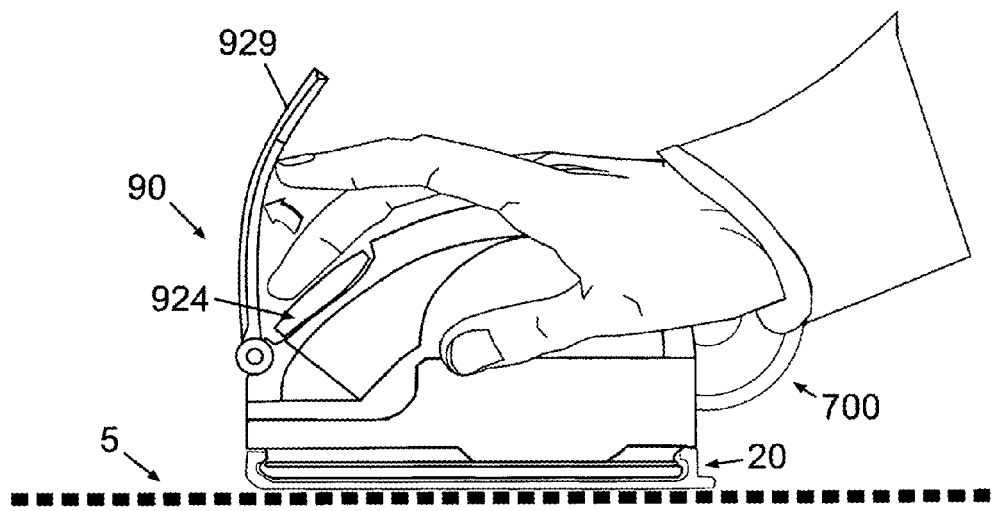
FIGS. 21a-i show an exemplary cannula insertion process using the mouse-like inserter, according to some embodiments of the present invention.

FIG. 21a-i show an exemplary cannula insertion process using the mouse-like inserter (90), according to some embodiments of the present invention. FIG. 21a shows the inserter (90) ready for operation after being adhered to the skin (5). The user then lifts a safety cap (929), which can detachably cover the release button (924) to prevent inadvertent and premature firing of the cannula.

Figure 21B:
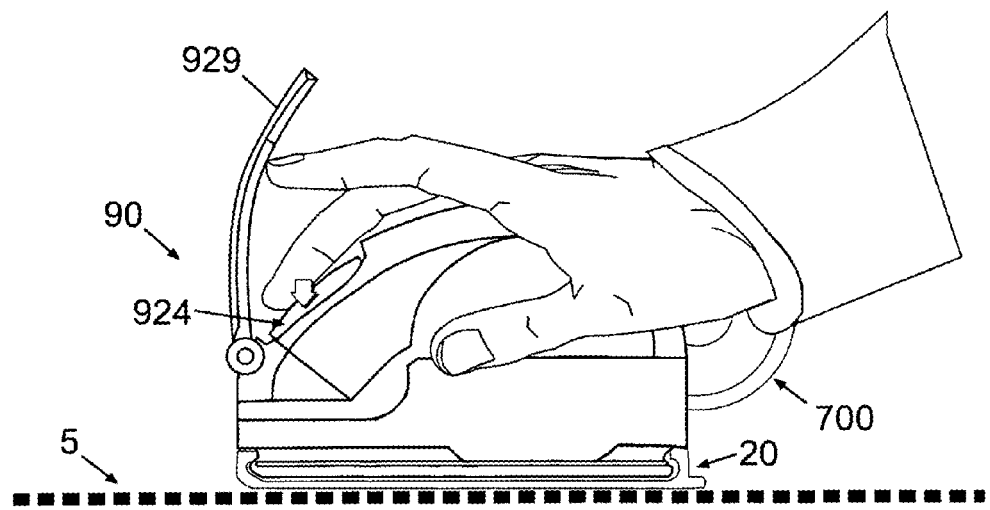
Figure 21C:
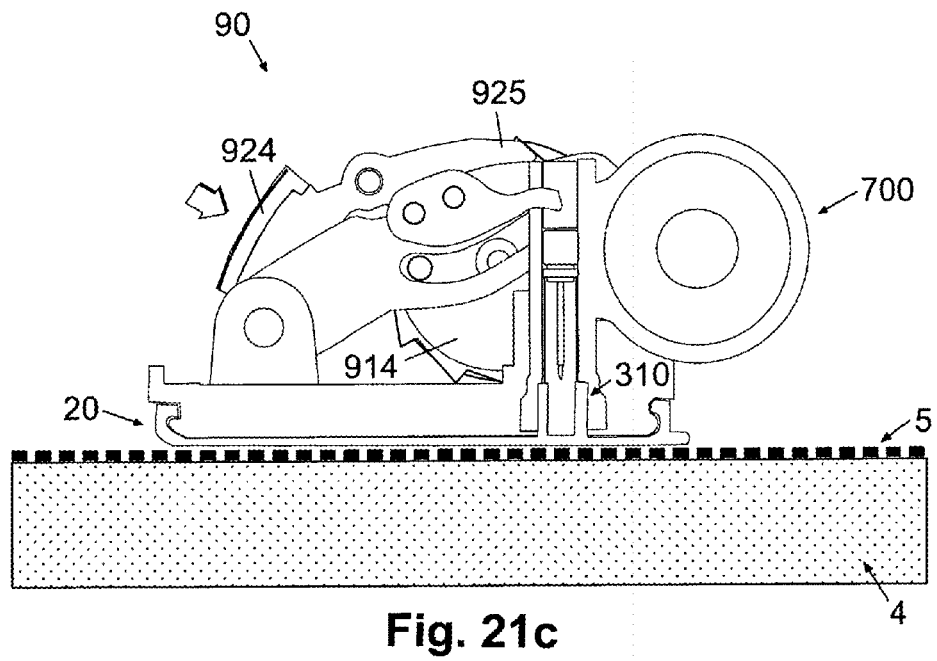
Figure 21D:
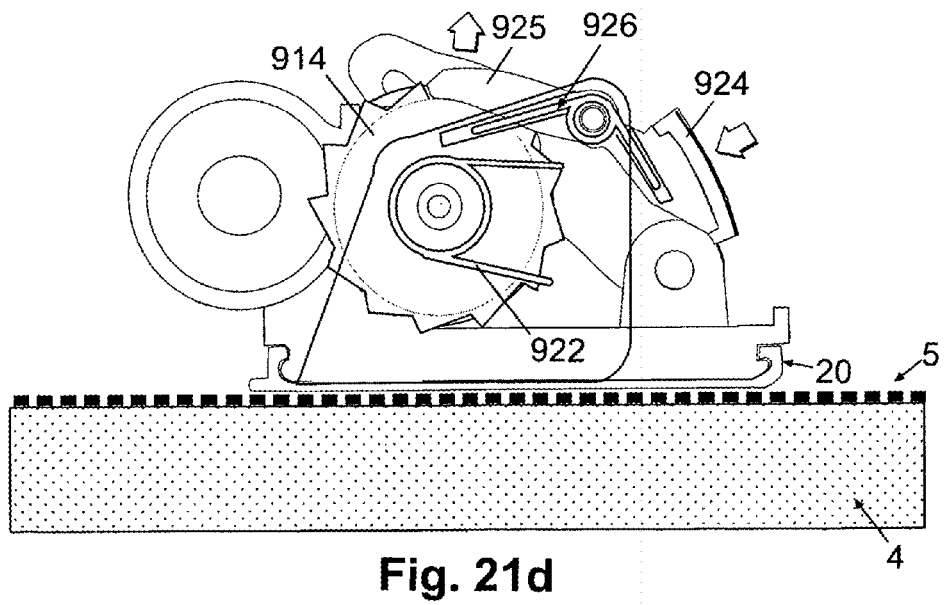
Figure 21E:
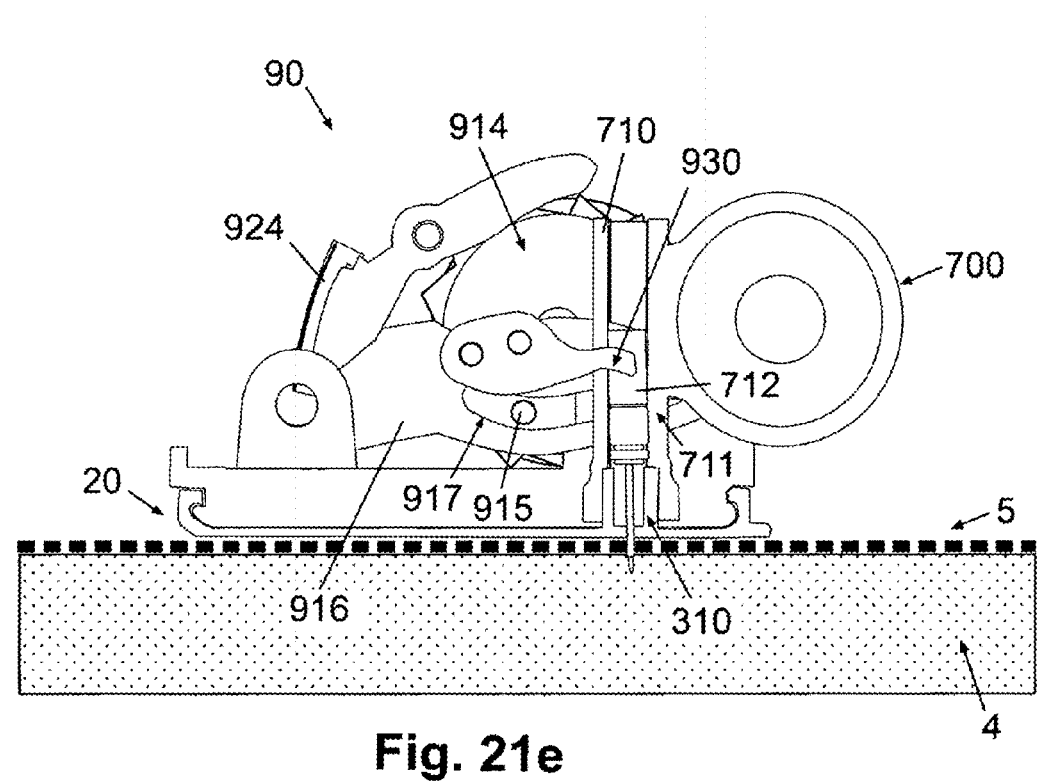

FIGS. 21b-d are side and cross-sectional views, respectively, of the initiation of the cannula insertion process initiated by pressing of the release button (924) (as shown in FIG. 21b, the user presses the button (924) in a downward direction, as indicated by an arrow). Pressing of the release button (924) causes the restraining arm (925) of the release button (924) to lift off the ratchet crank (914), as illustrated in FIGS. 21c-d. Thus, the crank (914) rotates via application of the force of the loaded flywheel torsion spring (922), which is partially embedded in the associated ratchet flywheel (not shown in FIGS. 21c-d). As the crank (914) rotates, its rotation is converted into linear vertical motion of the insertion lever (916) by means of a crank protrusion (915). The crank protrusion (915) moves along a dedicated slot (917) provided in the lever (916), as shown in FIG. 21e. As the insertion lever (916) moves downwards, the penetrating cartridge (711) is shot in a downward direction toward the well (310). The cartridge (711) motion is accomplished using the engagement hooks (930) of the insertion lever (916). The hooks (930) maintain contact with the grip portion (712) of the penetrating cartridge (711) through slits (722) provided in the protector (710) (the slits are not shown in FIG. 21e).

Figure 21F:
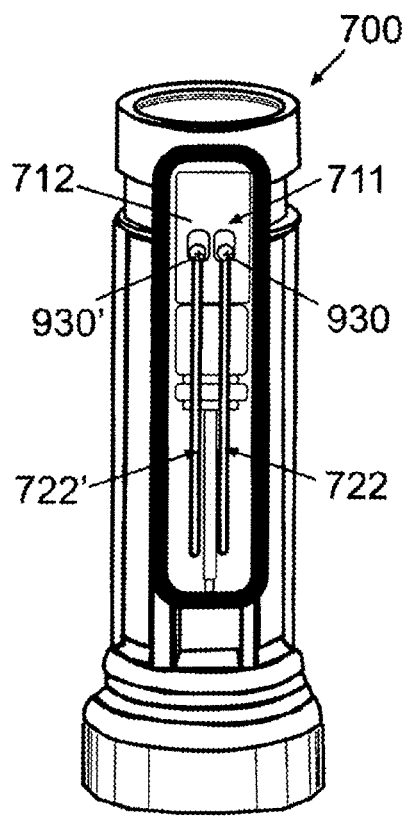
Figure 21G:
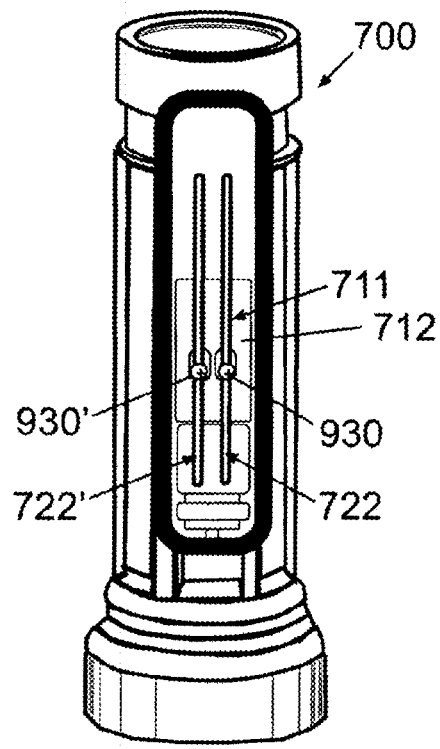

FIGS. 21f-g schematically show downward thrusting of the penetrating cartridge (711) using the hooks (930), (930') penetrating through the slits (722), (722'). FIG. 21f illustrates hooks (930) disposed at the top of the penetrating cartridge (711) in a pre-firing state. As the displacement mechanism is actuated, the hooks (930) move in a downward direction along respective slits (722), as shown in FIG. 21g, thus protracting the penetrating cartridge (711) towards the well (310).

Figure 21H:
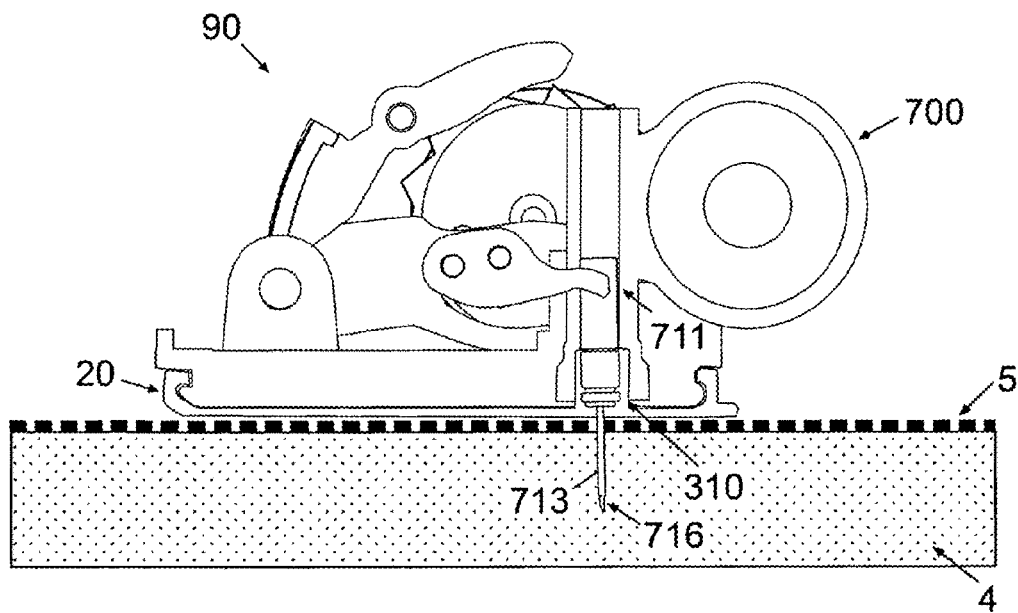

FIG. 21h shows another stage of the cannula (713) insertion process, according to some embodiments of the present invention. As shown in FIG. 21h, the penetrating cartridge (711) is disposed within the well (310) and the cannula (713) and penetrating member (716) pass through the well (310) to be inserted into the subcutaneous tissue (4).

Figure 21I:
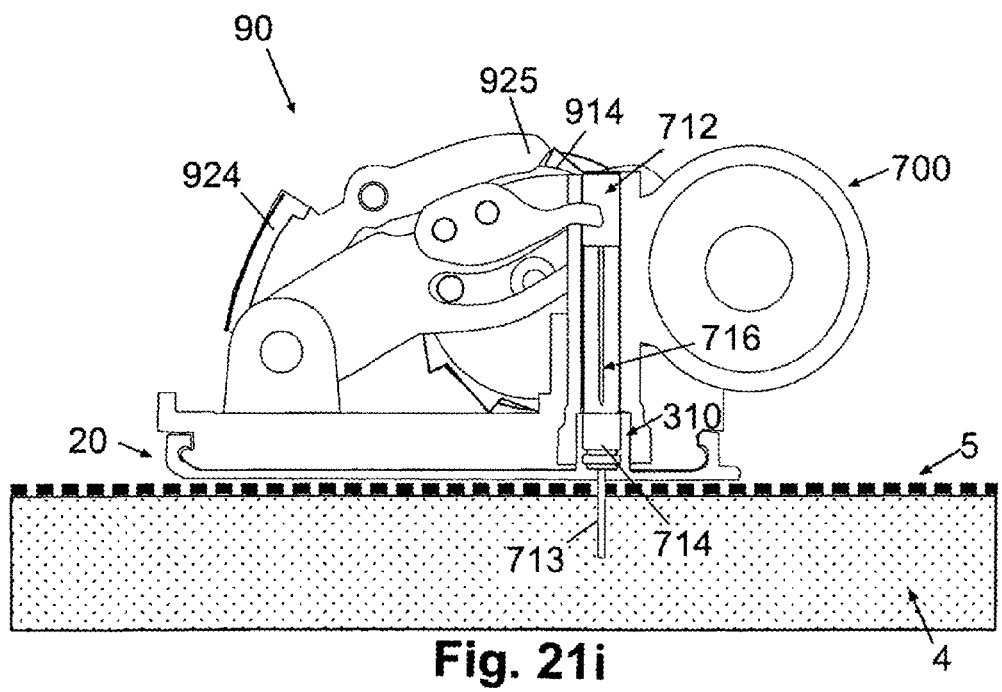

FIG. 21*i* shows automatic retraction of the penetrating member (716) as the crank (914) completes its rotation, according to some embodiments of the present invention. As the crank (914) rotates, the grip portion (712) that holds the penetrating member (716) is pushed in an upward direction and away from the skin (5), thereby removing the member (716) from the subcutaneous compartment (4). As stated above, as the member (716) is removed, the cannula (713) remains disposed in the compartment (4). Further, as the penetrating member (716) is retracted, the cannula hub (714) is also retained within the well (310).

Figure 22:
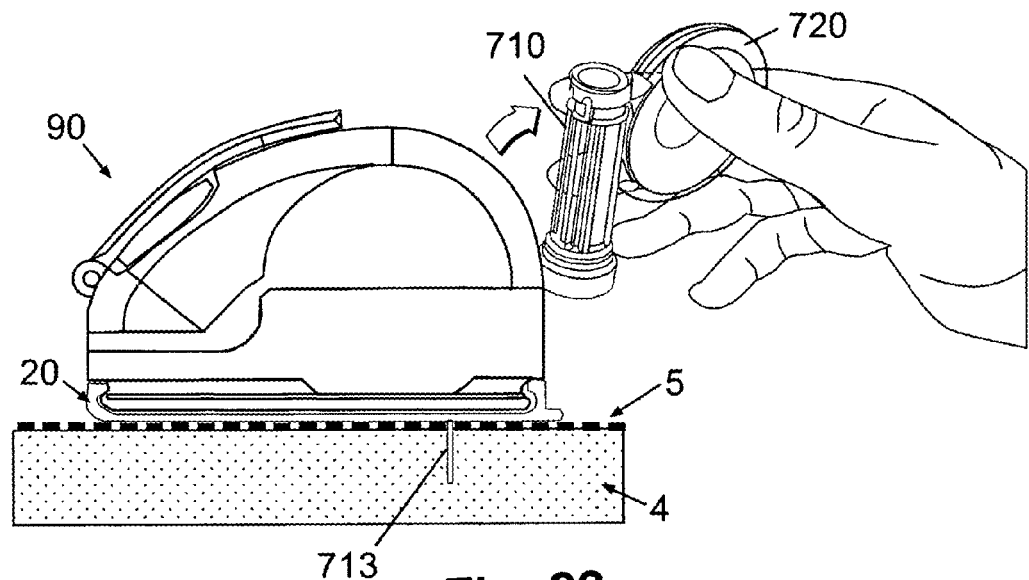
FIG. 22 shows an exemplary unloading of a protector from the mouse-like inserter, according to some embodiments of the present invention.

FIG. 22 shows how the protector (710) (containing the penetrating member) can be unloaded from the inserter (90) by gripping the protector's (710) handle (720) and pulling the protector (710) out of the inserter (90). The protector (710) (containing the penetrating member) can then be disposed. As can be understood by one skilled in the art, the unloading of the protector (710) can be performed either before or after the inserter (90) is disconnected from the cradle unit (20).

Figure 23:
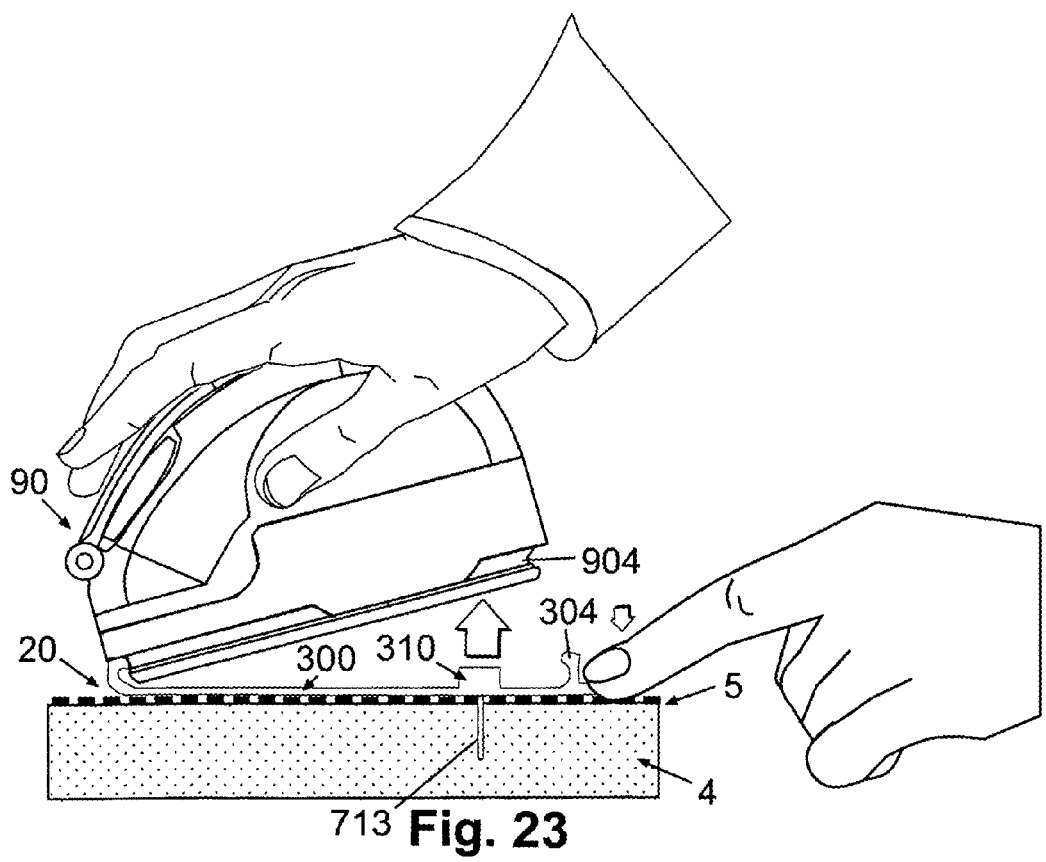
FIG. 23 shows an exemplary disconnection of the mouse-like inserter from the cradle unit, according to some embodiments of the present invention.

FIG. 23 shows disconnection of the inserter (90) from the cradle unit (20). Disconnection can be accomplished by manually releasing the latch (304) and detaching the inserter (90). Alternatively, the inserter (90) can include a mechanism that releases the latch (304) from the corresponding notch (904), either automatically after the penetrating member has been retracted back into the protector, or upon manual actuation by the user/patient. After disconnecting the inserter (90) from the cradle unit (20), the user can connect a dispensing patch unit (not shown) to the cradle unit (20).

Figure 24A:
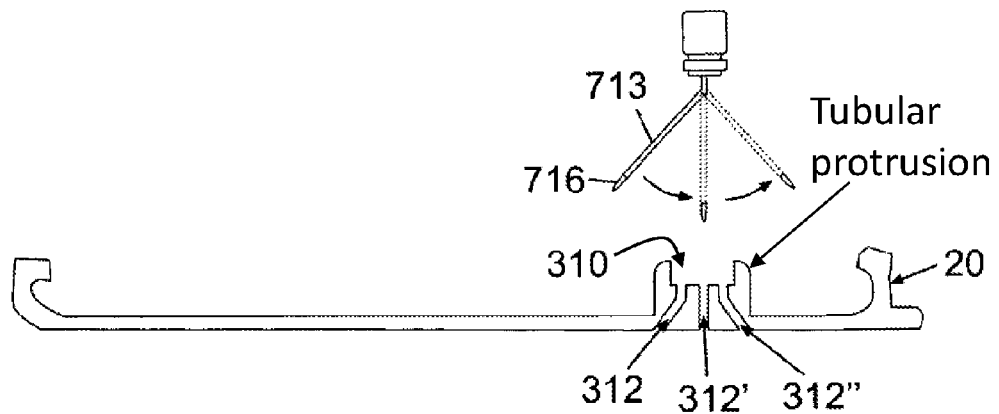
FIGS. 24a-b show an exemplary mouse-like inserter which allows the user to choose the desired cannula penetration angle, according to some embodiments of the present invention.
Figure 24B:
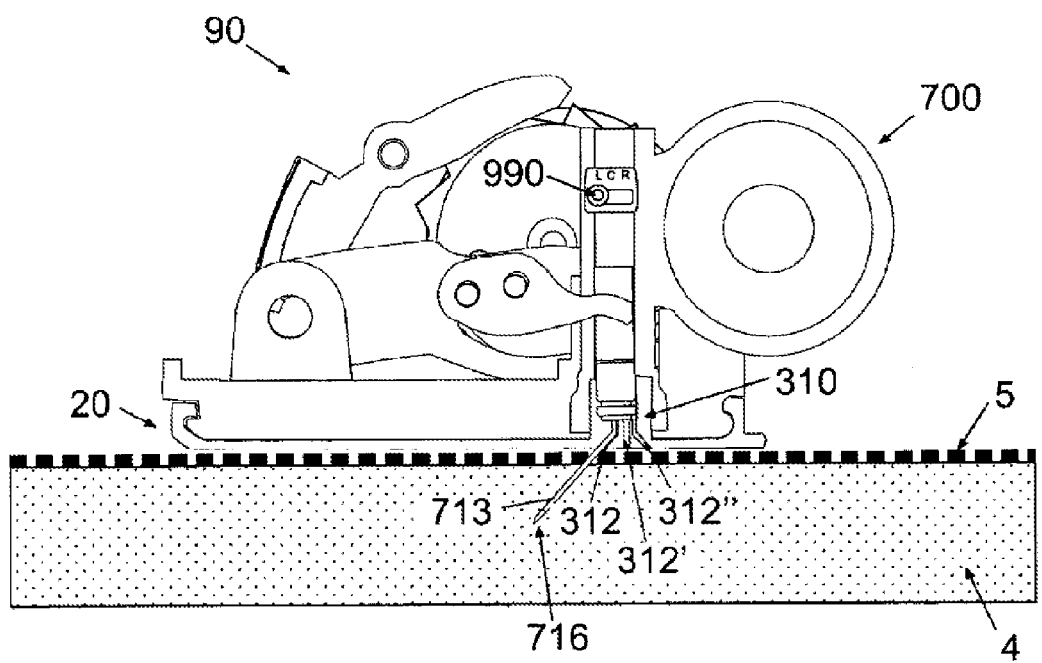

FIGS. 24*a*-*b* show an embodiment of the mouse-like inserter (90) which allows the user to choose the desired cannula (713) penetration angle. In some embodiments, a flexible cannula (713) and a flexible penetrating member (716) are used. The cradle unit (20) can include a tubular protrusion emerging upwardly therefrom and defines therein a well (310), which includes a plurality, e.g., three penetration tunnels (312), (312'), (312"), to allow insertion of the cannula (713) at various angles, as shown in FIG. 24*a*.

FIG. 24*b* is a cross-sectional view of the inserter (90) provided with a button (990) allowing the user to choose the desired penetration angle. The button (990) is located on the exterior of the inserter (90). In FIG. 24*b*, the button (990) is illustrated as being deployed within the interior of the inserter (90) for illustration purposes. As can be understood by one skilled in the art, the button can be disposed anywhere on the inserter (90). Upon pressing of the button (990), the cannula and the penetrating member can be inserted in at a desired angle or position ("L"—left side, "C"—center, "R"—right side). In some embodiments, the angle of insertion can be varied by the user and the user can be allowed to select a specific angle of insertion.

Figure 25A:
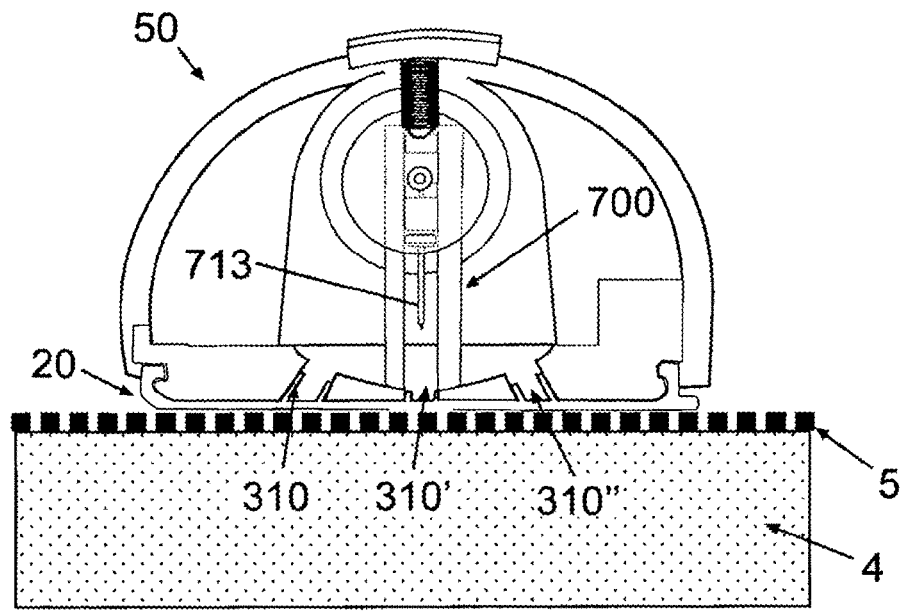
FIGS. 25a-g show another exemplary inserter which allows the user to choose the desired cannula penetration angle, according to some embodiments of the present invention.
Figure 25B:
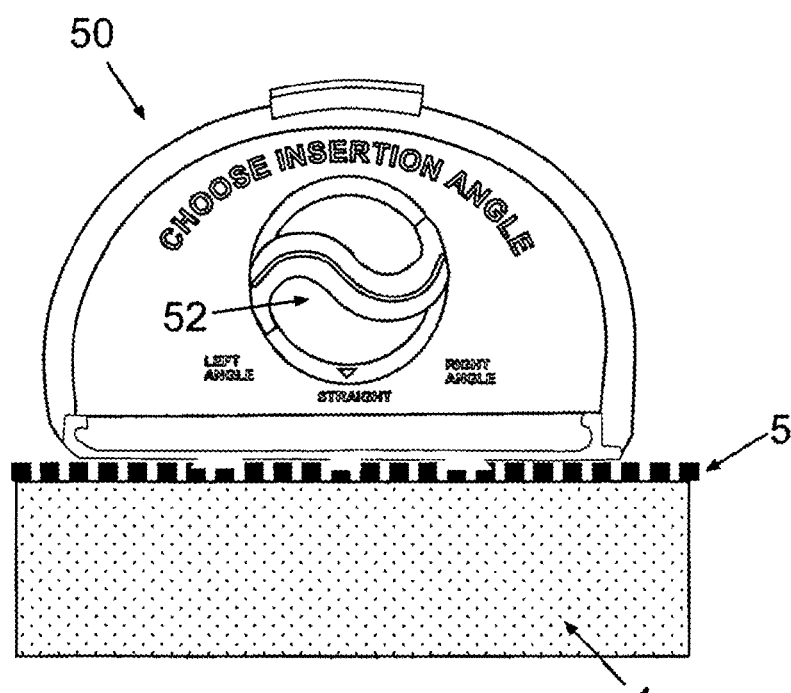
Figure 25C:
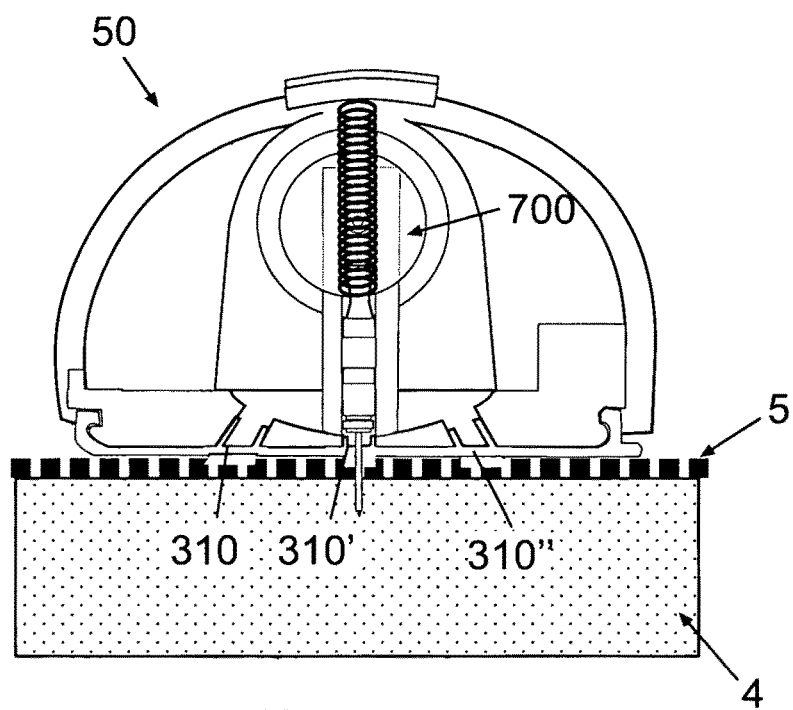
Figure 25D:
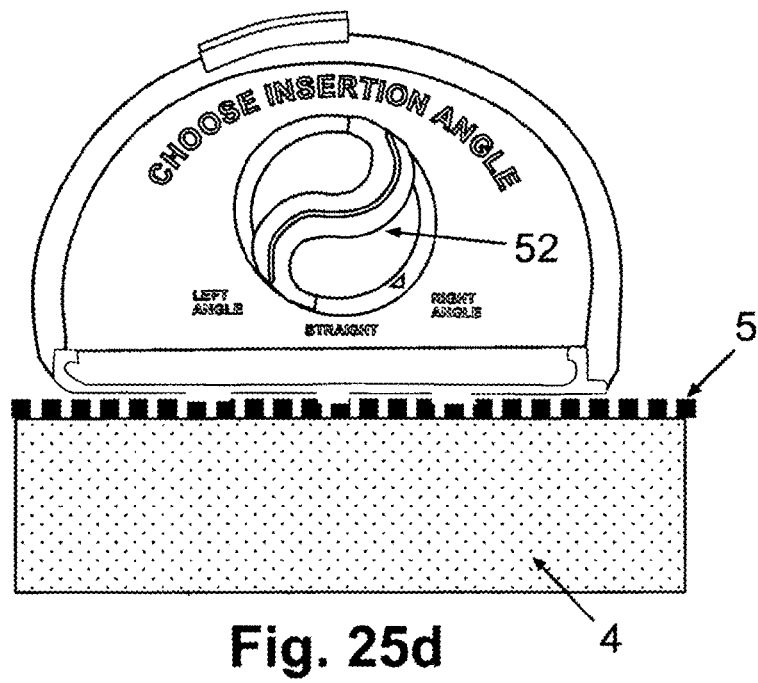
Figure 25E:
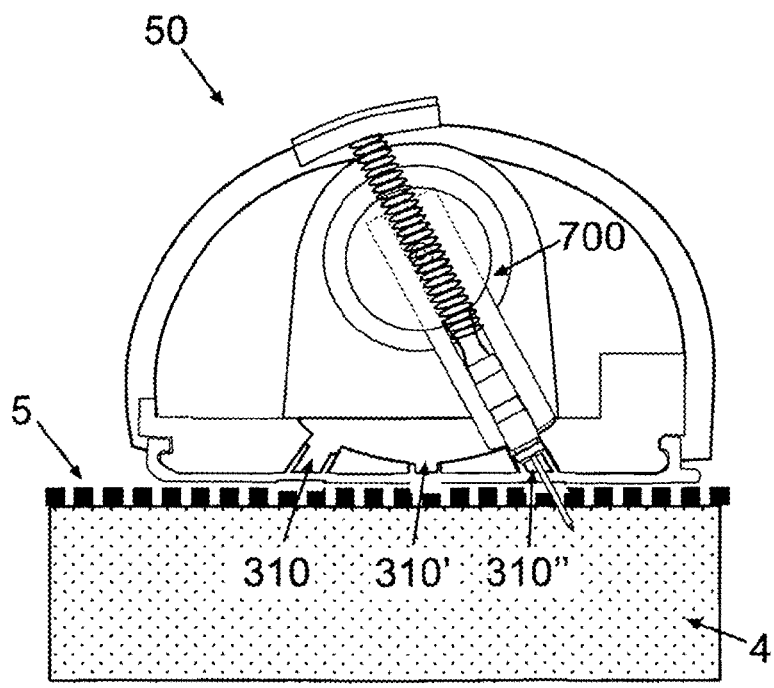
Figure 25F:
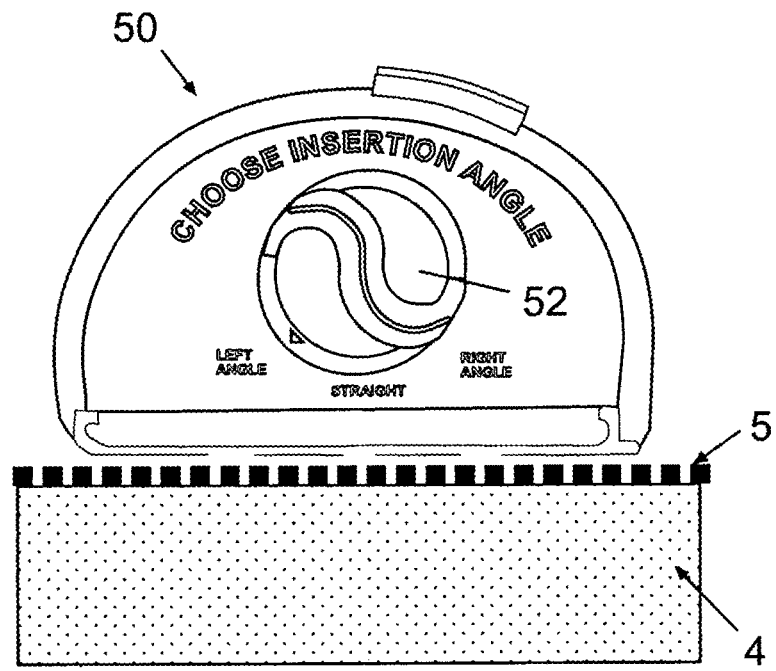
Figure 25G:
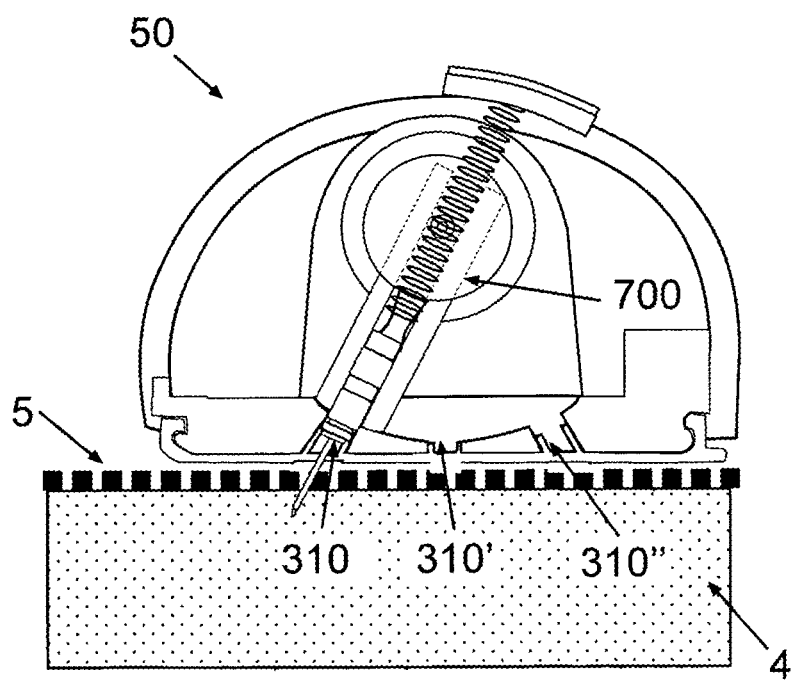

FIGS. 25*a*-*g* show another exemplary inserter (50) that allows the user to choose the desired cannula (713) penetration angle. FIG. 25*a* shows a cross-sectional view of the inserter (50) attached to the cradle unit (20) adhered to the skin. The inserter (50) is preloaded with the cannula cartridge unit (700). In some embodiments, the cradle is provided with three different wells (310), (310'), (310") which are slanted with respect to the cradle unit at different angles to allow various penetration angles. FIGS. 25*b*-*g* are side and cross-sectional views of how the user can choose the desired insertion angle by turning the button (52), which is connected to the cannula cartridge unit (700). Upon rotation of the button (52), the cannula cartridge unit (700) is rotated in a corresponding direction. For example, if a perpendicular insertion is desired (i.e., center), the button (52) is rotated to a center position, thus, rotating the unit (700) to be perpendicular to the skin (5), as shown in FIGS. 25*b*-*c*. Right angular insertion is illustrated in FIGS. 25*d*-*e* and left angular insertion is illustrated in FIGS. 25*f*-*g*. In some embodiments, the button (52) can be rotated to a specific angle of insertion, thus, causing insertion of the cannula at a desired angle. In some embodiments, the inserter (50) illustrated in FIGS. 25*a*-*g*, or a similar inserter, can be used for insertion of two cannulae coupled to one dispensing patch unit, where one cannula is used for fluid (e.g., insulin) delivery and the other for continuously monitoring a bodily analyte (e.g., glucose).

Figure 26A:
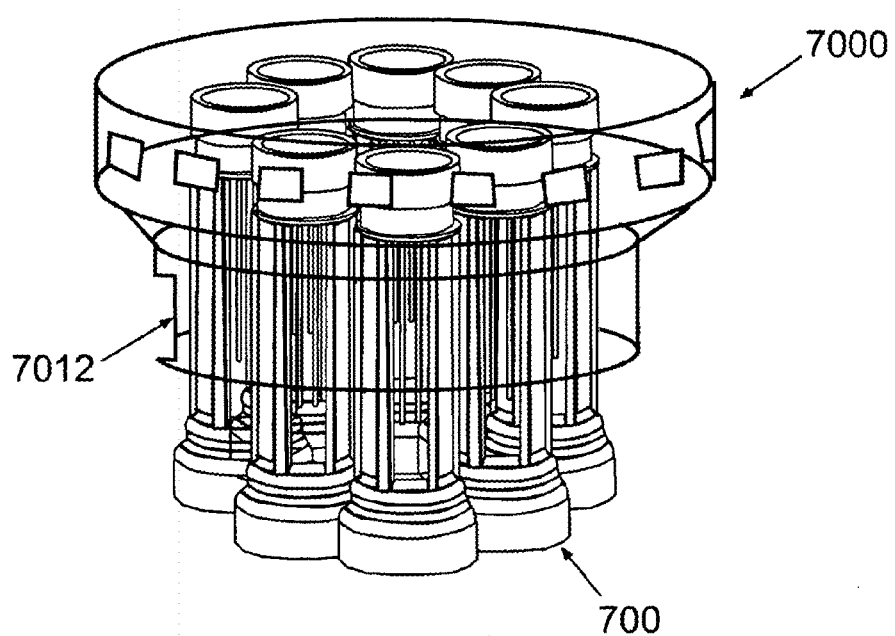
FIGS. 26a-b show exemplary drum of the cannula cartridge units and an exemplary inserter provided with a drum member for retaining plurality of cannula cartridge units, according to some embodiments of the present invention.
Figure 26B:
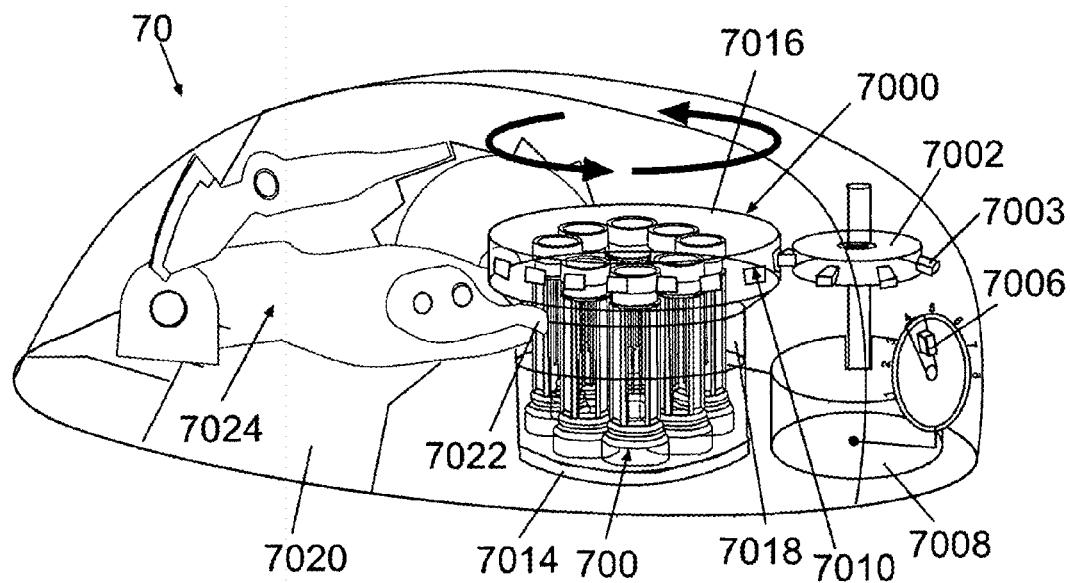

FIGS. 26*a*-*b* show another exemplary inserter (70) which is designed to contain a drum member (7000) for storing a plurality of the cannula cartridge units (700). FIG. 26*a* shows a drum member (7000) that is loaded with several cannula cartridge units (for example, eight cannula cartridge units (700)). The drum member has a dedicated slit (7012) through which hooks (not shown) of an insertion lever (not shown) are able to approach and penetrate the appropriately positioned cannula cartridge unit (700).

FIG. 26*b* shows an inserter (70) containing the drum member (7000). The drum member has a stationary part (7018) and a revolving part (7016). The stationary part (7018) is secured by a dedicated barrel (7014) protruding from the inserter's base (7020), while the revolving part (7016) is free to rotate upon user discretion. The user rotates the revolving part (7016) of the drum for firing an unused penetrating cartridge by turning a switch (7006) located in the exterior of the inserter (70) until it points to the number of the next cannula cartridge unit (700). The switch (7006) is connected to a rotating means (7008) located within the inserter (70), which rotates a wheel (7002) fitted with protrusions (7003). The protrusions (7003) then rotate the revolving part (7016) of the drum member (700), which accommodates the cannula cartridge units (700), by engaging with apertures (7010) located on the circumference of the revolving part (7016) of the drum member. Once the unused cannula cartridge unit (700) is brought into place, the hook/s (7022) of the insertion lever (7024) penetrate/s through the cannula cartridge unit's (700) longitudinal slit/s (not shown) and approach/es the cannula cartridge unit. Thus, the user can initiate the cannula insertion process, which in this embodiment is carried out similarly to what was described with reference to FIGS. 21*a*-*i*.

As can be understood by one skilled in the art, the displacement mechanism described above can be configured to allow automatic and/or manual displacement of the penetrating cartridge. In case of a manual displacement, a rod can be used to push the cartridge, as described above.

In some embodiments, the inserter discussed above with regard to FIGS. 1*a*-26*b* can accommodate insertion of a subcutaneously insertable element that can include a cannula, a probe, and/or a sensor. The subcutaneously insertable element can be used for fluid delivery and analyte sensing as well as other tasks.

Thus it is seen that devices, systems and methods are provided for inserting a cannula into the body of a patient. Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

All of the foregoing patents, applications, and publications referenced in this specification are hereby incorporated by reference herein in their entireties.

What is claimed is:

1. A subcutaneous insertion apparatus comprising:
   a housing configured to receive at least one cartridge unit, the at least one cartridge unit comprising a protective member containing therein at least one subcutaneously insertable element and at least one penetrating member, the housing including:
      a first housing opening adapted for at least loading therethrough the at least one cartridge unit into the housing; and
      a second housing opening adapted for at least protracting therethrough the at least one insertable element and the at least one penetrating member; and
   a displacement mechanism contained within the housing and configured to at least protract the at least one insertable element and the at least one penetrating member through the second housing opening toward the body of the patient for subcutaneous insertion of the at least one insertable element,
   wherein the displacement mechanism is configured to be primed for activation prior to the housing receiving the at least one cartridge unit; and
   the insertion apparatus is configured to couple to a skin-securable cradle that comprises a tubular protrusion emerging upwardly from the cradle that defines therein a well, the well comprising a plurality of penetration tunnels for directing the subcutaneous insertable element toward a plurality of angles with respect to a plane of a bottom housing opening, and the insertion apparatus is configured to align the subcutaneous insertable element with any of the plurality of penetration tunnels of the well, so as to insert the subcutaneous insertable element through the aligned tunnel.

2. The insertion apparatus according to claim 1, wherein the displacement mechanism is further configured to retract the penetrating member into the protective member subsequent to the subcutaneous insertion of the insertable element.

3. The insertion apparatus according to claim 1, wherein the displacement mechanism comprises a rod for manually forcing the at least one insertable element and the at least one penetrating member toward the body of the patient.

4. The insertion apparatus according to claim 1, wherein the displacement mechanism includes a loadable spring, wherein unloading of the spring results in protraction of the at least one insertable element and the at least one penetrating member toward the body of the patient.

5. The insertion apparatus according to claim 4, wherein the displacement mechanism further comprises a second spring, wherein unloading of the second spring results in retraction of the penetrating member into the protective member subsequent to subcutaneous insertion of the insertable element.

6. The insertion apparatus according to claim 1, further comprising a user-actuated button for actuating the displacement mechanism when the cartridge unit is loaded therein.

7. The insertion apparatus according to claim 1, further comprising a safety means for preventing inadvertent actuation of the displacement mechanism.

8. The insertion apparatus according to claim 1, wherein the displacement mechanism comprises one or more hooks configured to engage with at least a portion of the cartridge unit when the cartridge unit is loaded within the housing.

9. The insertion apparatus according to claim 1, wherein the displacement mechanism comprises:
   a release button having a restraining arm;
   a ratchet flywheel;
   a loadable flywheel torsion spring at least a portion of which is embedded in the ratchet flywheel;
   a manually rotatable loading button capable of being coupled to the ratchet flywheel for loading the flywheel torsion spring;
   a ratchet crank coupled to the ratchet flywheel and rotatable by the flywheel torsion spring; and
   an insertion lever provided with at least one engagement hook and displaceable by the ratchet crank, wherein:
      upon coupling the loading button to the ratchet flywheel and subsequent rotation of the loading button the flywheel torsion spring is loaded,
      upon actuation of the release button, the restraining arm of the release button is disengaged from the ratchet crank allowing the ratchet crank to rotate via an application of force of the loaded flywheel torsion spring, and
      the ratchet crank displaces the insertion lever and the at least one engagement hook resulting in the protraction of the at least one insertable element and the at least one penetrating member toward the body of the patient and, subsequently, the retraction of the penetrating member, thereby retaining the insertable element in the body of the patient.

10. The insertion apparatus according to claim 1, wherein at least one of the first and second housing openings is further configured for unloading therethrough at least a portion of the at least one cartridge unit from the housing.

11. The insertion apparatus according to claim 1, wherein the first housing opening is further configured for unloading therethrough the protective member with at least the penetrating member contained therein from the housing.

12. The insertion apparatus according to claim 1, wherein the insertion apparatus is configured for repetitive use via subsequent loading of one or more additional cartridge units.

13. The insertion apparatus according to claim 1, wherein the housing further includes a securing mechanism configured to secure the at least one cartridge unit to the housing upon loading the at least one cartridge unit into the housing.

14. The insertion apparatus according to claim 1, wherein the first housing opening is a side opening.

15. The insertion apparatus according to claim 1, wherein the second housing opening is a bottom opening.

16. The insertion apparatus according to claim 1, wherein the second housing opening is separate from the first housing opening.

17. The insertion apparatus according to claim 1, wherein the housing further comprises one or more recesses configured to engage with one or more corresponding protrusions of the cradle for connecting the insertion apparatus to the cradle.

18. The insertion apparatus according to claim 1, further comprising a mechanism for disconnecting the insertion apparatus from the cradle unit.

19. The subcutaneous insertion apparatus of claim 1, further comprising a selection mechanism configured to set an angle of the insertable element from the plurality of angles with respect to the plane of the bottom housing opening, the selection mechanism comprising a button coupled to the cartridge unit, wherein rotation of the button rotates the cartridge unit in a corresponding direction.

20. The subcutaneous insertion apparatus of claim 1, further comprising a depth selection mechanism configured to set a depth of insertion of the at least one penetrating member.

21. A subcutaneous insertion apparatus comprising:
a housing configured to receive at least one cartridge unit, the at least one cartridge unit comprising a protective member containing therein at least one subcutaneously insertable element and at least one penetrating member, the housing including:
  a side housing opening adapted for at least loading therethrough the at least one cartridge unit into the housing, and
  a bottom housing opening adapted for at least protracting therethrough the at least one insertable element and the at least one penetrating member; and
a displacement mechanism contained within the housing and configured to at least protract the at least one insertable element and the at least one penetrating member through the second housing opening towards the body of the patient for subcutaneous insertion of the at least one insertable element,
wherein the displacement mechanism is configured to be primed for activation prior to the housing receiving the at least one cartridge unit; and
the insertion apparatus is configured to couple to a skin-securable cradle that comprises a tubular protrusion emerging upwardly from the cradle that defines therein a well, the well comprising a plurality of penetration tunnels for directing the subcutaneous insertable element toward a plurality of angles with respect to a plane of a bottom housing opening and configured to serve as a stopper to prevent excessive insertion of the at least one penetrating member and to hold a hub of the at least one subcutaneously insertable element upon retraction of the penetrating member, and the insertion apparatus is configured align the subcutaneous insertable element with any of the plurality of penetration tunnels of the well, so as to insert the subcutaneous insertable element through the aligned tunnel.

* * * * *